US012693552B2

(12) United States Patent

Schmeder et al.

(10) Patent No.: US 12,693,552 B2
(45) Date of Patent: *Jul. 28, 2026

(54) OPTICAL FILTERS AFFECTING COLOR VISION IN A DESIRED MANNER AND DESIGN METHOD THEREOF BY NON-LINEAR OPTIMIZATION

(71) Applicant: ENCHROMA, INC., Berkeley, CA (US)

(72) Inventors: Andrew W. Schmeder, Richmond, CA (US); Donald M. Mcpherson, Oakland, CA (US)

(73) Assignee: EnChroma, Inc., Berkeley, CA (US)

( * ) Notice: Subject to any disclaimer, the term of this patent is extended or adjusted under 35 U.S.C. 154(b) by 728 days.

This patent is subject to a terminal disclaimer.

(21) Appl. No.: 17/947,582

(22) Filed: Sep. 19, 2022

(65) Prior Publication Data

US 2023/0016452 A1      Jan. 19, 2023

Related U.S. Application Data

(63) Continuation of application No. 16/835,084, filed on Mar. 30, 2020, now Pat. No. 11,454,827, which is a
(Continued)

(51) Int. Cl.
*G02C 7/10*          (2006.01)
*G02B 5/22*          (2006.01)
(Continued)

(52) U.S. Cl.
CPC ............. *G02C 7/104* (2013.01); *G02B 5/223* (2013.01); *G02B 27/0012* (2013.01);
(Continued)

(58) Field of Classification Search
CPC ........ G02C 7/104; G02C 7/024; G02C 7/108; G02C 7/102; G02B 5/223; G02B 27/0012; G02B 5/23; A61F 9/065
See application file for complete search history.

(56) References Cited

U.S. PATENT DOCUMENTS 3,877,797 A      4/1975   Thornton, Jr.
4,300,819 A      11/1981  Taylor
(Continued)

FOREIGN PATENT DOCUMENTS

CN          1165967 A      11/1997
CN          101203777 A      6/2008
(Continued)

OTHER PUBLICATIONS

European Search Report corresponding to EP16765436, Sep. 27, 2018, 1 page.
(Continued)

*Primary Examiner* — Matthew Y Lee
(74) *Attorney, Agent, or Firm* — Schmidt Patent Law, Inc.

(57)          ABSTRACT

The invention generally relates to optical filters that provide regulation and/or enhancement of chromatic and luminous aspects of the color appearance of light to human vision, generally to applications of such optical filters, to therapeutic applications of such optical filters, to industrial and safety applications of such optical filters when incorporated, for example, in radiation-protective eyewear, to methods of designing such optical filters, to methods of manufacturing such optical filters, and to designs and methods of incorporating such optical filters into apparatus including, for example, eyewear and illuminants.

17 Claims, 30 Drawing Sheets

Related U.S. Application Data continuation of application No. 15/917,314, filed on Mar. 9, 2018, now Pat. No. 10,606,101, which is a continuation of application No. 15/701,729, filed on Sep. 12, 2017, now Pat. No. 10,606,100, which is a continuation of application No. PCT/US2016/021399, filed on Mar. 8, 2016.

(60) Provisional application No. 62/133,207, filed on Mar. 13, 2015.

(51) Int. Cl.

| | |
|---|---|
| *G02B 27/00* | (2006.01) |
| *G02C 7/02* | (2006.01) |
| *A61F 9/06* | (2006.01) |
| *G02B 5/23* | (2006.01) |

(52) U.S. Cl.
CPC ............. *G02C 7/024* (2013.01); *G02C 7/108* (2013.01); *A61F 9/065* (2013.01); *G02B 5/23* (2013.01); *G02C 7/102* (2013.01)

(56) References Cited

U.S. PATENT DOCUMENTS

| | | | |
|---|---|---|---|
| 4,826,286 A | 5/1989 | Thornton, Jr. | |
| 5,218,386 A | 6/1993 | Levien | |
| 5,270,854 A | 12/1993 | Lee et al. | |
| 5,369,453 A | 11/1994 | Chen et al. | |
| 5,408,278 A | 4/1995 | Christman | |
| 5,574,517 A | 11/1996 | Pang et al. | |
| 5,646,781 A | 7/1997 | Johnson, Jr. | |
| 5,774,202 A | 6/1998 | Abraham et al. | |
| 5,846,457 A * | 12/1998 | Hoffman .......... | B29D 11/00317 |
| | | | 264/2.6 |
| 6,132,044 A | 10/2000 | Sternbergh | |
| 6,145,984 A | 11/2000 | Farwig | |
| 6,149,270 A | 11/2000 | Hayashi | |
| 6,450,652 B1 | 9/2002 | Karpen | |
| 7,106,509 B2 | 9/2006 | Sharp | |
| 7,284,856 B2 | 10/2007 | Duha et al. | |
| 7,393,100 B2 | 7/2008 | Mertz | |
| 7,506,977 B1 | 3/2009 | Aiiso | |
| 7,597,441 B1 | 10/2009 | Farwig | |
| 8,075,942 B1 | 12/2011 | Muray et al. | |
| 8,210,678 B1 | 7/2012 | Farwig | |
| 8,911,082 B2 * | 12/2014 | Ambler .................. | G02C 7/104 |
| | | | 351/159.65 |
| 10,606,100 B2 * | 3/2020 | Schmeder .............. | G02C 7/104 |
| 11,454,827 B2 | 9/2022 | Schmeder et al. | |
| 2002/0126256 A1 | 9/2002 | Larson | |
| 2004/0114242 A1 | 6/2004 | Sharp | |
| 2005/0224703 A1 | 10/2005 | Harada et al. | |
| 2006/0146275 A1 | 7/2006 | Mertz | |
| 2008/0212319 A1 | 9/2008 | Klipstein | |
| 2009/0128895 A1 | 5/2009 | Seo et al. | |
| 2010/0179790 A1 | 7/2010 | Nakauchi et al. | |
| 2010/0182678 A1 | 7/2010 | Southwell | |
| 2011/0068698 A1 | 3/2011 | Swoboda et al. | |
| 2011/0255051 A1 | 10/2011 | McCabe et al. | |
| 2012/0075577 A1 | 3/2012 | Ishak et al. | |
| 2012/0206050 A1 | 8/2012 | Spero | |
| 2013/0056682 A1 | 3/2013 | Harding et al. | |
| 2013/0141693 A1 | 6/2013 | McCabe et al. | |
| 2013/0252000 A1 | 9/2013 | Takiff et al. | |
| 2014/0233105 A1 | 8/2014 | Schmeder et al. | |
| 2016/0077361 A1 | 3/2016 | Wold et al. | |
| 2017/0075143 A1 * | 3/2017 | Saylor .................... | G02C 7/101 |
| 2017/0235160 A1 * | 8/2017 | Larson .................. | G02C 7/104 |
| | | | 351/45 |
| 2017/0315384 A1 | 11/2017 | Saylor et al. | |
| 2018/0203171 A1 | 7/2018 | McPherson | |
| 2019/0094135 A1 | 3/2019 | Barrau | |
| 2023/0176402 A1 * | 6/2023 | McCabe .......... | B29D 11/00865 |
| | | | 351/159.61 |

FOREIGN PATENT DOCUMENTS

| | | |
|---|---|---|
| CN | 101441289 A | 5/2009 |
| CN | 101690248 A | 3/2010 |
| CN | 102947680 A | 2/2013 |
| CN | 103688145 A | 3/2014 |
| CN | 104024891 A | 9/2014 |
| EP | 0519660 A1 | 12/1992 |
| EP | 0939329 A1 | 9/1999 |
| EP | 1986024 A1 | 10/2008 |
| EP | 1340115 B1 | 5/2009 |
| JP | 2000-75128 A | 3/2000 |
| JP | 2003-36033 A | 2/2003 |
| JP | 2005511457 A | 4/2005 |
| JP | 2007094338 A | 8/2007 |
| JP | 2008-134618 A | 5/2008 |
| JP | 2008282757 A | 11/2008 |
| JP | 2014-513315 A | 5/2014 |
| TW | 201431546 A | 8/2014 |
| WO | 95/05621 A1 | 2/1995 |
| WO | 02/42829 A1 | 5/2002 |
| WO | 02/094595 A1 | 11/2002 |
| WO | 2005/071734 A2 | 7/2006 |
| WO | 2013/022744 A2 | 2/2013 |
| WO | 2014/110101 A1 | 7/2014 |
| WO | 2015/179538 A1 | 11/2015 |
| WO | 2016/148984 A1 | 9/2016 |
| WO | 2012/119158 A1 | 9/2017 |

OTHER PUBLICATIONS

Exciton: "ABS 594: Visible Narrow Band Absorber", Aug. 25, 2006, XP055510455, URL: http://www.exciton.com/pdfs/ABS594.pdf, 1 page.

Exciton: "ABS 574: Visible Narrow Band Absorber", Mar. 16, 2011, XP055510453, URL: http://www.exciton.com/pdfs/ABS574-0311.pdf, 1 page.

Sharp, G.D., et al., "Retarder Stack Technology for Color Manipulation", 1999 SID International Symposium Digest of Technical Papers, May 1999, 5 pages.

ANSI ZI0.3-2010; The Accredited Committee Z80 for Ophthalmic Standards; American Standard for Ophthalmics—Nonprescription Sunglass and Fashion Eyewear Requirement; Jun. 7, 2010; 32 pages.

British Standard BS EN 1836:2005, Technical Committee CEN/TC 85 "Eye-protective equipment" Personal eye equipment—Sunglasses and sunglare filters for general use and filters for direct observation of the sun; Sep. 2007; 46 pages.

Rea, M.S. et al., Color Rendering: Beyond Pride and Prejudice; Color Research and Application, Dec. 2010; pp. 401-409; vol. 35; No. 6, 2010, Wiley Periodical, Inc.

Drum, Bruce; FDA regulation of labeling and promotional claims in the therapeutic color vision devices; A tutorial; Visual Neuroscience (2004), 21; pp. 461-463.

Tilsch, Markus K., et al., Manufacturing of precision optical coatings; Chinese Optics Letters, vol. 8, Supplement; Apr. 30, 2010; pp. 38-43.

Moreland, Jack D., et al. Quantitative assessment of commercial filter "aids" for red-green colour defectives; Opthal. Physiol. Opt. 2010 30: No. 5; pp. 685-692.

Vorobyev, Misha, et al., Receptor noise as a determinant of colour thresholds; Proc. R. Soc. Lond. B. (1998) 265; pp. 351-358.

PCT/US12/27790; filed Mar. 5, 2012; Written Opinion of the ISA and ISR; 20 pages; mailed Jul. 27, 2012.

PCT/US12/27790; filed Mar. 5, 2012; International Preliminary Report on Patentability (1 pg.) dated Sep. 3, 2013 and Written Opinion (14 pages.); mailed Jul. 27, 2012.

Kirkpatrick, S. et al., Optimization by Simulated Annealing; Science, vol. 22, No. 4598, May 13, 1983, pp. 671-680.

Linear programming: Feb. 28, 2011; XP055027872; Retrieved from the Internet: [on May 23, 2012] URL: http://en/wikipedia.org/w/index.php?title=Linear_programming&oldid=416428507.

Swilliam, Mohammed A., et al. Multilayer Optical coatings Using Convex Optimization; Journal of Lightwave Technology, IEEE Service Center, New Yor, NY, US; vol. 25, No. 4, Apr. 1, 2007; pp. 1078-1085.

(56)  References Cited

OTHER PUBLICATIONS

European Extended Search Report corresponding to EP 14165905.
2; Jan. 2015; 15 pages.
ISR corresponding to PCT/US16/51542, Dec. 5, 2016, 1 page.
ISR corresponding to PCT/US17/55200, Nov. 30, 2017, 1 page.

* cited by examiner

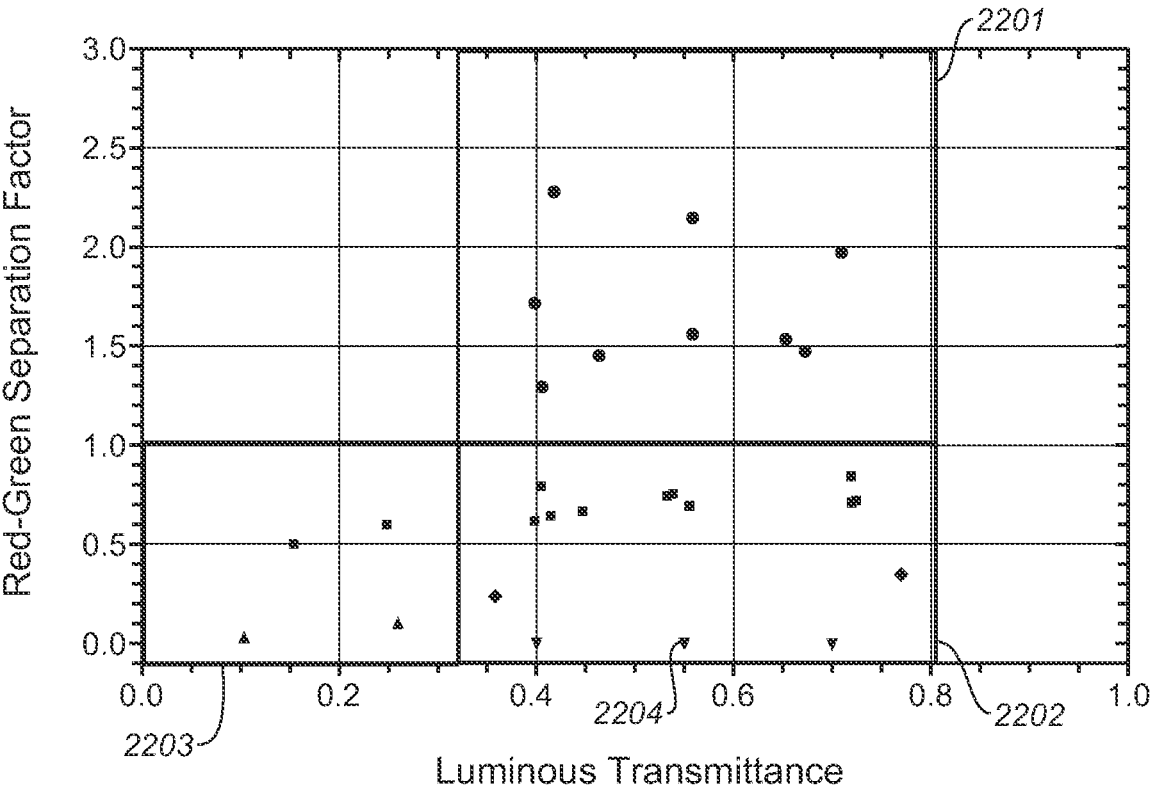
FIG. 22
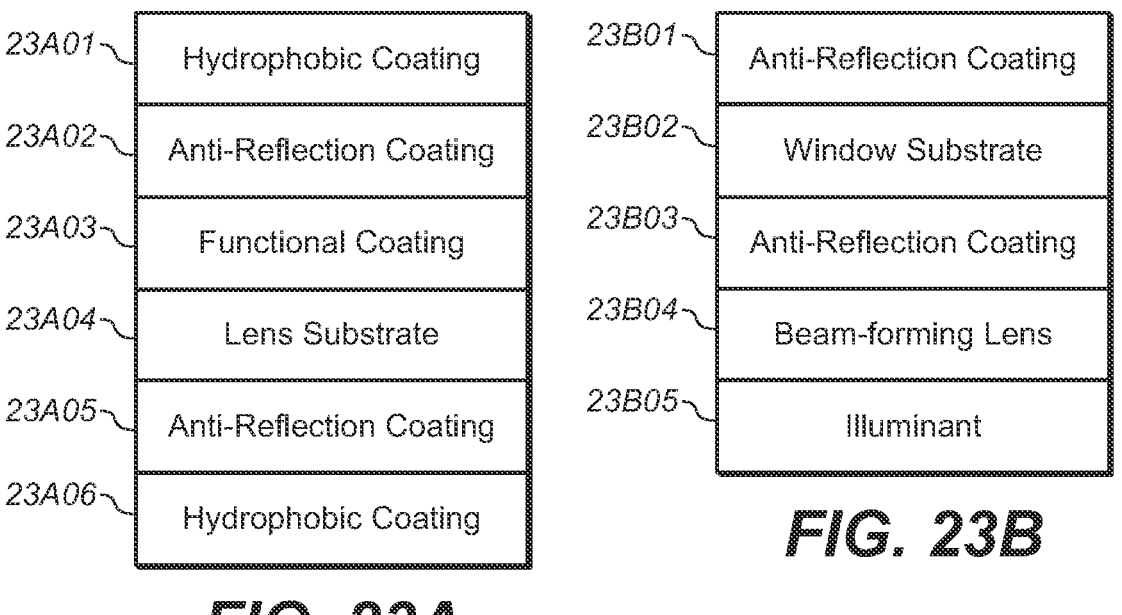
FIG. 23A
FIG. 23B

FIG. 26

Table 1: Normalized Optical Density of Standard Dyes

| nm | SD415Y | SD435Y | SD510R | SD565P | SD600V | SD675B |
|---|---|---|---|---|---|---|
| 400 | 0.93 | 0.6 | 0.16 | 0.11 | 0.061 | 0.22 |
| 405 | 0.97 | 0.63 | 0.18 | 0.11 | 0.057 | 0.2 |
| 410 | 0.99 | 0.69 | 0.2 | 0.1 | 0.056 | 0.18 |
| 415 | 1 | 0.84 | 0.22 | 0.097 | 0.054 | 0.16 |
| 420 | 1 | 0.99 | 0.25 | 0.094 | 0.053 | 0.15 |
| 425 | 0.98 | 0.96 | 0.28 | 0.094 | 0.053 | 0.14 |
| 430 | 0.94 | 0.83 | 0.31 | 0.094 | 0.052 | 0.14 |
| 435 | 0.89 | 0.76 | 0.35 | 0.093 | 0.053 | 0.13 |
| 440 | 0.83 | 0.85 | 0.39 | 0.092 | 0.053 | 0.12 |
| 445 | 0.75 | 0.98 | 0.42 | 0.091 | 0.053 | 0.12 |
| 450 | 0.67 | 0.9 | 0.46 | 0.094 | 0.052 | 0.12 |
| 455 | 0.59 | 0.6 | 0.5 | 0.1 | 0.051 | 0.11 |
| 460 | 0.51 | 0.3 | 0.55 | 0.11 | 0.05 | 0.11 |
| 465 | 0.44 | 0.12 | 0.61 | 0.12 | 0.05 | 0.11 |
| 470 | 0.36 | 0.049 | 0.67 | 0.13 | 0.052 | 0.11 |
| 475 | 0.29 | 0.021 | 0.74 | 0.14 | 0.054 | 0.1 |
| 480 | 0.23 | 0.011 | 0.81 | 0.16 | 0.059 | 0.1 |
| 485 | 0.19 | 0 | 0.87 | 0.18 | 0.067 | 0.1 |
| 490 | 0.15 | 0 | 0.92 | 0.2 | 0.077 | 0.1 |
| 495 | 0.13 | 0 | 0.96 | 0.23 | 0.092 | 0.1 |
| 500 | 0.11 | 0 | 0.98 | 0.25 | 0.11 | 0.1 |
| 505 | 0.098 | 0 | 1 | 0.28 | 0.13 | 0.11 |
| 510 | 0.091 | 0 | 1 | 0.32 | 0.16 | 0.11 |
| 515 | 0.087 | 0 | 0.98 | 0.38 | 0.2 | 0.11 |
| 520 | 0.085 | 0 | 0.94 | 0.43 | 0.24 | 0.11 |
| 525 | 0.083 | 0 | 0.87 | 0.47 | 0.29 | 0.12 |
| 530 | 0.082 | 0 | 0.77 | 0.48 | 0.35 | 0.12 |
| 535 | 0.081 | 0 | 0.66 | 0.5 | 0.42 | 0.13 |
| 540 | 0.081 | 0 | 0.53 | 0.53 | 0.49 | 0.14 |
| 545 | 0.081 | 0 | 0.4 | 0.59 | 0.56 | 0.15 |
| 550 | 0.08 | 0 | 0.29 | 0.7 | 0.63 | 0.16 |
| 555 | 0.08 | 0 | 0.21 | 0.84 | 0.68 | 0.18 |
| 560 | 0.08 | 0 | 0.14 | 0.96 | 0.72 | 0.2 |
| 565 | 0.079 | 0 | 0.098 | 1 | 0.75 | 0.22 |
| 570 | 0.08 | 0 | 0.069 | 0.92 | 0.78 | 0.24 |
| 575 | 0.08 | 0 | 0.05 | 0.73 | 0.8 | 0.27 |
| 580 | 0.079 | 0 | 0.039 | 0.51 | 0.83 | 0.3 |
| 585 | 0.079 | 0 | 0.033 | 0.32 | 0.86 | 0.32 |
| 590 | 0.079 | 0 | 0.029 | 0.19 | 0.91 | 0.36 |
| 595 | 0.079 | 0 | 0.027 | 0.11 | 0.96 | 0.4 |
| 600 | 0.079 | 0 | 0.025 | 0.073 | 1 | 0.46 |
| 605 | 0.078 | 0 | 0.024 | 0.053 | 0.99 | 0.51 |
| 610 | 0.078 | 0 | 0.023 | 0.043 | 0.92 | 0.55 |
| 615 | 0.078 | 0 | 0.022 | 0.038 | 0.81 | 0.57 |
| 620 | 0.078 | 0 | 0.021 | 0.037 | 0.67 | 0.58 |
| 625 | 0.078 | 0 | 0.02 | 0.036 | 0.53 | 0.6 |
| 630 | 0.078 | 0 | 0.019 | 0.036 | 0.4 | 0.6 |
| 635 | 0.078 | 0 | 0.019 | 0.037 | 0.3 | 0.6 |
| 640 | 0.077 | 0 | 0.018 | 0.037 | 0.22 | 0.6 |
| 645 | 0.077 | 0 | 0.018 | 0.037 | 0.16 | 0.59 |
| 650 | 0.077 | 0 | 0.018 | 0.037 | 0.12 | 0.6 |
| 655 | 0.078 | 0 | 0.017 | 0.036 | 0.086 | 0.64 |
| 660 | 0.077 | 0 | 0.017 | 0.035 | 0.063 | 0.71 |
| 665 | 0.077 | 0 | 0.017 | 0.034 | 0.045 | 0.84 |
| 670 | 0.077 | 0 | 0.016 | 0.033 | 0.033 | 0.96 |
| 675 | 0.077 | 0 | 0.016 | 0.032 | 0.025 | 1 |
| 680 | 0.077 | 0 | 0.016 | 0.032 | 0.019 | 0.99 |
| 685 | 0.077 | 0 | 0.016 | 0.032 | 0.016 | 0.89 |
| 690 | 0.077 | 0 | 0.016 | 0.032 | 0.013 | 0.72 |
| 695 | 0.077 | 0 | 0.016 | 0.032 | 0.011 | 0.55 |
| 700 | 0.076 | 0 | 0.015 | 0.032 | 0.01 | 0.43 |

FIG. 27    Table 2: Transmittance of DCB Filter Series

| nm | DCB40 | DCB55 | DCB70 |
|---|---|---|---|
| 400 | 0.86 | 0.9 | 0.95 |
| 405 | 0.87 | 0.91 | 0.95 |
| 410 | 0.87 | 0.91 | 0.96 |
| 415 | 0.88 | 0.92 | 0.96 |
| 420 | 0.88 | 0.92 | 0.96 |
| 425 | 0.88 | 0.92 | 0.96 |
| 430 | 0.88 | 0.92 | 0.96 |
| 435 | 0.88 | 0.92 | 0.96 |
| 440 | 0.88 | 0.92 | 0.96 |
| 445 | 0.88 | 0.92 | 0.96 |
| 450 | 0.88 | 0.92 | 0.96 |
| 455 | 0.88 | 0.92 | 0.96 |
| 460 | 0.88 | 0.92 | 0.96 |
| 465 | 0.87 | 0.91 | 0.96 |
| 470 | 0.86 | 0.91 | 0.95 |
| 475 | 0.85 | 0.9 | 0.95 |
| 480 | 0.84 | 0.89 | 0.94 |
| 485 | 0.82 | 0.88 | 0.94 |
| 490 | 0.8 | 0.86 | 0.93 |
| 495 | 0.77 | 0.84 | 0.92 |
| 500 | 0.74 | 0.82 | 0.91 |
| 505 | 0.71 | 0.79 | 0.89 |
| 510 | 0.66 | 0.76 | 0.87 |
| 515 | 0.61 | 0.72 | 0.85 |
| 520 | 0.56 | 0.68 | 0.82 |
| 525 | 0.51 | 0.64 | 0.8 |
| 530 | 0.47 | 0.6 | 0.78 |
| 535 | 0.42 | 0.56 | 0.75 |
| 540 | 0.38 | 0.52 | 0.72 |
| 545 | 0.33 | 0.48 | 0.69 |

| nm | DCB40 | DCB55 | DCB70 |
|---|---|---|---|
| 550 | 0.28 | 0.43 | 0.66 |
| 555 | 0.24 | 0.39 | 0.62 |
| 560 | 0.21 | 0.36 | 0.6 |
| 565 | 0.2 | 0.34 | 0.58 |
| 570 | 0.2 | 0.34 | 0.59 |
| 575 | 0.22 | 0.36 | 0.6 |
| 580 | 0.24 | 0.38 | 0.62 |
| 585 | 0.25 | 0.4 | 0.63 |
| 590 | 0.26 | 0.4 | 0.63 |
| 595 | 0.25 | 0.4 | 0.63 |
| 600 | 0.24 | 0.39 | 0.62 |
| 605 | 0.25 | 0.39 | 0.63 |
| 610 | 0.27 | 0.42 | 0.65 |
| 615 | 0.32 | 0.47 | 0.69 |
| 620 | 0.39 | 0.53 | 0.73 |
| 625 | 0.47 | 0.61 | 0.78 |
| 630 | 0.56 | 0.68 | 0.83 |
| 635 | 0.65 | 0.75 | 0.87 |
| 640 | 0.72 | 0.8 | 0.9 |
| 645 | 0.78 | 0.85 | 0.92 |
| 650 | 0.83 | 0.88 | 0.94 |
| 655 | 0.87 | 0.91 | 0.95 |
| 660 | 0.9 | 0.93 | 0.97 |
| 665 | 0.92 | 0.95 | 0.97 |
| 670 | 0.94 | 0.96 | 0.98 |
| 675 | 0.95 | 0.97 | 0.98 |
| 680 | 0.96 | 0.97 | 0.99 |
| 685 | 0.96 | 0.97 | 0.99 |
| 690 | 0.96 | 0.98 | 0.99 |
| 695 | 0.97 | 0.98 | 0.99 |
| 700 | 0.97 | 0.98 | 0.99 |

*FIG. 28* Table 3: Transmittance of DCP Filter Series

| nm | DCP40 | DCP55 | DCP70 |
|---|---|---|---|
| 400 | 0.75 | 0.83 | 0.91 |
| 405 | 0.77 | 0.84 | 0.91 |
| 410 | 0.78 | 0.85 | 0.92 |
| 415 | 0.79 | 0.85 | 0.92 |
| 420 | 0.79 | 0.86 | 0.93 |
| 425 | 0.79 | 0.86 | 0.93 |
| 430 | 0.79 | 0.86 | 0.93 |
| 435 | 0.79 | 0.86 | 0.93 |
| 440 | 0.8 | 0.86 | 0.93 |
| 445 | 0.8 | 0.86 | 0.93 |
| 450 | 0.79 | 0.86 | 0.93 |
| 455 | 0.78 | 0.85 | 0.92 |
| 460 | 0.76 | 0.84 | 0.91 |
| 465 | 0.75 | 0.82 | 0.91 |
| 470 | 0.72 | 0.81 | 0.9 |
| 475 | 0.7 | 0.79 | 0.89 |
| 480 | 0.67 | 0.77 | 0.88 |
| 485 | 0.64 | 0.74 | 0.86 |
| 490 | 0.61 | 0.72 | 0.85 |
| 495 | 0.57 | 0.69 | 0.83 |
| 500 | 0.54 | 0.66 | 0.81 |
| 505 | 0.5 | 0.63 | 0.79 |
| 510 | 0.45 | 0.59 | 0.77 |
| 515 | 0.4 | 0.54 | 0.73 |
| 520 | 0.35 | 0.49 | 0.7 |
| 525 | 0.32 | 0.47 | 0.68 |
| 530 | 0.3 | 0.45 | 0.67 |
| 535 | 0.29 | 0.44 | 0.66 |
| 540 | 0.27 | 0.42 | 0.65 |
| 545 | 0.23 | 0.38 | 0.62 |

| nm | DCP40 | DCP55 | DCP70 |
|---|---|---|---|
| 550 | 0.18 | 0.32 | 0.56 |
| 555 | 0.13 | 0.25 | 0.5 |
| 560 | 0.095 | 0.21 | 0.46 |
| 565 | 0.085 | 0.19 | 0.44 |
| 570 | 0.1 | 0.22 | 0.47 |
| 575 | 0.16 | 0.3 | 0.55 |
| 580 | 0.28 | 0.43 | 0.66 |
| 585 | 0.45 | 0.59 | 0.77 |
| 590 | 0.62 | 0.73 | 0.85 |
| 595 | 0.75 | 0.83 | 0.91 |
| 600 | 0.83 | 0.89 | 0.94 |
| 605 | 0.88 | 0.92 | 0.96 |
| 610 | 0.9 | 0.93 | 0.97 |
| 615 | 0.91 | 0.94 | 0.97 |
| 620 | 0.91 | 0.94 | 0.97 |
| 625 | 0.91 | 0.94 | 0.97 |
| 630 | 0.91 | 0.94 | 0.97 |
| 635 | 0.91 | 0.94 | 0.97 |
| 640 | 0.91 | 0.94 | 0.97 |
| 645 | 0.91 | 0.94 | 0.97 |
| 650 | 0.91 | 0.94 | 0.97 |
| 655 | 0.91 | 0.94 | 0.97 |
| 660 | 0.92 | 0.94 | 0.97 |
| 665 | 0.92 | 0.95 | 0.97 |
| 670 | 0.92 | 0.95 | 0.97 |
| 675 | 0.92 | 0.95 | 0.97 |
| 680 | 0.92 | 0.95 | 0.97 |
| 685 | 0.92 | 0.95 | 0.97 |
| 690 | 0.92 | 0.95 | 0.97 |
| 695 | 0.92 | 0.95 | 0.97 |
| 700 | 0.92 | 0.95 | 0.97 |

*FIG. 29*    Table 4: Transmittance of ACE Filter Series

| nm | ACE40 | ACE55 | ACE70 |
|----|-------|-------|-------|
| 400 | 0.45 | 0.59 | 0.77 |
| 405 | 0.41 | 0.55 | 0.74 |
| 410 | 0.4 | 0.55 | 0.74 |
| 415 | 0.39 | 0.53 | 0.73 |
| 420 | 0.41 | 0.55 | 0.74 |
| 425 | 0.42 | 0.56 | 0.75 |
| 430 | 0.43 | 0.57 | 0.75 |
| 435 | 0.48 | 0.61 | 0.78 |
| 440 | 0.51 | 0.64 | 0.8 |
| 445 | 0.55 | 0.67 | 0.82 |
| 450 | 0.57 | 0.69 | 0.83 |
| 455 | 0.59 | 0.7 | 0.84 |
| 460 | 0.59 | 0.71 | 0.84 |
| 465 | 0.6 | 0.71 | 0.84 |
| 470 | 0.58 | 0.7 | 0.83 |
| 475 | 0.58 | 0.69 | 0.83 |
| 480 | 0.59 | 0.71 | 0.84 |
| 485 | 0.6 | 0.71 | 0.84 |
| 490 | 0.6 | 0.71 | 0.85 |
| 495 | 0.61 | 0.72 | 0.85 |
| 500 | 0.59 | 0.71 | 0.84 |
| 505 | 0.56 | 0.68 | 0.82 |
| 510 | 0.49 | 0.62 | 0.79 |
| 515 | 0.36 | 0.51 | 0.71 |
| 520 | 0.25 | 0.39 | 0.63 |
| 525 | 0.32 | 0.46 | 0.68 |
| 530 | 0.36 | 0.5 | 0.71 |
| 535 | 0.44 | 0.58 | 0.76 |
| 540 | 0.55 | 0.67 | 0.82 |
| 545 | 0.59 | 0.7 | 0.84 |

| nm | ACE40 | ACE55 | ACE70 |
|----|-------|-------|-------|
| 550 | 0.62 | 0.73 | 0.85 |
| 555 | 0.64 | 0.74 | 0.86 |
| 560 | 0.63 | 0.73 | 0.86 |
| 565 | 0.5 | 0.63 | 0.79 |
| 570 | 0.17 | 0.3 | 0.55 |
| 575 | 0.086 | 0.19 | 0.44 |
| 580 | 0.093 | 0.2 | 0.45 |
| 585 | 0.058 | 0.15 | 0.39 |
| 590 | 0.097 | 0.21 | 0.46 |
| 595 | 0.2 | 0.34 | 0.58 |
| 600 | 0.33 | 0.48 | 0.69 |
| 605 | 0.42 | 0.56 | 0.75 |
| 610 | 0.48 | 0.61 | 0.78 |
| 615 | 0.54 | 0.66 | 0.81 |
| 620 | 0.56 | 0.68 | 0.82 |
| 625 | 0.56 | 0.68 | 0.82 |
| 630 | 0.55 | 0.67 | 0.82 |
| 635 | 0.55 | 0.67 | 0.82 |
| 640 | 0.55 | 0.67 | 0.82 |
| 645 | 0.53 | 0.66 | 0.81 |
| 650 | 0.52 | 0.65 | 0.81 |
| 655 | 0.53 | 0.66 | 0.81 |
| 660 | 0.55 | 0.67 | 0.82 |
| 665 | 0.58 | 0.7 | 0.84 |
| 670 | 0.6 | 0.71 | 0.85 |
| 675 | 0.62 | 0.73 | 0.85 |
| 680 | 0.64 | 0.74 | 0.86 |
| 685 | 0.66 | 0.76 | 0.87 |
| 690 | 0.7 | 0.79 | 0.89 |
| 695 | 0.75 | 0.82 | 0.91 |
| 700 | 0.78 | 0.85 | 0.92 |

FIG. 30

Table 5: Normalized Optical Density of Narrow Band Dyes

| nm | NBD405 | NBD425 | NBD475 | NBD490 | NBD575 | NBD595 | NBD670 |
|---|---|---|---|---|---|---|---|
| 400 | 0.99 | 0.18 | 0.098 | 0.21 | 0.054 | 0.1 | 0.014 |
| 405 | 0.82 | 0.27 | 0.096 | 0.16 | 0.051 | 0.089 | 0.013 |
| 410 | 0.44 | 0.47 | 0.098 | 0.15 | 0.047 | 0.08 | 0.011 |
| 415 | 0.23 | 0.75 | 0.1 | 0.14 | 0.046 | 0.072 | 0.011 |
| 420 | 0.13 | 1 | 0.11 | 0.15 | 0.044 | 0.065 | 0.01 |
| 425 | 0.078 | 0.71 | 0.12 | 0.16 | 0.044 | 0.06 | 0 |
| 430 | 0.053 | 0.24 | 0.14 | 0.16 | 0.044 | 0.055 | 0 |
| 435 | 0.037 | 0.062 | 0.17 | 0.17 | 0.044 | 0.051 | 0 |
| 440 | 0.026 | 0.019 | 0.21 | 0.18 | 0.044 | 0.048 | 0 |
| 445 | 0.02 | 0.011 | 0.26 | 0.19 | 0.042 | 0.046 | 0.01 |
| 450 | 0.017 | 0 | 0.33 | 0.21 | 0.041 | 0.045 | 0.01 |
| 455 | 0.014 | 0 | 0.45 | 0.23 | 0.04 | 0.044 | 0.01 |
| 460 | 0.012 | 0 | 0.63 | 0.27 | 0.04 | 0.044 |  |
| 465 | 0.012 | 0.011 | 0.83 | 0.31 | 0.04 | 0.044 |  |
| 470 | 0.012 | 0.011 | 0.97 | 0.35 | 0.04 | 0.044 |  |
| 475 | 0.012 | 0.012 | 0.99 | 0.39 | 0.041 | 0.044 |  |
| 480 | 0.012 | 0.012 | 0.84 | 0.47 | 0.042 | 0.044 |  |
| 485 | 0.011 | 0.012 | 0.61 | 0.62 | 0.046 | 0.043 |  |
| 490 | 0.016 | 0.011 | 0.4 | 0.85 | 0.052 | 0.044 |  |
| 495 | 0.029 | 0.011 | 0.24 | 1 | 0.057 | 0.046 |  |
| 500 | 0.052 | 0.011 | 0.15 | 0.88 | 0.062 | 0.05 |  |
| 505 | 0.079 | 0.014 | 0.098 | 0.56 | 0.071 | 0.055 |  |
| 510 | 0.09 | 0.024 | 0.072 | 0.31 | 0.082 | 0.059 |  |
| 515 | 0.066 | 0.042 | 0.057 | 0.18 | 0.095 | 0.064 |  |
| 520 | 0.035 | 0.065 | 0.047 | 0.12 | 0.13 | 0.069 |  |
| 525 | 0.019 | 0.079 | 0.04 | 0.097 | 0.19 | 0.074 |  |
| 530 | 0.013 | 0.068 | 0.036 | 0.081 | 0.18 | 0.083 |  |
| 535 | 0.014 | 0.042 | 0.033 | 0.07 | 0.16 | 0.11 |  |
| 540 | 0.018 | 0.023 | 0.032 | 0.065 | 0.15 | 0.16 |  |
| 545 | 0 | 0.013 | 0.032 | 0.062 | 0.16 | 0.18 |  |
| 550 | 0 | 0 | 0.031 | 0.063 | 0.19 | 0.17 | 0.014 |
| 555 | 0 | 0 | 0.032 | 0.062 | 0.23 | 0.16 | 0.019 |
| 560 | 0 | 0.011 | 0.032 | 0.056 | 0.27 | 0.16 | 0.022 |
| 565 | 0 | 0 | 0.034 | 0.054 | 0.41 | 0.18 | 0.025 |
| 570 | 0 | 0 | 0.04 | 0.056 | 0.76 | 0.19 | 0.029 |
| 575 | 0 | 0 | 0.048 | 0.054 | 1 | 0.21 | 0.036 |
| 580 | 0 | 0 | 0.06 | 0.05 | 0.69 | 0.29 | 0.041 |
| 585 | 0 | 0 | 0.071 | 0.051 | 0.31 | 0.51 | 0.047 |
| 590 | 0 | 0 | 0.081 | 0.05 | 0.13 | 0.85 | 0.065 |
| 595 | 0 | 0 | 0.085 | 0.05 | 0.069 | 1 | 0.11 |
| 600 | 0 | 0 | 0.082 | 0.048 | 0.044 | 0.79 | 0.16 |
| 605 | 0 | 0 | 0.074 | 0.048 | 0.033 | 0.41 | 0.15 |
| 610 | 0 | 0 | 0.066 | 0.046 | 0.028 | 0.19 | 0.13 |
| 615 | 0 | 0 | 0.059 | 0.041 | 0.025 | 0.1 | 0.11 |
| 620 | 0 | 0 | 0.052 | 0.042 | 0.023 | 0.07 | 0.097 |
| 625 | 0 | 0 | 0.049 | 0.042 | 0.022 | 0.057 | 0.098 |
| 630 | 0 | 0 | 0.05 | 0.045 | 0.021 | 0.049 | 0.12 |
| 635 | 0 | 0 | 0.052 | 0.043 | 0.021 | 0.045 | 0.16 |
| 640 | 0 | 0 | 0.054 | 0.039 | 0.02 | 0.041 | 0.18 |
| 645 | 0 | 0 | 0.051 | 0.04 | 0.02 | 0.039 | 0.18 |
| 650 | 0 | 0 | 0.045 | 0.039 | 0.019 | 0.038 | 0.21 |
| 655 | 0 | 0 | 0.036 | 0.041 | 0.019 | 0.036 | 0.33 |
| 660 | 0 | 0 | 0.027 | 0.036 | 0.018 | 0.035 | 0.63 |
| 665 | 0 | 0 | 0.02 | 0.035 | 0.018 | 0.033 | 0.95 |
| 670 | 0 | 0 | 0.015 | 0.035 | 0.017 | 0.032 | 0.95 |
| 675 | 0 | 0 | 0.01 | 0.035 | 0.016 | 0.03 | 0.64 |
| 680 | 0 | 0 | 0 | 0.033 | 0.016 | 0.029 | 0.33 |
| 685 | 0 | 0 | 0 | 0.037 | 0.016 | 0.028 | 0.16 |
| 690 | 0 | 0 | 0 | 0.034 | 0.015 | 0.028 | 0.086 |
| 695 | 0 | 0 | 0 | 0.036 | 0.014 | 0.027 | 0.06 |
| 700 | 0 | 0 | 0 | 0.031 | 0.014 | 0.026 | 0.045 |

*FIG. 31*      Table 6: Transmittance of DMB Filter Series

| nm | DMB40 | DMB55 | DMB70 |
|---|---|---|---|
| 400 | 0.26 | 0.51 | 0.71 |
| 405 | 0.4 | 0.63 | 0.8 |
| 410 | 0.55 | 0.74 | 0.86 |
| 415 | 0.65 | 0.81 | 0.9 |
| 420 | 0.73 | 0.85 | 0.92 |
| 425 | 0.78 | 0.88 | 0.94 |
| 430 | 0.82 | 0.9 | 0.95 |
| 435 | 0.85 | 0.92 | 0.96 |
| 440 | 0.87 | 0.93 | 0.97 |
| 445 | 0.89 | 0.94 | 0.97 |
| 450 | 0.91 | 0.95 | 0.98 |
| 455 | 0.92 | 0.96 | 0.98 |
| 460 | 0.93 | 0.96 | 0.98 |
| 465 | 0.93 | 0.97 | 0.98 |
| 470 | 0.94 | 0.97 | 0.98 |
| 475 | 0.94 | 0.97 | 0.98 |
| 480 | 0.94 | 0.97 | 0.98 |
| 485 | 0.93 | 0.96 | 0.98 |
| 490 | 0.92 | 0.96 | 0.98 |
| 495 | 0.9 | 0.95 | 0.98 |
| 500 | 0.87 | 0.93 | 0.97 |
| 505 | 0.83 | 0.91 | 0.95 |
| 510 | 0.8 | 0.89 | 0.94 |
| 515 | 0.76 | 0.87 | 0.93 |
| 520 | 0.72 | 0.85 | 0.92 |
| 525 | 0.68 | 0.82 | 0.91 |
| 530 | 0.62 | 0.79 | 0.89 |
| 535 | 0.49 | 0.7 | 0.84 |
| 540 | 0.29 | 0.54 | 0.73 |
| 545 | 0.22 | 0.47 | 0.68 |

| nm | DMB40 | DMB55 | DMB70 |
|---|---|---|---|
| 550 | 0.26 | 0.51 | 0.71 |
| 555 | 0.29 | 0.53 | 0.73 |
| 560 | 0.27 | 0.52 | 0.72 |
| 565 | 0.24 | 0.49 | 0.7 |
| 570 | 0.21 | 0.46 | 0.68 |
| 575 | 0.17 | 0.41 | 0.64 |
| 580 | 0.085 | 0.29 | 0.54 |
| 585 | 0.01 | 0.1 | 0.32 |
| 590 | 0 | 0.019 | 0.14 |
| 595 | 0 | 0 | 0.084 |
| 600 | 0 | 0.019 | 0.14 |
| 605 | 0.016 | 0.13 | 0.36 |
| 610 | 0.17 | 0.42 | 0.64 |
| 615 | 0.46 | 0.68 | 0.82 |
| 620 | 0.65 | 0.81 | 0.9 |
| 625 | 0.76 | 0.87 | 0.93 |
| 630 | 0.82 | 0.91 | 0.95 |
| 635 | 0.85 | 0.92 | 0.96 |
| 640 | 0.88 | 0.94 | 0.97 |
| 645 | 0.89 | 0.95 | 0.97 |
| 650 | 0.91 | 0.95 | 0.98 |
| 655 | 0.91 | 0.95 | 0.98 |
| 660 | 0.92 | 0.96 | 0.98 |
| 665 | 0.93 | 0.97 | 0.98 |
| 670 | 0.94 | 0.97 | 0.98 |
| 675 | 0.95 | 0.97 | 0.98 |
| 680 | 0.95 | 0.98 | 0.99 |
| 685 | 0.96 | 0.98 | 0.99 |
| 690 | 0.96 | 0.98 | 0.99 |
| 695 | 0.96 | 0.98 | 0.99 |
| 700 | 0.97 | 0.98 | 0.99 |

*FIG. 32* Table 7: Transmittance of DCP Filter Series

| nm | DCP40 | DCP55 | DCP70 |
|---|---|---|---|
| 400 | 0.75 | 0.83 | 0.91 |
| 405 | 0.77 | 0.84 | 0.91 |
| 410 | 0.78 | 0.85 | 0.92 |
| 415 | 0.79 | 0.85 | 0.92 |
| 420 | 0.79 | 0.86 | 0.93 |
| 425 | 0.79 | 0.86 | 0.93 |
| 430 | 0.79 | 0.86 | 0.93 |
| 435 | 0.79 | 0.86 | 0.93 |
| 440 | 0.8 | 0.86 | 0.93 |
| 445 | 0.8 | 0.86 | 0.93 |
| 450 | 0.79 | 0.86 | 0.93 |
| 455 | 0.78 | 0.85 | 0.92 |
| 460 | 0.76 | 0.84 | 0.91 |
| 465 | 0.75 | 0.82 | 0.91 |
| 470 | 0.72 | 0.81 | 0.9 |
| 475 | 0.7 | 0.79 | 0.89 |
| 480 | 0.67 | 0.77 | 0.88 |
| 485 | 0.64 | 0.74 | 0.86 |
| 490 | 0.61 | 0.72 | 0.85 |
| 495 | 0.57 | 0.69 | 0.83 |
| 500 | 0.54 | 0.66 | 0.81 |
| 505 | 0.5 | 0.63 | 0.79 |
| 510 | 0.45 | 0.59 | 0.77 |
| 515 | 0.4 | 0.54 | 0.73 |
| 520 | 0.35 | 0.49 | 0.7 |
| 525 | 0.32 | 0.47 | 0.68 |
| 530 | 0.3 | 0.45 | 0.67 |
| 535 | 0.29 | 0.44 | 0.66 |
| 540 | 0.27 | 0.42 | 0.65 |
| 545 | 0.23 | 0.38 | 0.62 |

| nm | DCP40 | DCP55 | DCP70 |
|---|---|---|---|
| 550 | 0.18 | 0.32 | 0.56 |
| 555 | 0.13 | 0.25 | 0.5 |
| 560 | 0.095 | 0.21 | 0.46 |
| 565 | 0.085 | 0.19 | 0.44 |
| 570 | 0.1 | 0.22 | 0.47 |
| 575 | 0.16 | 0.3 | 0.55 |
| 580 | 0.28 | 0.43 | 0.66 |
| 585 | 0.45 | 0.59 | 0.77 |
| 590 | 0.62 | 0.73 | 0.85 |
| 595 | 0.75 | 0.83 | 0.91 |
| 600 | 0.83 | 0.89 | 0.94 |
| 605 | 0.88 | 0.92 | 0.96 |
| 610 | 0.9 | 0.93 | 0.97 |
| 615 | 0.91 | 0.94 | 0.97 |
| 620 | 0.91 | 0.94 | 0.97 |
| 625 | 0.91 | 0.94 | 0.97 |
| 630 | 0.91 | 0.94 | 0.97 |
| 635 | 0.91 | 0.94 | 0.97 |
| 640 | 0.91 | 0.94 | 0.97 |
| 645 | 0.91 | 0.94 | 0.97 |
| 650 | 0.91 | 0.94 | 0.97 |
| 655 | 0.91 | 0.94 | 0.97 |
| 660 | 0.92 | 0.94 | 0.97 |
| 665 | 0.92 | 0.95 | 0.97 |
| 670 | 0.92 | 0.95 | 0.97 |
| 675 | 0.92 | 0.95 | 0.97 |
| 680 | 0.92 | 0.95 | 0.97 |
| 685 | 0.92 | 0.95 | 0.97 |
| 690 | 0.92 | 0.95 | 0.97 |
| 695 | 0.92 | 0.95 | 0.97 |
| 700 | 0.92 | 0.95 | 0.97 |

*FIG. 33*  Table 8: Transmittance of CXB Filter Series

| nm | CXB40 | CXB55 | CXB65 |
|---|---|---|---|
| 400 | 0.46 | 0.59 | 0.67 |
| 405 | 0.57 | 0.69 | 0.75 |
| 410 | 0.65 | 0.76 | 0.81 |
| 415 | 0.7 | 0.8 | 0.85 |
| 420 | 0.72 | 0.83 | 0.87 |
| 425 | 0.73 | 0.84 | 0.88 |
| 430 | 0.72 | 0.84 | 0.89 |
| 435 | 0.71 | 0.84 | 0.89 |
| 440 | 0.68 | 0.83 | 0.89 |
| 445 | 0.65 | 0.82 | 0.88 |
| 450 | 0.61 | 0.8 | 0.86 |
| 455 | 0.55 | 0.76 | 0.84 |
| 460 | 0.47 | 0.71 | 0.8 |
| 465 | 0.38 | 0.65 | 0.75 |
| 470 | 0.3 | 0.58 | 0.7 |
| 475 | 0.27 | 0.55 | 0.67 |
| 480 | 0.26 | 0.55 | 0.67 |
| 485 | 0.3 | 0.58 | 0.7 |
| 490 | 0.39 | 0.65 | 0.75 |
| 495 | 0.5 | 0.73 | 0.82 |
| 500 | 0.61 | 0.8 | 0.86 |
| 505 | 0.68 | 0.83 | 0.88 |
| 510 | 0.7 | 0.84 | 0.89 |
| 515 | 0.7 | 0.84 | 0.89 |
| 520 | 0.68 | 0.83 | 0.89 |
| 525 | 0.61 | 0.8 | 0.88 |
| 530 | 0.57 | 0.77 | 0.86 |
| 535 | 0.57 | 0.73 | 0.81 |
| 540 | 0.49 | 0.63 | 0.69 |
| 545 | 0.44 | 0.57 | 0.64 |

| nm | CXB40 | CXB55 | CXB65 |
|---|---|---|---|
| 550 | 0.43 | 0.59 | 0.67 |
| 555 | 0.4 | 0.59 | 0.69 |
| 560 | 0.36 | 0.57 | 0.68 |
| 565 | 0.3 | 0.53 | 0.66 |
| 570 | 0.18 | 0.45 | 0.63 |
| 575 | 0.09 | 0.36 | 0.6 |
| 580 | 0.081 | 0.3 | 0.49 |
| 585 | 0.089 | 0.19 | 0.27 |
| 590 | 0.054 | 0.077 | 0.1 |
| 595 | 0.035 | 0.045 | 0.06 |
| 600 | 0.064 | 0.08 | 0.1 |
| 605 | 0.2 | 0.25 | 0.3 |
| 610 | 0.42 | 0.51 | 0.59 |
| 615 | 0.58 | 0.7 | 0.78 |
| 620 | 0.66 | 0.78 | 0.86 |
| 625 | 0.69 | 0.82 | 0.9 |
| 630 | 0.71 | 0.84 | 0.92 |
| 635 | 0.69 | 0.83 | 0.93 |
| 640 | 0.67 | 0.83 | 0.94 |
| 645 | 0.67 | 0.83 | 0.94 |
| 650 | 0.67 | 0.83 | 0.95 |
| 655 | 0.64 | 0.82 | 0.95 |
| 660 | 0.55 | 0.77 | 0.96 |
| 665 | 0.38 | 0.67 | 0.96 |
| 670 | 0.29 | 0.6 | 0.97 |
| 675 | 0.33 | 0.64 | 0.98 |
| 680 | 0.49 | 0.74 | 0.98 |
| 685 | 0.68 | 0.85 | 0.98 |
| 690 | 0.8 | 0.91 | 0.98 |
| 695 | 0.86 | 0.93 | 0.99 |
| 700 | 0.89 | 0.95 | 0.99 |

*FIG. 34*    Table 9: Transmittance of CXV Filter Series

| nm | CXV40 | CXV55 | CXV65 |
|---|---|---|---|
| 400 | 0.53 | 0.62 | 0.8 |
| 405 | 0.61 | 0.7 | 0.83 |
| 410 | 0.68 | 0.76 | 0.86 |
| 415 | 0.71 | 0.79 | 0.88 |
| 420 | 0.72 | 0.79 | 0.88 |
| 425 | 0.71 | 0.79 | 0.87 |
| 430 | 0.69 | 0.77 | 0.86 |
| 435 | 0.66 | 0.75 | 0.85 |
| 440 | 0.63 | 0.72 | 0.83 |
| 445 | 0.57 | 0.68 | 0.81 |
| 450 | 0.52 | 0.63 | 0.78 |
| 455 | 0.44 | 0.56 | 0.75 |
| 460 | 0.34 | 0.48 | 0.69 |
| 465 | 0.25 | 0.39 | 0.62 |
| 470 | 0.18 | 0.32 | 0.55 |
| 475 | 0.14 | 0.26 | 0.52 |
| 480 | 0.098 | 0.2 | 0.51 |
| 485 | 0.053 | 0.11 | 0.54 |
| 490 | 0.029 | 0.066 | 0.62 |
| 495 | 0.026 | 0.056 | 0.7 |
| 500 | 0.054 | 0.098 | 0.77 |
| 505 | 0.2 | 0.27 | 0.81 |
| 510 | 0.42 | 0.5 | 0.82 |
| 515 | 0.56 | 0.62 | 0.82 |
| 520 | 0.62 | 0.66 | 0.79 |
| 525 | 0.6 | 0.62 | 0.72 |
| 530 | 0.59 | 0.6 | 0.69 |
| 535 | 0.59 | 0.62 | 0.72 |
| 540 | 0.52 | 0.58 | 0.74 |
| 545 | 0.47 | 0.55 | 0.72 |

| nm | CXV40 | CXV55 | CXV65 |
|---|---|---|---|
| 550 | 0.48 | 0.53 | 0.68 |
| 555 | 0.46 | 0.49 | 0.61 |
| 560 | 0.43 | 0.46 | 0.57 |
| 565 | 0.38 | 0.4 | 0.5 |
| 570 | 0.26 | 0.24 | 0.31 |
| 575 | 0.16 | 0.13 | 0.17 |
| 580 | 0.14 | 0.13 | 0.19 |
| 585 | 0.12 | 0.19 | 0.39 |
| 590 | 0.065 | 0.18 | 0.68 |
| 595 | 0.042 | 0.16 | 0.83 |
| 600 | 0.08 | 0.24 | 0.89 |
| 605 | 0.26 | 0.46 | 0.92 |
| 610 | 0.54 | 0.7 | 0.94 |
| 615 | 0.73 | 0.84 | 0.95 |
| 620 | 0.82 | 0.9 | 0.96 |
| 625 | 0.87 | 0.93 | 0.96 |
| 630 | 0.89 | 0.94 | 0.96 |
| 635 | 0.9 | 0.94 | 0.96 |
| 640 | 0.9 | 0.95 | 0.96 |
| 645 | 0.9 | 0.95 | 0.95 |
| 650 | 0.91 | 0.95 | 0.96 |
| 655 | 0.91 | 0.95 | 0.96 |
| 660 | 0.93 | 0.96 | 0.97 |
| 665 | 0.94 | 0.97 | 0.97 |
| 670 | 0.95 | 0.97 | 0.98 |
| 675 | 0.96 | 0.98 | 0.98 |
| 680 | 0.97 | 0.98 | 0.99 |
| 685 | 0.97 | 0.98 | 0.99 |
| 690 | 0.97 | 0.99 | 0.99 |
| 695 | 0.98 | 0.99 | 0.99 |
| 700 | 0.98 | 0.99 | 0.99 |

*FIG. 35*    Table 10: Transmittance of CXN Filter Series

| nm | CXN40 | CXN25 | CXN15 |
|---|---|---|---|
| 400 | 0.54 | 0.36 | 0.23 |
| 405 | 0.61 | 0.44 | 0.31 |
| 410 | 0.66 | 0.5 | 0.36 |
| 415 | 0.68 | 0.52 | 0.38 |
| 420 | 0.68 | 0.52 | 0.38 |
| 425 | 0.66 | 0.49 | 0.35 |
| 430 | 0.63 | 0.46 | 0.31 |
| 435 | 0.59 | 0.41 | 0.26 |
| 440 | 0.55 | 0.36 | 0.22 |
| 445 | 0.49 | 0.29 | 0.16 |
| 450 | 0.42 | 0.23 | 0.11 |
| 455 | 0.34 | 0.16 | 0.063 |
| 460 | 0.25 | 0.09 | 0.027 |
| 465 | 0.17 | 0.045 | 0 |
| 470 | 0.11 | 0.022 | 0 |
| 475 | 0.077 | 0.012 | 0 |
| 480 | 0.052 | 0 | 0 |
| 485 | 0.026 | 0 | 0 |
| 490 | 0.013 | 0 | 0 |
| 495 | 0.012 | 0 | 0 |
| 500 | 0.03 | 0.047 | 0.01 |
| 505 | 0.15 | 0.2 | 0.088 |
| 510 | 0.36 | 0.35 | 0.21 |
| 515 | 0.52 | 0.43 | 0.29 |
| 520 | 0.59 | 0.42 | 0.29 |
| 525 | 0.58 | 0.42 | 0.27 |
| 530 | 0.57 | 0.42 | 0.28 |
| 535 | 0.61 | 0.45 | 0.31 |
| 540 | 0.59 | 0.42 | 0.29 |
| 545 | 0.57 | 0.39 | 0.26 |

| nm | CXN40 | CXN25 | CXN15 |
|---|---|---|---|
| 550 | 0.54 | 0.36 | 0.24 |
| 555 | 0.49 | 0.32 | 0.19 |
| 560 | 0.45 | 0.28 | 0.16 |
| 565 | 0.39 | 0.22 | 0.11 |
| 570 | 0.24 | 0.11 | 0.039 |
| 575 | 0.13 | 0.043 | 0 |
| 580 | 0.13 | 0.043 | 0.01 |
| 585 | 0.21 | 0.075 | 0.027 |
| 590 | 0.24 | 0.077 | 0.035 |
| 595 | 0.23 | 0.062 | 0.028 |
| 600 | 0.27 | 0.086 | 0.041 |
| 605 | 0.38 | 0.17 | 0.092 |
| 610 | 0.5 | 0.3 | 0.18 |
| 615 | 0.58 | 0.4 | 0.26 |
| 620 | 0.62 | 0.45 | 0.31 |
| 625 | 0.64 | 0.47 | 0.33 |
| 630 | 0.63 | 0.47 | 0.32 |
| 635 | 0.6 | 0.43 | 0.29 |
| 640 | 0.57 | 0.39 | 0.25 |
| 645 | 0.56 | 0.38 | 0.24 |
| 650 | 0.56 | 0.39 | 0.24 |
| 655 | 0.51 | 0.33 | 0.19 |
| 660 | 0.39 | 0.21 | 0.1 |
| 665 | 0.21 | 0.082 | 0.024 |
| 670 | 0.13 | 0.039 | 0 |
| 675 | 0.16 | 0.054 | 0.013 |
| 680 | 0.3 | 0.15 | 0.058 |
| 685 | 0.53 | 0.36 | 0.22 |
| 690 | 0.71 | 0.57 | 0.43 |
| 695 | 0.79 | 0.69 | 0.57 |
| 700 | 0.83 | 0.74 | 0.64 |

FIG. 36  Table 11: Transmittance of UVH Filter Series

| nm | UVH415 | UVH430 | UVH450 |
|---|---|---|---|
| 400 | 0.022 | 0 | 0 |
| 405 | 0.038 | 0 | 0 |
| 410 | 0.13 | 0.027 | 0 |
| 415 | 0.21 | 0.033 | 0 |
| 420 | 0.24 | 0.024 | 0 |
| 425 | 0.38 | 0.077 | 0 |
| 430 | 0.64 | 0.36 | 0 |
| 435 | 0.8 | 0.67 | 0 |
| 440 | 0.87 | 0.8 | 0 |
| 445 | 0.9 | 0.85 | 0 |
| 450 | 0.91 | 0.87 | 0.03 |
| 455 | 0.92 | 0.88 | 0.13 |
| 460 | 0.93 | 0.89 | 0.3 |
| 465 | 0.93 | 0.88 | 0.43 |
| 470 | 0.93 | 0.88 | 0.48 |
| 475 | 0.92 | 0.88 | 0.52 |
| 480 | 0.93 | 0.88 | 0.53 |
| 485 | 0.93 | 0.88 | 0.49 |
| 490 | 0.91 | 0.87 | 0.37 |
| 495 | 0.87 | 0.81 | 0.21 |
| 500 | 0.8 | 0.72 | 0.11 |
| 505 | 0.72 | 0.63 | 0.07 |
| 510 | 0.68 | 0.58 | 0.089 |
| 515 | 0.73 | 0.61 | 0.12 |
| 520 | 0.8 | 0.66 | 0.14 |
| 525 | 0.83 | 0.68 | 0.19 |
| 530 | 0.86 | 0.72 | 0.25 |
| 535 | 0.86 | 0.76 | 0.27 |
| 540 | 0.84 | 0.76 | 0.37 |
| 545 | 0.87 | 0.81 | |
| 550 | 0.9 | 0.85 | 0.47 |
| 555 | 0.91 | 0.86 | 0.5 |
| 560 | 0.91 | 0.85 | 0.49 |
| 565 | 0.9 | 0.85 | 0.48 |
| 570 | 0.9 | 0.86 | 0.5 |
| 575 | 0.89 | 0.85 | 0.47 |
| 580 | 0.86 | 0.8 | 0.38 |
| 585 | 0.76 | 0.68 | 0.18 |
| 590 | 0.64 | 0.53 | 0.064 |
| 595 | 0.59 | 0.48 | 0.039 |
| 600 | 0.66 | 0.55 | 0.077 |
| 605 | 0.81 | 0.74 | 0.27 |
| 610 | 0.91 | 0.87 | 0.54 |
| 615 | 0.95 | 0.93 | 0.72 |
| 620 | 0.96 | 0.95 | 0.79 |
| 625 | 0.97 | 0.96 | 0.83 |
| 630 | 0.97 | 0.96 | 0.84 |
| 635 | 0.98 | 0.96 | 0.84 |
| 640 | 0.98 | 0.96 | 0.85 |
| 645 | 0.98 | 0.97 | 0.86 |
| 650 | 0.98 | 0.97 | 0.86 |
| 655 | 0.98 | 0.97 | 0.86 |
| 660 | 0.98 | 0.97 | 0.88 |
| 665 | 0.98 | 0.97 | 0.86 |
| 670 | 0.98 | 0.97 | 0.87 |
| 675 | 0.98 | 0.97 | 0.88 |
| 680 | 0.98 | 0.97 | 0.88 |
| 685 | 0.99 | 0.98 | 0.89 |
| 690 | 0.99 | 0.98 | 0.9 |
| 695 | 0.98 | 0.97 | 0.87 |
| 700 | 0.99 | 0.98 | 0.91 |

*FIG. 37*　　Table 12: Transmittance of ACR Filter Series

| nm | ACR25R | ACR10R |
|---|---|---|
| 400 | 0.33 | 0.13 |
| 405 | 0.35 | 0.14 |
| 410 | 0.35 | 0.14 |
| 415 | 0.33 | 0.13 |
| 420 | 0.3 | 0.12 |
| 425 | 0.27 | 0.11 |
| 430 | 0.24 | 0.095 |
| 435 | 0.21 | 0.082 |
| 440 | 0.18 | 0.07 |
| 445 | 0.15 | 0.06 |
| 450 | 0.13 | 0.051 |
| 455 | 0.1 | 0.041 |
| 460 | 0.08 | 0.032 |
| 465 | 0.059 | 0.024 |
| 470 | 0.042 | 0.017 |
| 475 | 0.031 | 0.012 |
| 480 | 0.023 | 0 |
| 485 | 0.019 | 0 |
| 490 | 0.016 | 0 |
| 495 | 0.015 | 0 |
| 500 | 0.014 | 0 |
| 505 | 0.014 | 0 |
| 510 | 0.014 | 0 |
| 515 | 0.015 | 0 |
| 520 | 0.017 | 0 |
| 525 | 0.023 | 0 |
| 530 | 0.033 | 0.013 |
| 535 | 0.051 | 0.02 |
| 540 | 0.075 | 0.03 |
| 545 | 0.12 | 0.046 |

| nm | ACR25R | ACR10R |
|---|---|---|
| 550 | 0.19 | 0.076 |
| 555 | 0.28 | 0.11 |
| 560 | 0.37 | 0.15 |
| 565 | 0.43 | 0.17 |
| 570 | 0.46 | 0.18 |
| 575 | 0.47 | 0.19 |
| 580 | 0.39 | 0.16 |
| 585 | 0.21 | 0.086 |
| 590 | 0.078 | 0.031 |
| 595 | 0.044 | 0.018 |
| 600 | 0.08 | 0.032 |
| 605 | 0.25 | 0.1 |
| 610 | 0.52 | 0.21 |
| 615 | 0.7 | 0.28 |
| 620 | 0.78 | 0.31 |
| 625 | 0.83 | 0.33 |
| 630 | 0.85 | 0.34 |
| 635 | 0.86 | 0.34 |
| 640 | 0.87 | 0.35 |
| 645 | 0.87 | 0.35 |
| 650 | 0.88 | 0.35 |
| 655 | 0.88 | 0.35 |
| 660 | 0.89 | 0.36 |
| 665 | 0.9 | 0.36 |
| 670 | 0.91 | 0.36 |
| 675 | 0.91 | 0.36 |
| 680 | 0.91 | 0.36 |
| 685 | 0.92 | 0.37 |
| 690 | 0.92 | 0.37 |
| 695 | 0.92 | 0.37 |
| 700 | 0.92 | 0.37 |

*FIG. 39*

|  | $T_V$ | $\Psi_{RG}$ |
|---|---|---|
| DCB40 | 0.405 | 0.788 |
| DCB55 | 0.533 | 0.736 |
| DCB70 | 0.72 | 0.703 |
| DCP40 | 0.446 | 0.658 |
| DCP55 | 0.555 | 0.686 |
| DCP70 | 0.724 | 0.714 |
| ACE40 | 0.415 | 0.635 |
| ACE55 | 0.538 | 0.745 |
| ACE70 | 0.719 | 0.837 |
| CXN40 | 0.398 | 0.609 |
| CXN25 | 0.248 | 0.594 |
| CXN15 | 0.153 | 0.497 |
| UVH430 | 0.77 | 0.352 |
| UVH450 | 0.358 | 0.24 |
| ACR25R | 0.259 | 0.109 |
| ACR10R | 0.103 | 0.0359 |
| ND40 | 0.4 | 0 |
| ND55 | 0.55 | 0 |
| ND70 | 0.7 | 0 |

Table 14: Properties of Filters with $\Psi_{RG} < 1$

*FIG. 38*

|  | $T_V$ | $\Psi_{RG}$ |
|---|---|---|
| DMB40 | 0.408 | 2.5 |
| DMB55 | 0.565 | 1.97 |
| DMB70 | 0.706 | 1.82 |
| DMP40 | 0.418 | 2.28 |
| DMP55 | 0.558 | 2.15 |
| DMP70 | 0.709 | 1.98 |
| CXB40 | 0.398 | 1.72 |
| CXB55 | 0.558 | 1.57 |
| CXB65 | 0.652 | 1.55 |
| CXV40 | 0.405 | 1.3 |
| CXV55 | 0.464 | 1.46 |
| CXV65 | 0.672 | 1.48 |

Table 13: Properties of Filters with $\Psi_{RG} > 1$ and $T_V > 0.40$

OPTICAL FILTERS AFFECTING COLOR VISION IN A DESIRED MANNER AND DESIGN METHOD THEREOF BY NON-LINEAR OPTIMIZATION

CROSS REFERENCE TO RELATED APPLICATIONS

This application is a continuation of U.S. patent application Ser. No. 16/835,084 filed Mar. 30, 2020, which is a continuation of U.S. patent application Ser. No. 15/917,314 filed Mar. 9, 2018, now U.S. Pat. No. 10,606,101, which is a continuation of U.S. patent application Ser. No. 15/701, 729 filed Sep. 12, 2017, now U.S. Pat. No. 10,606,100, which is a continuation of International Patent Application No. PCT/US2016/021399 filed Mar. 8, 2016 and titled "Optical Filters Affecting Color Vision In A Desired Manner And Design Method Thereof By Non-Linear Optimization". PCT/US2016/021399 claims benefit of priority to U.S. Provisional Patent Application No. 62/133,207 titled "Optical Filters Affecting Color Vision In A Desired Manner And Design Method Thereof By Non-Linear Optimization" filed Mar. 13, 2015. Each of foregoing applications is incorporated herein by reference in their entirety.

This application is also related to U.S. patent application Ser. No. 14/014,991 titled "Multi-Band Color Vision Filters and Method by LP-Optimization" filed Aug. 30, 2013 and to PCT/US2012/027790 titled "Multi-Band Color Vision Filters and Method by LP-Optimization" filed Mar. 5, 2012, both of which are incorporated herein by reference in their entirety.

FIELD OF THE INVENTION

The invention generally relates to optical filters that provide regulation and/or enhancement of chromatic and luminous aspects of the color appearance of light as seen by human color vision, generally to applications of such optical filters, to applications of such optical filters in ophthalmic lenses, to therapeutic applications of such optical filters, to industrial and safety applications of such optical filters when incorporated, for example, in radiation-protective eyewear, to methods of designing such optical filters, to methods of manufacturing such optical filters, and to designs and methods of incorporating such optical filters into optical systems including, for example, eyewear, contact lenses, windows, coatings, and illuminants.

BACKGROUND

Optical filters are devices having wavelength-selective transmission acting on sources or receivers of light. Such filters may be configured to transform aspects of color appearance as seen by the human eye. Optical filters that improve or modify aspects of color vision may provide therapeutic benefit to persons with color vision deficiency, to persons with low-vision disorders and to persons with normal color vision. Optical filters may provide eye-protection from high-energy radiation in the ultra-violet, visible, and/or infrared spectra. Apparatus incorporating optical filters affecting color vision and/or color appearance include eyewear, contact lenses, scope assemblies, cameras, windows, coatings and lamp assemblies. Such apparatus may be generally referred to as optical systems. Apparatus wherein the optical filters act to modify light received by the eye using a lens or shield disposed in front of the face or eye are generally referred to as ophthalmic systems.

SUMMARY

Disclosed herein are methods for designing optical filters that, for example, provide enhancement and/or regulation to the appearance of color with respect to human color perception. The optical filter designs produced by the described methods may be used as the basis for manufacturing specifications to fabricate the optical filters using absorptive optical materials, such as narrow-band absorbing dyes and/or broad-band absorbing dyes. Such filters may be manufactured as a coating applied onto the surface of an optical substrate where the optical substrate is substantially transparent, or may be incorporated into the bulk mass of an optical substrate, or both. The optical substrate may, for example, be incorporated into eyewear (e.g., eyeglasses, sunglasses, face-shields, monocles, safety lenses, contact lenses, or any other suitable ophthalmic lenses), or may be incorporated into scope assemblies (e.g. binoculars), or into camera lenses (e.g. as a filter placed on a camera lens assembly), or may be incorporated into lamp assemblies (e.g., light bulbs, flashlights), or may be incorporated into coatings applied to a reflective surface (e.g. clear-coating applied onto a paper or other substrate that has been pigmented by paint or by a printing process).

An ophthalmic lens is a lens for use with an eye. An ophthalmic lens may provide optical (focusing) correction to the eye, or it may be of zero power and provide no such correction. Eyeglass lenses (e.g., clear or substantially transparent lenses), tinted or colored lenses, sunglass lenses, polarized lenses, gradient lenses, photochromic lenses, multi-focal (e.g. progressive, bifocal and trifocal) lenses and contact lenses are examples of ophthalmic lenses.

Optical filters may be characterized by measurable properties pertaining to their transmittance spectra. Herein, the unqualified use of the term "filter" shall be understood to mean "optical filter", unless otherwise specified. Transmittance is the fraction of light that passes through the filter at a particular wavelength. The transmittance may be stated as a ratio, e.g. 0.40, or as a percent, e.g. 40%. The visible wavelengths of light are between about 390 nanometers and about 750 nanometers, however it is also reasonable to consider only wavelengths between 400 nanometers and about 700 nanometers, or between 420 nanometers and about 670 nanometers, because the human eye is relatively insensitive to light having a wavelength near the ends of the visible spectrum and the properties of filters near the end of the visible spectrum may therefore have little to no impact on color perception. The transmittance spectrum of a filter refers to its transmission across the visible spectrum of light, unless otherwise specified herein. The transmittance spectra of filters may be simulated on a computer by tabulating the transmittance per wavelength, using a wavelength step size of 1 nanometer, for example, or using any other reasonable step size or other sampling method.

The mean transmittance of a filter is the average transmittance over a contiguous range of wavelengths, for example, the mean transmittance between 500 nanometers and 599 nanometers may be calculated by summing the transmittance at each wavelength within the range using a step size of 1 nanometer, and then dividing the sum by 100.

The luminous transmittance of a filter is the weighted average transmittance of a standard illuminant by the filter, where the weighting function is a photopic luminous efficiency function defined by a standard observer model. In the present disclosure the luminous transmittance of a filter is defined as the weighted average transmittance of CIE Standard Illuminant D65 and the weighting function is the photopic luminous efficiency function defined by the CIE 1931 2-degree Standard Observer.

The white-point of a filter is the (x,y) chromaticity coordinates of average daylight as seen through the filter, where average daylight is defined as CIE Standard Illuminant D65 and the (x,y) chromaticity coordinates are calculated according to the CIE 1931 2-degree Standard Observer and the CIE Yxy color space, unless otherwise specified.

The correlated color temperature of a filter is the temperature corresponding to a point on the black-body locus nearest to the white-point of the filter.

Measurement of the transmittance spectra of filters integrated into an ophthalmic system may be performed for example by averaging the measurement over a region of the lens corresponding to at least a 10-degree field of view, when the ophthalmic system is used to filter light received by the eye in a typical fashion. For example, the spectral measurement may be performed by passing a reference light through an area on an eyeglass lens having a diameter between about 5 millimeters and about 20 millimeters at the center of the lens, and then performing a spectral analysis on the light transformed by the ophthalmic system. A similar measurement on a contact lens would use a smaller area that is appropriately chosen and proportional to the diameter of the lens. Measurement of the transmittance spectra of filters integrated into a lamp assembly may comprise averaging the spectral response of the system over a portion of the output beam, for example corresponding to about 10% of the total output light power. Any reasonable method of measuring the spectral response of a filter integrated into a system may be used, wherein the method of measurement is appropriately chosen for consideration of the visual effect that the filter causes (i.e. the effect as seen by a normal unaided human eye).

If an optical filter is incorporated into an ophthalmic lens, then its properties may be measured according to industry-standard conventions and definitions, for example, the calculations just described are defined with respect to eyewear by American National Standards Institute Z80.3-2010 section 4.6 (transmittance), section 4.6.1 (luminous transmittance), section 4.6.2 (mean transmittance), and section 4.6.3.1 (white-point/chromaticity coordinates of average daylight). Similar calculations for contact lenses are defined by ANSI Z80.20-2010, for intraocular lenses by ANSI Z80.7-2002, and for ski and snow goggles by ASTM F659-12.

In one aspect, a computer implemented method for designing an optical filter for affecting color vision in a desired manner, where the filter comprises a combination of two or more dye components, comprises using a computer to simulate the state of a filter given in terms of its component dye concentrations, which are given using a dye-formula in the form $$F = \alpha_1 \Omega_1 + \ldots \alpha_N \Omega_N$$

wherein, in the above formula, $\Omega_i$ represents the dye optical density spectrum and $\alpha_i$ represents the corresponding dye concentration for the $i^{th}$ dye. And, in this method, the transmittance spectrum of the filter, $\tau_F$, is simulated by the combination of the dye components according to the Beer-Lambert law, $$\tau_F = 10^{(-1 \times F)}$$

and, the method comprises repeatedly (iteratively) executing a routine that selects an optimal change to the dye formula (referred to herein as a dye increment), until the filter reaches a desired target luminous transmittance ($\tau_v$). And, at each repetition of the routine the optimal change to the dye formula is selected from a collection of candidate changes, wherein each change corresponds to a small discrete increment in dye concentration for a dye, and the optimal change is the one that maximizes the ratio of change in colorimetric performance per the decrease in luminous transmittance of the corresponding candidate filter, and/or the optimal change is the one that maximizes the ratio of the decrease in distance to the target white-point per the decrease in luminous transmittance of the candidate filter.

In some embodiments the target white-point is a single point in a chromaticity space. In some embodiments the target white-point is a circular region in a chromaticity space. In some embodiments the target white-point is a quadrilateral region in a chromaticity space. In some embodiments the target white-point is on the black-body locus at a location corresponding to a black-body radiator with a color temperature between about 2700 Kelvin and about 10000 Kelvin.

In some embodiments the target white-point is configured so that the resulting filter color is blue (i.e., that the apparent color of white light is transformed to a blue color when passing through the filter). In some embodiments the target white-point is configured so that the filter color is violet. In some embodiments the target white-point is configured so that the filter color is pink. In some embodiments the target white-point is configured so that the filter color is purple. In some embodiments the target white-point is configured so that the filter color is vermillion (vermillion is a pinkish-gray color). In some embodiments the target white-point is configured so that the filter color is yellow. In some embodiments the target white-point is configured so that the filter color is brown. In some embodiments the target white-point is configured so that the filter color is red. In some embodiments the target white-point is configured so that the filter color is gray.

In some embodiments an additional constraint is provided to ensure that the transmittance of the filter between 580 nanometers and 600 nanometers is at least 5%, or is at least $\frac{1}{10}^{th}$ of the luminous transmittance, or is at least $\frac{1}{5}^{th}$ of the luminous transmittance of the filter.

In some embodiments, the method is modified to limit the maximum concentration of certain dyes to comply with solubility limits necessary for manufacturing an article containing that dye in a desired polymeric substrate.

In some embodiments, the method is modified to use recursive look-ahead, so that the calculation of the optimal change considers the best incremental increase in dye concentration taking into account the anticipated future changes that may be needed to maintain the input constraint conditions.

In some embodiments, the method is configured to operate using a set of standard dyes, where a standard dye is defined as a dye having a full-width-half-maximum width greater than 40 nanometers around its peak absorption wavelength. The peak absorption wavelength is the wavelength within the visible spectrum where the optical density of the dye reaches its maximum. Some dyes may have higher optical density in regions outside the visible spectrum (e.g. in the ultra-violet or infrared spectrum), however these properties are not relevant to the design of filters for affecting color vision in a desired manner.

In some embodiments, the method is configured to operate using a set of narrow-band dyes, where a narrow-band dye is defined as a dye having a full-width-half-maximum width of at most 40 nanometers around its peak absorption wavelength.

In some embodiments, the method is configured to operate using a set of dyes including at least one narrow-band dye and at least one standard dye.

In some embodiments, the method is configured to use the red-green separation factor as the colorimetric performance measure.

In some embodiments, the colorimetric performance measure is calculated by measuring the chromaticity gamut area of a set of reference colors (e.g. for a set of Munsell color swatches) as seen through the filter.

In another aspect, a colorimetric performance metric for characterizing a filter for affecting color vision comprises calculating the mean transmittance over three adjacent non-overlapping spectral regions: over a green region between about 500 nanometers and about 555 nanometers ($\tau_G$), over a yellow region between about 555 nanometers and about 600 nanometers ($\tau_Y$), and over a red region between about 600 nanometers and about 650 nanometers ($\tau_R$), and then calculating the luminous transmittance of the filter ($\tau_v$), and then calculating the red-green separation factor of the filter ($\Psi_{RG}$) using the formula:

$$\Psi_{RG} = ((\tau_v \times ((((\tau_G + \tau_R)/2)/\tau_Y) - 1))/(1 - \tau_v) + 1)$$

The red-green separation factor, as defined herein, is zero for neutral filters (filters having a constant transmittance per wavelength), and is greater than zero for filters that enhance the saturation and/or brightness of colors organized along the red-green axis of color space.

In another aspect, a filter for affecting color vision in a desired manner comprises one or more narrow-band dyes, and the filter has a luminous transmittance of at least 40% and a red-green separation factor of at least 1.0.

In some embodiments, the filter comprises two or more narrow-band dyes.

In some embodiments, the filter comprises three or more narrow-band dyes.

In some embodiments, the filter comprises four or more narrow-band dyes.

In some embodiments, the filter comprises five or more narrow-band dyes.

In some embodiments, the filter comprises one or more narrow-band dyes and one or more standard dyes.

In some embodiments, the filter comprises two or more narrow-band dyes and one or more standard dyes.

In some embodiments, the filter comprises three or more narrow-band dyes and one or more standard dyes.

In some embodiments, the filter comprises four or more narrow-band dyes and one or more standard dyes.

In some embodiments, the filter comprises five or more narrow-band dyes and one or more standard dyes.

In some embodiments, the filter has a luminous transmittance that is greater than 40% and has a red-green separation factor that is greater than 1.0.

In some embodiments, the filter has a luminous transmittance that is greater than 40% and has a red-green separation factor that is greater than 1.25.

In some embodiments, the filter has a luminous transmittance that is greater than 40% and has a red-green separation factor that is greater than 1.5.

In some embodiments, the filter has a luminous transmittance that is greater than 40% and has a red-green separation factor that is greater than 2.0.

In some embodiments, the filter has a luminous transmittance that is greater than 50% and has a red-green separation factor that is greater than 1.0.

In some embodiments, the filter has a luminous transmittance that is greater than 50% and has a red-green separation factor that is greater than 1.25.

In some embodiments, the filter has a luminous transmittance that is greater than 50% and has a red-green separation factor that is greater than 1.5.

In some embodiments, the filter has a luminous transmittance that is greater than 50% and has a red-green separation factor that is greater than 2.0.

In some embodiments, the filter has a luminous transmittance that is greater than 60% and has a red-green separation factor that is greater than 1.0.

In some embodiments, the filter has a luminous transmittance that is greater than 60% and has a red-green separation factor that is greater than 1.25.

In some embodiments, the filter has a luminous transmittance that is greater than 60% and has a red-green separation factor that is greater than 1.5.

In some embodiments, the filter has a luminous transmittance that is greater than 60% and has a red-green separation factor that is greater than 2.0.

In some embodiments, wherein the filter has a luminous transmittance of at least about 40% and the filter has a red-green separation factor of at least 1.0, the filter color is blue.

In some embodiments, wherein the filter has a luminous transmittance of at least about 40% and the filter has a red-green separation factor of at least 1.0, the filter color is blue-green.

In some embodiments, wherein the filter has a luminous transmittance of at least about 40% and the filter has a red-green separation factor of at least 1.0, the filter color is violet.

In some embodiments, wherein the filter has a luminous transmittance of at least about 40% and the filter has a red-green separation factor of at least 1.0, the filter color is purple.

In some embodiments, wherein the filter has a luminous transmittance of at least about 40% and the filter has a red-green separation factor of at least 1.0, the filter color is pink.

In some embodiments, wherein the filter has a luminous transmittance of at least about 40% and the filter has a red-green separation factor of at least 1.0, the filter color is vermillion (vermillion is a pinkish-gray).

In some embodiments, the white-point of the filter is configured to have a correlated color temperature between 2700 Kelvin and 10000 Kelvin and the distance of the filter white-point to the black-body locus is at most about 0.05 units in the CIE (x,y) 1931 2-degree standard observer chromaticity space.

In some embodiments, the white-point of the filter is configured to have a correlated color temperature between 2700 Kelvin and 10000 Kelvin and the distance of the filter white-point to the black-body locus is at most about 0.025 units in the CIE (x,y) 1931 2-degree standard observer chromaticity space.

In some embodiments, the filter comprises a first narrow-band dye with peak absorption wavelength of about 575 nanometers, and a second narrow-band dye with peak absorption wavelength of about 595 nanometers.

In some embodiments, the filter comprises a first narrow-band dye with peak absorption wavelength of about 575 nanometers, and a second narrow-band dye with peak absorption wavelength of about 595 nanometers, and the concentration of the dyes are configured so that the transmittance of the filter at 575 nanometers is about 10%+/−5%.

In some embodiments, the filter comprises a first narrow-band dye with peak absorption wavelength of about 575 nanometers, and a second narrow-band dye with peak absorption wavelength of about 595 nanometers, and the concentration of the dyes are configured so that the transmittance of the filter at 595 nanometers is about 5%+/−3%.

In some embodiments, the filter comprises a first narrow-band dye with peak absorption wavelength of about 595 nanometers, and a second narrow-band dye with peak absorption wavelength of about 475 nanometers, and the dye concentrations are configured so that the transmittance of the filter at 475 nanometers is at least about 4 times greater than the transmittance of the filter at 595 nanometers, and so that the luminous transmittance of the filter is at least 40%, or is at least 50%, or is at least 60%.

In some embodiments, the filter comprises a first narrow-band dye with peak absorption wavelength of about 575 nanometers, and a second narrow-band dye with peak absorption wavelength of about 475 nanometers, and the dye concentrations are configured so that the transmittance of the filter at 475 nanometers is at least about 3 times greater than the transmittance of the filter at 575 nanometers, and so that the luminous transmittance of the filter is at least 40%, or is at least 50%, or is at least 60%.

In another aspect, a method for prescribing an ophthalmic lens to an individual suffering from color vision deficiency comprises testing the color vision of the individual and then prescribing (recommending or selecting) a lens containing an optical filter wherein if the individual has deuteranomaly then a lens is selected such that the transmittance of the filter at 575 nanometers is at least two times greater than the transmittance at 595 nanometers, and/or if the individual has protanomaly then a lens is selected such that the transmittance of the filter at 595 nanometers is at least two times greater than the transmittance at 575 nanometers.

In another aspect, a method for prescribing an ophthalmic contact lens to an individual suffering from color vision deficiency comprises testing the color vision of the individual and then prescribing (recommending or selecting) a lens containing an optical filter wherein if the individual has deuteranomaly then a lens is selected such that the transmittance of the filter at 575 nanometers is at least two times greater than the transmittance at 595 nanometers, and/or if the individual has protanomaly then a lens is selected such that the transmittance of the filter at 595 nanometers is at least two times greater than the transmittance at 575 nanometers, and the luminous transmittance of the filter is greater than about 70%.

In another aspect, a filter for affecting color vision in a desired manner comprises one or more narrow-band dyes, and the filter has a luminous transmittance of at least about 70%, and has a mean transmittance between 390 nanometers and 430 nanometers of at most 25%, and the filter comprises a narrow-band dye having a peak absorption wavelength of about 595 nanometers, and the concentration of the narrow-band dye is configured so that the transmittance of the filter at 595 nanometers is at most about 75%.

In some embodiments, the filter has a luminous transmittance of about 85% and has a mean transmittance between 390 nanometers and 430 nanometers of about 20%.

In some embodiments, the filter has a luminous transmittance of about 75% and has a mean transmittance between 390 nanometers and 430 nanometers of about 5%.

In some embodiments, the filter comprises a first narrow-band absorbing dye having a peak absorption wavelength of about 595 nanometers, and a second narrow-band dye having a peak absorption wavelength of about 405 nanometers, and the second narrow-band dye also has a lesser absorption peak at about 510 nanometers.

In some embodiments, the filter comprises a first narrow-band absorbing dye having a peak absorption wavelength of about 595 nanometers, and a second narrow-band dye having a peak absorption wavelength of about 420 nanometers, and the second narrow-band dye also has a lesser absorption peak at about 525 nanometers.

In another aspect, a filter for affecting color vision in a desired manner comprises one or more narrow-band dyes and one or more blue-absorbing standard dyes, and the filter has a luminous transmittance of at most 40%, and the filter transmittance between 390 nanometers and 425 nanometers is at most 1%.

In some embodiments, the filter transmittance between 390 nanometers and 450 nanometers is at most 1%.

In some embodiments, the filter comprises a narrow-band dye with a peak absorption wavelength of about 595 nanometers, and the concentration of said narrow-band dye is configured so that the transmittance of the filter at 595 nanometers is at most about 10%.

In another aspect, a filter comprising one or more narrow-band dyes and optionally one or more standard dyes, where the filter is configured to affect color vision in a desired manner, is incorporated into an ophthalmic system.

In some embodiments, the ophthalmic system is a type of eyewear comprising an ophthalmic lens and/or window, for example a spectacle lens, sunglass lens or face shield. In some such embodiments the filter may be incorporated so that a portion of the visual field is affected where the portion of the visual field is where near-field viewing conditions occur. In some such embodiments the filter may be incorporated so that a portion of the visual field is affected where the portion of the visual field is where far-field viewing conditions occur.

In some embodiments wherein the ophthalmic system is a type of eyewear, the filter is incorporated into a coating that is applied to the surface of a lens substrate.

In some embodiments wherein the ophthalmic system is a type of eyewear, the filter is incorporated into the bulk material of a lens substrate.

In some embodiments wherein the ophthalmic system is a type of eyewear, the filter is incorporated into both the bulk material of a lens substrate and into a coating that is applied to the surface of the lens substrate.

In some embodiments wherein the ophthalmic system is a type of eyewear, the lens assembly includes a second filter where the second filter is or comprises a photochromic dye, or is or comprises a linear polarizer, or is or comprises a circular polarizer.

In some embodiments the ophthalmic system comprises a contact lens.

In some embodiments the ophthalmic system comprises an intra-ocular lens.

In another aspect, a filter affecting color vision in a desired manner, where the filter comprises one or more narrow-band dyes, is incorporated into an optical system.

In some embodiments, the optical system is a lamp assembly and the filter is incorporated so that some or all of the light emitted by the lamp is filtered.

In some embodiments, the lamp assembly is a flashlight, headlight or similar portable light source.

In some embodiments, the optical system is light bulb, light fixture or similar permanently-installable light source.

BRIEF DESCRIPTION OF THE DRAWINGS

FIG. 22: Scatter plot of luminous transmittance versus red-green separation factor for selected filter examples, and three regions for categorization of colorimetric filter performance.

FIG. 23A: Schematic diagram showing construction of an ophthalmic lens comprising a functional dye-based filter applied as a bonded coating on a lens substrate.

FIG. 23B: Schematic diagram of a lamp source assembly comprising a functional dye-based filter incorporated as an optical window intersecting with the lamp output beam.

FIG. 26: Table of normalized optical density spectra of standard dyes.

FIG. 27: Table of transmittance spectra for DCB series of optical filters.

FIG. 28: Table of transmittance spectra for DCP series of optical filters.

FIG. 29: Table of transmittance spectra for ACE series of optical filters.

FIG. 30: Table of normalized optical density spectra of narrow-band dyes.

FIG. 31: Table of transmittance spectra for DMB series of optical filters.

FIG. 32: Table of transmittance spectra for DMP series of optical filters.

FIG. 33: Table of transmittance spectra for CXB series of optical filters.

FIG. 34: Table of transmittance spectra for CXV series of optical filters.

FIG. 35: Table of transmittance spectra for CXN series of optical filters.

FIG. 36: Table of transmittance spectra for UVH series of optical filters.

FIG. 37: Table of transmittance spectra for ACR series of optical filters.

FIG. 38: Table of properties of filters having $\Psi_{RG}>1$ and $\tau_v>0.40$.

FIG. 39: Table of properties of filters having $\Psi_{RG}<1$.

DETAILED DESCRIPTION

Figure 1:
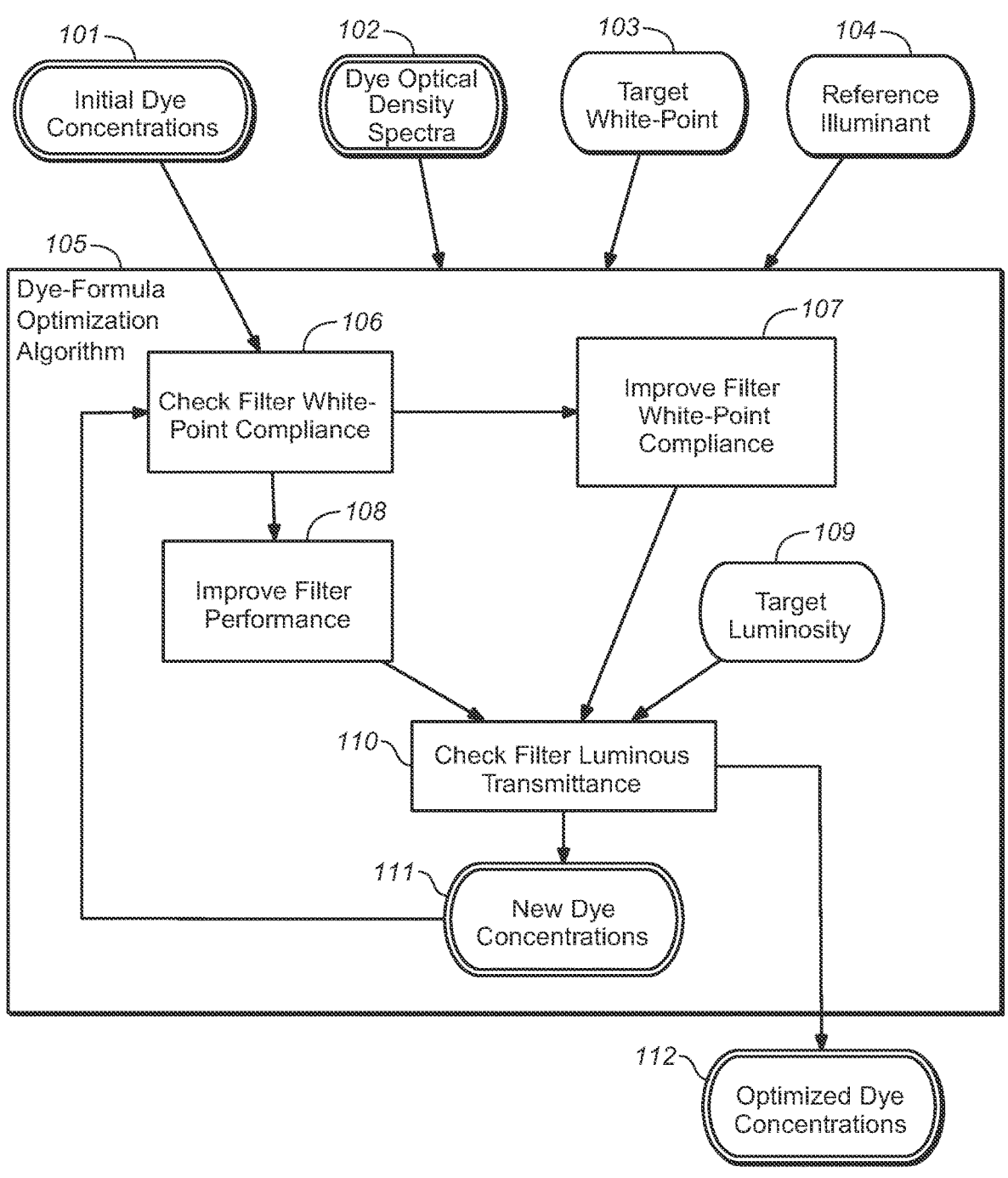
FIG. 1: Process flow diagram depicting iterative method of designing an optimized dye-formula for a filter affecting color vision in a desired manner.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

Optical filters may be incorporated into eyewear to provide a variety of useful effects for assisting with color vision, in particular for providing better color vision to persons with color vision deficiency. As described in U.S. patent application Ser. No. 14/014,991, the relevant design constraints for optical filters affecting color vision in a desired manner are readily stated in the form of a linear program and rapidly solvable with a unique global optimum solution given a cost function. Such constraints include, for example, the chromaticity and/or luminosity bounds required on the appearance of any specified light source as seen through the filter. The constraints of a well-formed (solvable) linear program form a n-dimensional polyhedron where n is the number of basis elements. The basis elements are, for example, mono-chromatic light sources (discrete dirac-delta functions) for each wavelength of light, or may be Gaussian basis functions, or any function of transmittance versus wavelength. Furthermore, a general property of solutions to linear programs is that they are necessarily located at the vertex of the n-dimensional constraining polyhedron. This type of optimality condition is equivalent to the statement that it is always preferable to maximize utilization of a particular basis element (e.g. an element with the least cost), prior to any utilization of a basis element with higher cost. In the absence of any specified constraints on the minimum and maximum spectral transmittance, the optimal filter must have a binary transmittance function per wavelength, meaning that at each wavelength the filter is either 100% transmitting or 100% blocking. In other words, any filter solution that has smoothly changing transmittance function versus wavelength corresponds to linear program solution that is located on the interior of the constraint polyhedron, and therefore is not optimal since it does not minimize cost (or, equivalently, maximize benefit) with respect to the constraining conditions. In the event where constraints are specified, for example governing the minimum necessary luminosity for certain lights, these can lead to regions where the minimum spectral transmittance has a lower bound. For example, the use of such lower bound constraints can result in the appearance of a shoulder feature that extends from a pass-band into an adjacent stop-band. In summary, optimized filters for affecting color vision in a desired manner are those with one or more stop-band (notch) cutouts, and where the absolute magnitude of the slope at each band transition is as high as possible. This characteristic of the band transitions of such filters may also be described as being "sharp", "narrow-band width", "high-frequency", "high attenuation factor" or similar terms.

Means for implementing filters with one or more sharp stop-bands as described include dielectric stacks (equivalent to an optical infinite impulse response filter), polarization retarder stacks (equivalent to an optical finite impulse response filter), absorptive dyes, fluorescent dyes, and hybrid approaches comprising two or more of the aforementioned means. Dielectric stacks and polarization retarder stacks can both be considered types of general filter design technologies, in that they are capable of being adapted to nearly arbitrary target filter specifications. Such technologies are appropriate for use with the design method based on linear programming described above. However, for the design of filters based on combinations of dyes, it may be preferable to use a different method that is preferable for determining the appropriate dye-formula using an iterative algorithm that accommodates the non-linear mixing properties of dyes. The properties of dyes are inherently non-linear (being characterized according to the Beer-Lambert law), and therefore are not suitable as inputs to a linear program solver. In addition, design of dye-based filters poses additional problems including: 1) dyes are limited to discrete choices due to underlying chemistry, and the optical density spectrum of dyes available for formulation may not be readily modified. 2) the spectral absorptance of dyes, e.g. in a polymeric carrier matrix, are not ideally selective and often have side-bands or otherwise cause absorption in disparate areas of the spectrum, 3) dyes impart coloration to filters which may have aesthetic consequences (in particular when incorporated into eyewear). Given a theoretically optimal target transmittance spectrum (e.g. as calculated by the method of linear programming), it may be difficult to find a combination of dyes that approximates the target accurately while also providing adequate performance with respect to the desired effect on color vision. In addition, for filters that comprise a complex formula of two or more dye components, the filter properties change under any scalar modification of the formula. For example, suppose a dye formula is diluted in equal proportion over its dye components to arrive at a new filter with a higher luminous transmittance. The diluted filter will be less optimal than a filter that is designed (e.g. using the method described below) to have the same target luminous transmittance as the diluted filter.

An iterative method for designing and optimizing filters that affect color vision in a desired manner, where the filters are based on combinations of dyes (specified using a dye-formula), is described in detail below. This method, when implemented on a computer, enables automatic optimization of a dye-formula for filter affecting color vision in a desired manner. The dye-formulas provided by this method can be used as the basis for a manufacturing specification of such filters. Examples of filters designed using this method and/or variations of the method, the filters' desired effects on color vision, and other detailed descriptions are provided along with description of FIGS. 14-20. The method, as described herein, is capable of producing dye-formulas for filters that are optimized with respect to a colorimetric performance metric, while also satisfying one or more constraints, e.g. constraints on the chromaticity and/or luminosity of certain specified light sources. In some variants of the method the colorimetric performance metric is defined as the red-green separation factor, which is defined and described in detail below. In some variants the colorimetric performance metric is the chromaticity gamut area of a set of specified reference colors. In some variants the colorimetric performance metric is the minimization of transmission of high-energy visible light (i.e. short-wavelength blue light). In some variants the colorimetric constraints pertain to the luminosity and/or chromaticity of a specified white light, for example, by requiring that the Standard Illuminant D65 has a particular luminosity and its chromaticity (as viewed through the filter) is bounded within a particular region in chromaticity space. In some variants the colorimetric constraints pertain to the luminosity of a specified yellow light, for example by requiring that yellow LEDs have a minimum luminosity necessary to enable visibility of such lights when viewed through the filter. In some variants the colorimetric constraints pertain to the limitation of scotopic transmittance to be a fraction of the luminous transmittance, for example less than about one third (scotopic light is light that is received by the rod cell photo pigment comprising wavelengths between about 430 nanometers and about 570 nanometers).

FIG. 1 is a process flow diagram depicting an embodiment of the aforementioned iterative method (algorithm) of optimizing a dye-formula for a filter given a specification of design criteria. The design criteria shown include a vector of the initial dye concentrations 101, the optical density spectra of dyes available for formulation (component dyes) 102, the target white-point of the filter 103 (e.g. the desired CIE 1931 (x,y) chromaticity coordinates of a reference illuminant), and the power spectrum of the reference illuminant 104. Typically the reference illuminant is CIE Standard Illuminant D65, but may also be another illuminant such as that of a different phase of daylight, or a fluorescent lamp, or of a light-emitting diode, or any other specified light source. The design criteria are provided as inputs to the dye formula optimization algorithm 105, within which an iterated process takes place, wherein an initial set of dye concentrations is iteratively updated until the process is terminated, and the state of the dye concentrations upon termination is a set of optimized dye concentrations 112.

The iteration process is initialized by simulating a filter using the initial dye concentrations and the component dye optical density spectra. Typically the initial dye concentrations are all zero, i.e. the initially simulated filter is fully transparent. The simulated filter is then checked with respect to the specified white-point constraints. The white-point of the filter is calculated in terms of a two-dimensional chromaticity coordinate in a suitable color space, for example CIE Yxy or CIE LUV color space. The white-point constraint check comprises measuring the distance between the target white-point 103 and the white-point provided by the currently simulated filter with respect to the reference illuminant. If the target white-point is a single point, then the distance is a vector length. If the target white-point is a 2-dimensional region, then the distance is the length of the shortest line connecting the currently provided white-point to the boundary of the region, or zero for points located on the boundary of the region or located within the region. The filter white-point check is considered to pass (i.e., is in compliance) if the distance value is less than an appropriately chosen epsilon, for example about 0.001 units in the CIE (x,y) chromaticity space. In some variations a larger epsilon value (e.g. 0.05 units in the CIE (x,y) chromaticity space) may be chosen, where the use of a larger epsilon value is equivalent to defining a circular, curved or rounded target white-point region. If the filter white-point check is considered to pass, then a sub-process is performed wherein improvements to the colorimetric performance of the filter are considered 108. If the check is considered to not pass (i.e. is not in compliance), then a sub-process is performed wherein improvements to the filter white-point compliance are considered 107. The two aforementioned sub-processes 107 108 analyze the current dye-formula and then select a new dye-formula that corresponds to a new simulated filter. These data are then provided to another sub-process where the luminous transmittance of the filter is measured 110. If the luminous transmittance is less than or equal to the target luminosity 109, then the dye-formula optimization process is terminated and the current dye concentrations are output as the final optimized dye-formula 112. If the luminous transmittance is greater than the target luminosity, then the dye concentration vector 111 is updated and the process flow as just described is repeated by returning to the filter white-point check step indicated at 106.

Each time the process loop shown is executed, the concentration of one of the dyes is increased, causing a non-linear transformation to the currently simulated filter. As the concentrations are monotonically increasing with each iteration, the luminosity of the filter will be lesser with each iteration, eventually resulting in the termination of the process when the filter reaches the desired target luminosity. In each iteration, the amount of change in dye concentration amounts to a small discrete step, which, over time approximate a continuous line in an n-dimensional space where n is the number of dye optical density spectra 102 provided from the set of dyes available for formulation. The optimality of the resulting filter is a consequence of the optimality of the each step along this line. The method of choosing the optimal step in each of the sub-processes 106 and 107 is described in further detail below.

Figure 2:
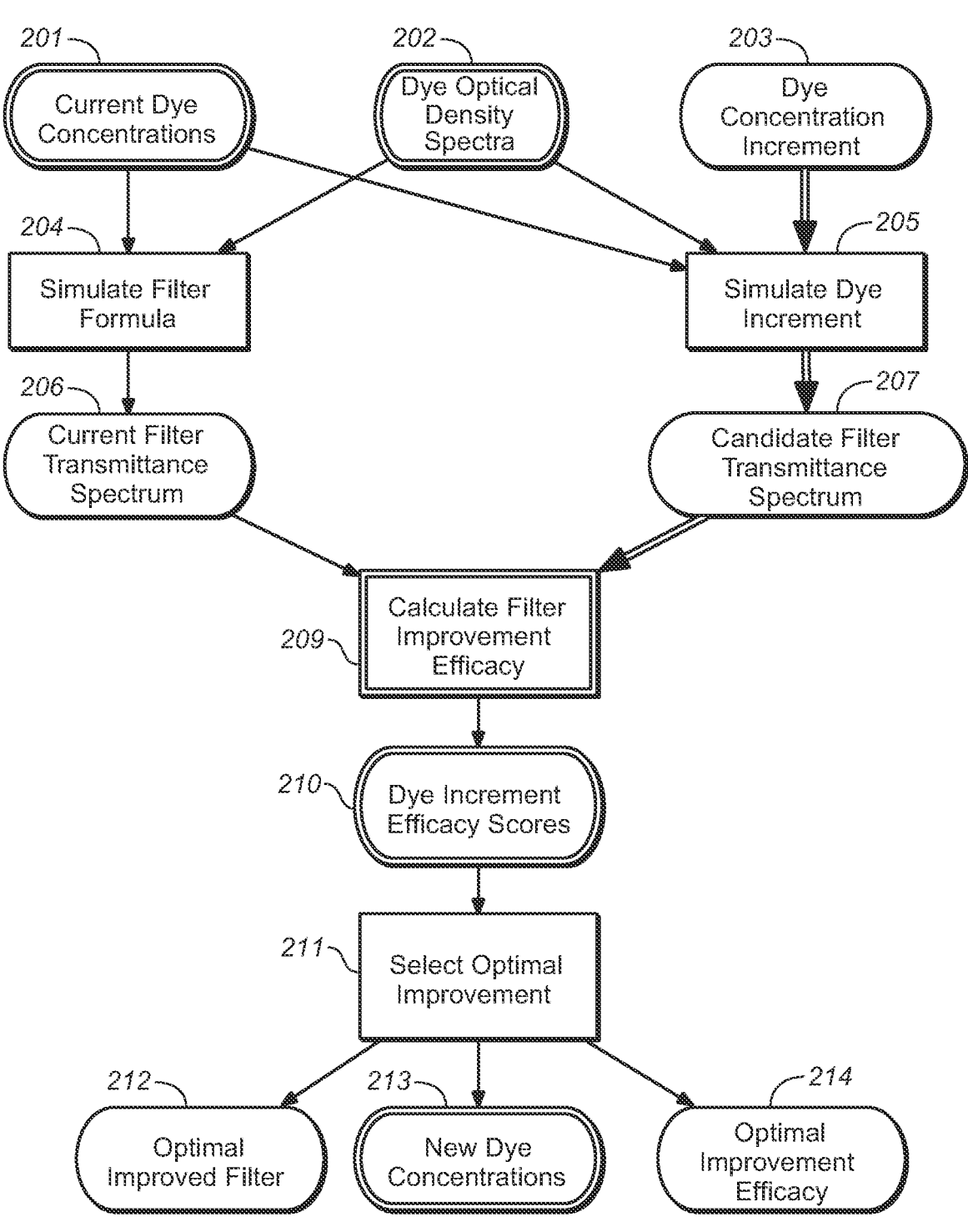
FIG. 2: Process flow diagram depicting method of measuring candidate improvements to a dye-formula for a filter affecting color vision in a desired manner.

The sub-processes 106 and 107 in FIG. 1 both consider possible improvements to a dye-formula, and utilize a common algorithmic structure for simulating the possible improvements, then measuring the efficacy of the candidate improved filters, and then selecting the best improvement available from the candidate options. A description of this general process is depicted in FIG. 2. The sub-processes 106 and 107 correspond to two variations of this general process, where different types of improvements are considered. The calculation of efficacy for the different types of improvements are explained below along with descriptions of FIG. 3 and FIG. 4.

Referring now to FIG. 2, the method of selecting the optimal improvement to a dye-formula given a set of candidate improvements, is depicted as a process flow diagram. Herein the process is initialized from the current set of dye concentrations 201, the set of optical density spectra of dyes available for formulation 202, and the current simulated filter corresponding to the mixture of the component dyes in their corresponding concentrations according to the dye formula 204, the transmittance spectrum of the current filter 206, and a set of dye concentration increments 203 consisting of a dye increment corresponding to each dye. The dye concentration increments are a small amount by which the concentration of a corresponding dye will be increased. For example, by increasing the total concentration by about 0.001 units. The small dye increment values, when considered over time, approximate a continuous change in concentration for each dye. The increment size must be selected appropriately to produce a good approximation of continuity, otherwise the algorithm could result in a non-optimal solution. For each dye concentration increment, a filter is simulated 205 corresponding to the current dye-formula where the concentration of the corresponding dye has been increased accordingly, resulting in a collection of transmittance spectra of candidate filters 207. For each candidate filter corresponding to a dye increment, the improvement efficacy with respect to the dye increment is calculated 209, which involves a comparison between the candidate filter and the current filter 206. The dye increment efficacy scores are then collected 210 and then sorted to choose the dye increment with the best performance 211 resulting in an updated and optimally improved filter 212, and a new set of dye concentrations corresponding to the improved filter 213, and the efficacy score corresponding to the dye increment that was chosen as optimal 214. The new dye concentrations are then returned to the enclosing routine which is described above along with FIG. 1. In addition, the efficacy score 214 can be monitored at each step to obtain insight into the amount of improvement being achieved as the enclosing iterative design method executes.

Figure 3:
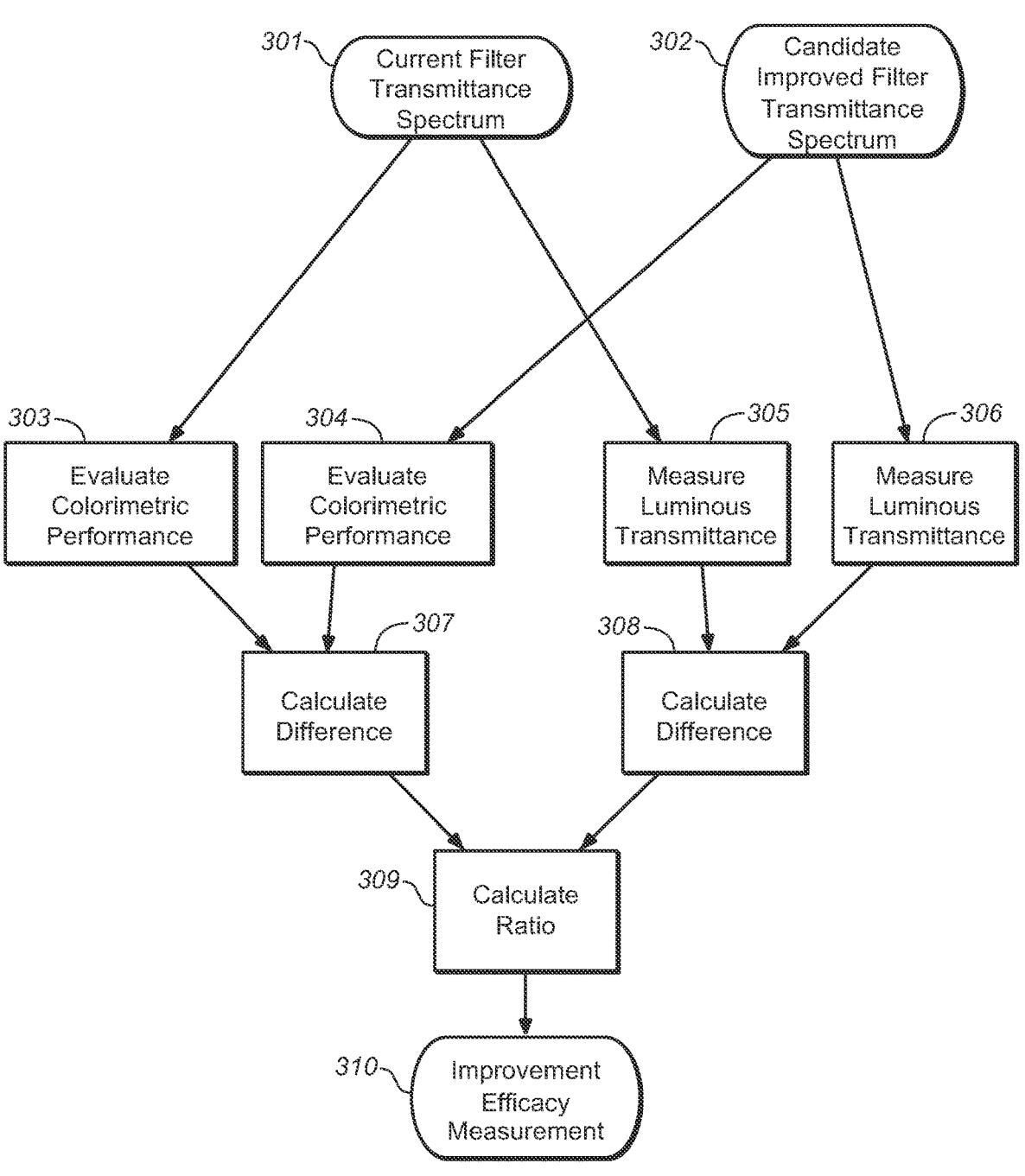
FIG. 3: Process flow diagram depicting method of measuring improvement for a candidate improved filter where the improvement desired is to increase a colorimetric performance metric.

The calculation of a candidate improved filter 302 as compared to the current filter 301, with respect to a colorimetric performance measure, is depicted in FIG. 3. The calculation is initialized by evaluating the colorimetric performance for both the current filter 303 and for the candidate filter 304, and by calculating the luminous transmittance of the current filter 305 and of the candidate filter 306. Then, the amount of change in both quantities is calculated, providing the amount of change in colorimetric performance between the current and candidate filters 307, and the amount of decrease in luminosity between the current and candidate filters 308. Note that the candidate filter always has a lower luminous transmittance than the current filter, however the colorimetric performance may be either greater or lesser depending on which dye concentration was incremented in the formulation of the candidate filter. The two differences are then compared as a ratio 309 giving the rate of change in colorimetric performance per change in luminous transmittance, which can be understood as a measure of the improvement efficacy of the corresponding dye increment 310 with respect to the colorimetric performance.

In the above calculation it may be useful to understand that, given a current dye formula and corresponding filter, and the set of dyes available for formulation, it is desired to increase the concentration of the dye that is most effective toward improving the colorimetric performance, however the total amount of dye that can be "loaded" into a formula is limited by the target luminosity of the filter. Therefore, the dye that maximally increases the colorimetric performance may not be the optimal dye to increase in concentration if it also has a high cost in terms of how much it decreases the filter luminosity. If we consider available luminosity as a resource that is spent/cost that is incurred by increasing dye concentration, then the optimal dye to increase is the one that gives the best cost:benefit ratio between the luminosity and the colorimetric performance. The calculation of FIG. 3 as described above can be understood as a calculation of that cost:benefit ratio.

In another variation of the method of designing optimal filters from a dye concentration formula, the size of the dye increments can be varied for each dye, so that at each step the change in luminosity is held constant for all filter candidates.

The selection of appropriate colorimetric performance measures for affecting color vision in a desired manner is described in further detail below along with examples of filters designed accordingly.

Figure 4:
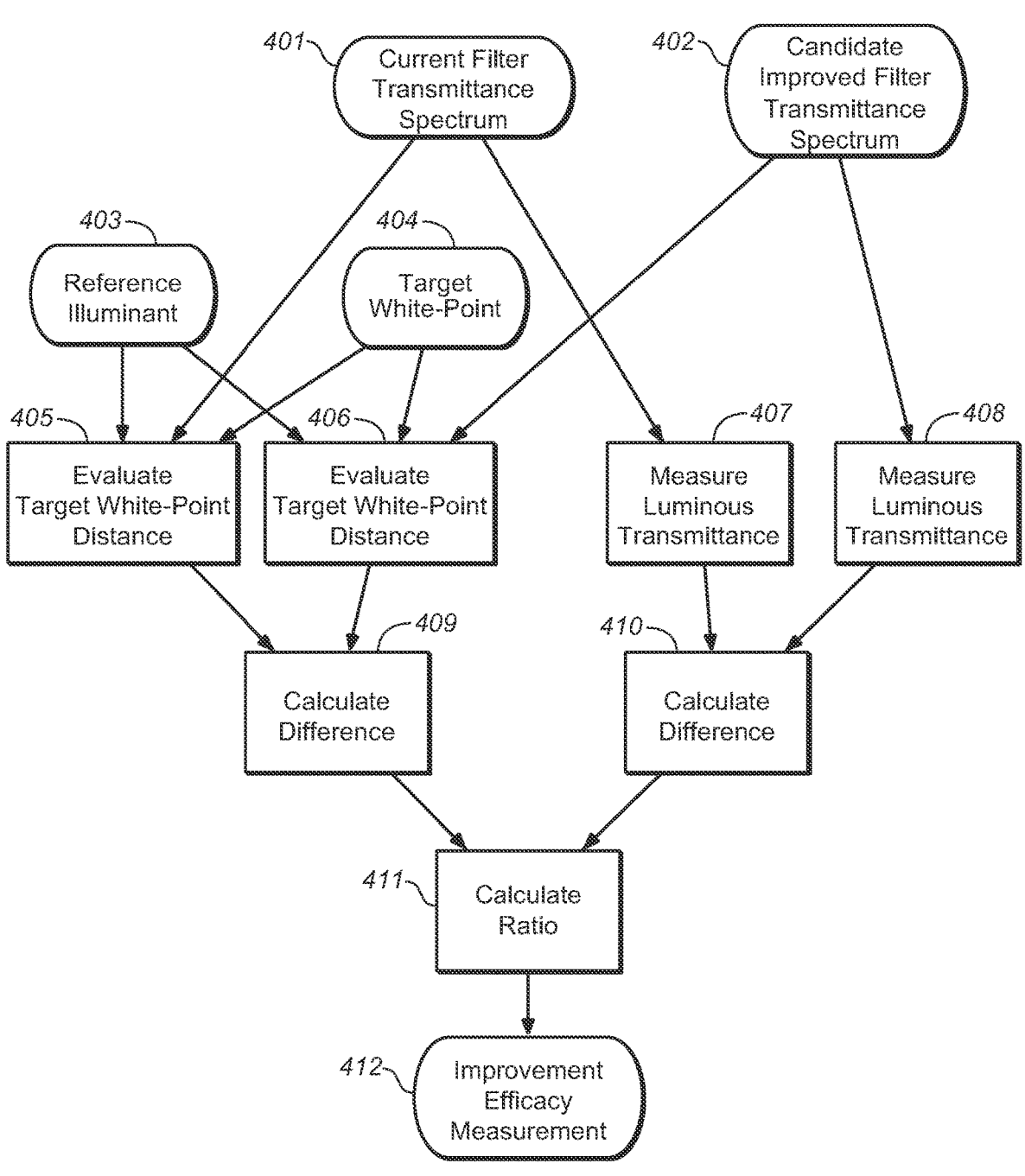
FIG. 4: Process flow diagram depicting method of measuring improvement for a candidate improved filter where the improvement desired is to restore compliance with a target white-point constraint.

Another calculation concerning evaluation of candidate improvements to a dye formula is depicted in FIG. 4, wherein the objective is to determine the improvement efficacy with respect to restoring compliance of the current filter with the target white-point constraint. In this calculation, the transmittance spectrum of the current filter 401 is evaluated to determine its distance to the target white-point 405, and its luminous transmittance 407. The candidate improved filter 402 is evaluated according to the same at 406 and 408. The distance to the target white-point is defined with respect to the target white-point 404, which may be a chromaticity coordinate, or a region in chromaticity space as described previously, and with respect to the reference illuminant 403, also described previously. The target white-point distance and luminosity values are then compared in a difference operation at 409 and 410, respectively, and then input into a ratio calculation at 411 to determine an overall measure of improvement for the candidate filter with respect to the white-point constraint criteria.

The basic properties of the calculation just described is similar to that of FIG. 3, wherein the goal is to determine the cost:benefit ratio of the dye increment corresponding to the candidate filter. However in the calculation depicted by FIG. 4, the dye with greatest efficacy is the one that reduces the target white-point distance with the least reduction in filter luminosity. In other words, it is desired to restore the white-point to compliance without making the filter unnecessarily dark.

In another variation of the above calculation, the luminosity calculation at 407 and 408 is replaced with a colorimetric performance measure, as in FIG. 3 at 303 and 304. In this variation the filter candidate with maximum efficacy is the one that restores white-point compliance with the least reduction in colorimetric performance.

The iterative method depicted in FIG. 1 can now be understood, together with the details of the sub-processes defined by FIG. 2, FIG. 3 and FIG. 4, as a detailed description of the method by which filters intended to affect color vision in a desired manner can be designed as formulations of dye concentrations from a set of available dyes.

In one variation of the iterative method, the iterations proceed substantially as described above, wherein at each step the process considers improvements to either the target white-point constraint compliance or to the desired colorimetric performance. For sufficiently small dye increment values this method may be adequate, however in some cases a higher-order version of the iterative process may be preferred. In such a variant, the repetitions of the process are recursively calculated, in order to simulate the optimality of a filter candidate after several steps according to different dye increment selections, and then selecting the dye increment corresponding to the optimal choice considering this larger set of candidates. The depth of recursive calculation possible is limited by available computing resources (e.g. processor time and memory). In another variation the dye increments may be considered that induce a change in more than one dye component, i.e., the "step direction" is not limited to movements in only one axis of the n-dimensional solution space.

Additional variations of the process, which are configured to result in filters that are preferable for certain applications, are described in detail along with additional figures below.

Filters that affect color vision in useful ways, when integrated into an optical system, provide a spectral transmittance that modifies the power spectrum of light passing through the system. Such filters, given a suitable means of manufacturing, may be incorporated into eyewear or into contact lenses, for example, to transform the image received by the eye. Such filters may also be incorporated into lamp assemblies to transform the light used to illuminate a working area.

Figure 5:
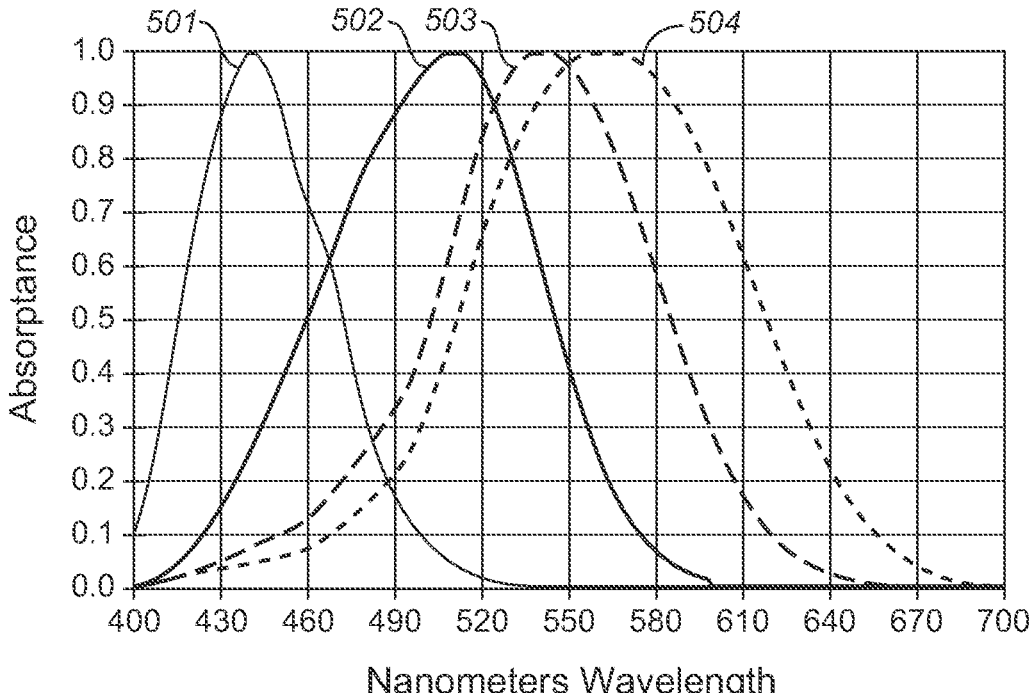
FIG. 5: Absorptance spectra of the S-cone, M-cone, L-cone and rod photo pigments for a typical human eye.

The nature of human color vision is based on the spectral sensitivity of photoreceptors in the eye, each of which respond broadly to a particular sub-band of light within the visible spectrum. The normalized absorptance of the photoreceptor pigments are shown in the graph of FIG. 5, wherein the S-cone absorptance 501 has a peak absorptance at about 440 nanometers, the M-cone absorptance 503 has a peak absorptance at about 540 nanometers, the L-cone absorptance 504 has a peak absorptance at about 565 nanometers, and the rod cell absorptance has a peak absorptance 502 at about 510 nanometers. The perception of color in humans is formed by comparing the relative stimulation of neighboring photoreceptors of the three different types which are packed together in a mosaic of 6-7 million photoreceptor cells on the surface of the retina.

The space of all possible visible power spectra is an infinite dimensional vector space, which is projected onto a 3 dimensional space of perceived color and lightness. The projection is described as the mathematical concept of a Hilbert space. Humans with normal color vision are able to distinguish approximately 1 million unique shades of color. Different spectral stimuli that induce the same color sensation are called metamers. Vision based on three distinct cone classes is called trichromatic color vision. The 3 dimensional space of apparent color can be decomposed into three channels which are essentially orthogonal percepts: that of lightness or brightness (spanning from white to black), and two channels of chromaticity comprising the blue-yellow channel (organizing color percepts by their blue-ness to yellow-ness) and the red-green channel (organizing color percepts by their red-ness to green-ness). The blue-yellow channel corresponds to the comparison of the S-cone stimulation versus the combined M-cone and L-cone stimulation. The red-green channel corresponds to the comparison of the M-cone stimulation to that of the L-cone stimulation. Vision from stimulation of the cone cells is referred to as photopic vision, and vision from stimulation of the rod cells is scotopic vision. Rod-cell photoreceptors are overwhelmed (bleached) by bright light, and thus scotopic vision, which is a monochromatic visual mechanism, is only active at night time and/or in very low-light conditions. Activities such as driving a car at night are actually performed using photopic vision, due to the brightness of car headlights and traffic signal lights.

It is observable from the graphs of photoreceptor absorptance in FIG. 5 that there is substantial overlap between the absorptance curves, in particular of the M-cone and L-cone. Furthermore, in the human population there are genetic variations causing the spectral position of the M-cone and L-cone to vary between individuals. Persons with increased overlap between the M-cone and L-cone absorptance are called red-green color blind, although it is more technically correct to refer to this condition as color vision deficiency (CVD). CVD is classified according to type (either an anomaly of the M-cone (deuteranomaly) or of the L-cone (protanomaly)) and according to the extent (corresponding to the amount of increased overlap, which can be mild, moderate, severe or total). For cases of CVD where the overlap is less than total, trichromatic vision is still functional, although may be significantly impaired. For a mild impairment the number of perceivable colors may drop to 100 thousand (10% of normal), while for a strong individual it may be as low as 10 thousand (1% of normal). Filters disclosed herein are generally found to be useful for enhancement of trichromatic vision, including that of normal trichromatic vision, as well as for most cases of anomalous trichromatic vision. The fundamental mechanism of how these filters modify color vision is that they selectively block light with wavelengths corresponding to locations where significant amount of overlap between the photopigment absorptance curves is found. In addition to red-green color blindness, other types of anomalous trichromatic vision include tritanomaly (a condition where S-cone function is deficient), general loss of chromatic sensitivity (a condition often experienced with low-vision complications such as retinitis pigmentosa and glaucoma), and incomplete achromatopsia (a condition related to severe dysfunction or nearly total lack of cone cells, but having functional rod cells, sometimes also called "day-blindness").

For the purpose of designing filters that assist with red-green color blindness, and in particular for filters that also have a high luminous transmittance, a colorimetric performance metric is provided herein that is easy to calculate. The metric is referred to herein as the red-green separation factor, which is also denoted $\Psi_{RG}$ in this disclosure. Given the transmittance spectrum of a filter, $\tau(\lambda)$, the calculation of red-green separation factor is given according to the formula:

$$\Psi_{RG} = ((\tau_v \times ((((\tau_G + \tau_R)/2)/\tau_Y) - 1))/(1 - \tau_v) + 1)$$

Wherein, in the above formula, $\tau_v$ is the luminous transmittance of the filter, $\tau_G$ is the average spectral transmittance of the filter between 500 nanometers and 550 nanometers, $\tau_Y$ is the average spectral transmittance of the filter between 555 nanometers and 600 nanometers, $\tau_R$ is the average spectral transmittance of the filter between 600 nanometers and 650 nanometers. The use of the red-green separation factor as a colorimetric performance measure has been found by the inventors to be preferable for use with the disclosed iterative filter design method when the target luminosity of the filter is greater than about 40%. For target luminosity of less than 40%, other colorimetric performance measures, such as the chromaticity gamut area of a set of reference colors (as described in U.S. patent application Ser. No. 14/014,991), may be preferable.

Figure 6:
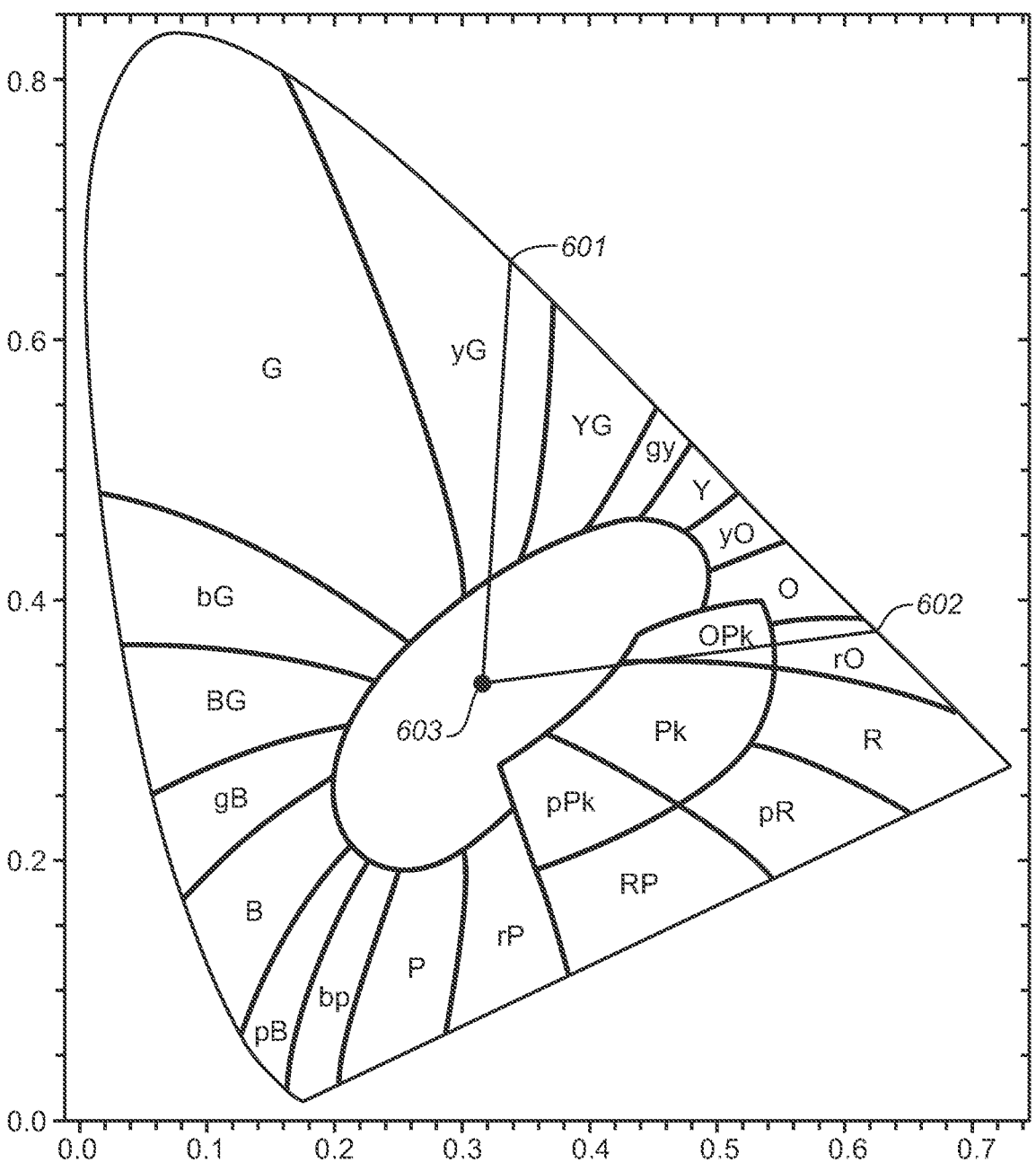
FIG. 6: Chromaticity diagram showing regions having canonical color names, and a triangular region comprising intermediate colors between green and red.

The chromaticity diagram shown in FIG. 6 includes a plurality of regions which are labeled using an alphanumeric code according to their canonical color name. Filters that have a high red-green separation factor are characterized by a stop-band or general inhibition of transmittance over wavelengths of light corresponding to spectral colors considered to be between red (R) and green (G). Spectral colors are the apparent perceived color of a monochromatic light, which correspond to chromaticity coordinates located on the spectral locus in a chromaticity diagram. A monochromatic light having a wavelength of about 580 nanometers is considered yellow (Y), and at wavelengths between 555 to 580 nanometers are considered (gY) greenish-yellow, (yG) yellowish-green, or (YG) yellow-green, and at wavelengths between 590 to 610 nanometers is considered to be yellowish-orange (yO), orange (O) reddish-orange (rO). These regions taken together approximately span the intermediate colors between red and green, and a filter inhibiting the transmission of these wavelengths will tend to amplify the apparent saturation of red and green colors as typically observed in the man-made and natural environment. The location on the chromaticity locus of the color of monochromatic light with wavelength 555 nanometers is indicated at 601, and the location on the chromaticity locus of the color of monochromatic light with wavelength 600 nanometers is indicated at 602. The point on the chromaticity diagram corresponding to Standard Illuminant D65 is indicated at 603. The straight lines connecting 603 to 601 and 603 to 602 define the distance from these monochromatic color coordinates to the specified white-point.

Figure 7:
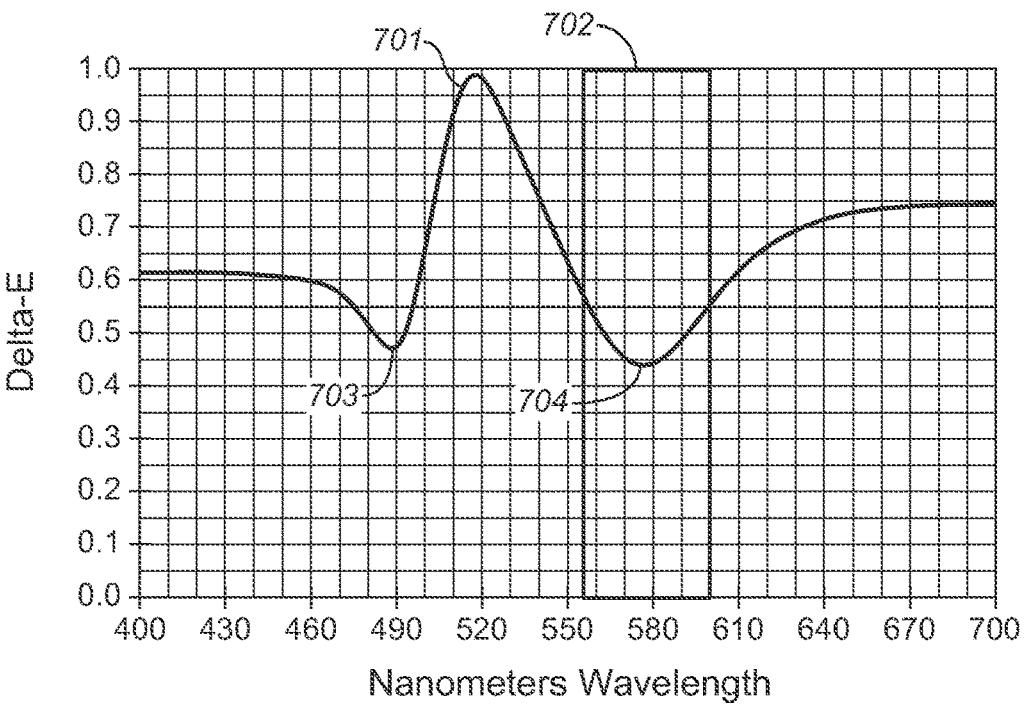
FIG. 7: Graph of the distance between the white-point and the spectral locus per wavelength, and a rectangular region denoting the wavelengths corresponding to spectral colors between green and red.

The plot of FIG. 7 gives a graph 701 of the distance from the chromaticity locus to the specified white-point, per wavelength. On this graph two minima may be noted at 703 and 704, corresponding to monochromatic light which are considered cyan and yellow, respectively. Of all the monochromatic lights, cyan and yellow are considered the "most similar" to white, and therefore can be expected to have the smallest distance to white in any color space where distance is proportional or approximately proportional to perceived difference in color. On this plot, the region at 702 denotes the sub-band of light between about 555 nanometers and about 600 nanometers, as previously described.

Figure 8:
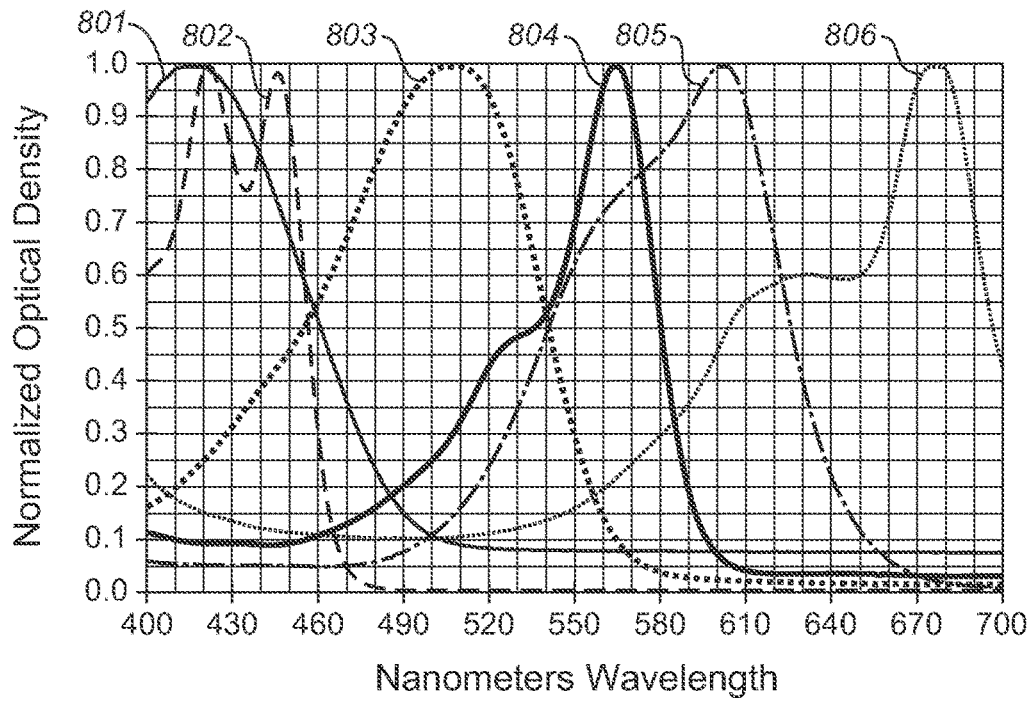
FIG. 8: Optical density spectra of selected standard dyes.

The optical density spectra of a set of standard dyes are plotted in FIG. 8. The term "standard dyes" herein refers to dye compounds that are commonly used in absorptive ophthalmic lenses (e.g. sunglass lenses and other colored lenses), and is technically defined for the purposes of the present disclosure as any dye having a full-width-half-maximum (FWHM) width of greater than about 40 nanometers, as exemplified by the dye optical density spectra in FIG. 8 which all satisfy this property. In the present disclosure the optical density spectra data are normalized to a maximum value of 1.0 at the wavelength of peak absorptance. Conversion from normalized optical density to units of physical concentration (e.g. parts per million per millimeter) can be readily performed by multiplication of the data by a linear scaling factor. Such conversion depends on the dye strength, which may be obtained by simple experimentation or in many cases directly from the manufacturer's dye data sheet.

The standard dyes described herein are based on chemical pigments (including but not limited to anthraquinone, perinone, diazo, monoazo, rhodamine and others). The dyes can be obtained commercially from Keystone Aniline Corporation of Chicago IL under the Keyplast™ brand, and can be incorporated into optical filters and/or ophthalmic lenses by a variety of methods including casting (e.g. cast acrylic), injection molding (e.g. using polycarbonate), or coating (e.g. polyurethane or acrylic coatings applied by a spin-on or dip process). Another process by which dye pigments can be incorporated into an ophthalmic lens involves immersion of the lens in a heated bath of fluid and pigment, wherein by diffusion the dye pigment molecules become embedded into the porous surface of a tintable hard-coat. The process is sometimes used in ophthalmic processing labs to produce low-manufacturing volume custom-tinted lens products. The resulting tints provide transmittance spectra substantially similar to the standard dyes described herein, and are commercially available from Phantom Research Laboratories of San Diego, CA under the Opti-Safe™ brand, in addition to other vendors. Commercial providers of standard dyes also provide pre-mixed combinations (blends) of standard dyes to form common colors. For example the color black requires a blend of several standard dyes to create a good approximation to the ideal neutral density filter.

In the present disclosure standard dyes are also comprehended to include photochromic dyes, which are also available in a wide range of colors and have similar broadband spectral transmittance properties (e.g. the Reversacol™ brand of photochromic dyes which is manufactured by Vivimed Labs Ltd. and distributed by Keystone Aniline Corporation). The behavior of photochromic dyes is time-varying depending on the amount of ambient UV radiation, however such changes can be reasonably approximated by analyzing the filter properties in two states: a first state where the photochromic dye is not activated (i.e. the faded state), and a second state where it is activated according to average daylight (i.e. the exposed state), wherein a method of measuring the exposed state and faded state of a lens comprising photochromic dyes is given by ANSI Z80.3-2010 section 5.7.

Referring again to FIG. 8, the optical density spectrum indicated at 801 corresponds to a blue-absorbing dye, referred to as SD415Y in the present disclosure. The optical density spectrum indicated at 802 corresponds to a blue-absorbing dye referred to as SD435Y in the present disclosure, and is commercially available under the brand name Keyplast™ Yellow YC. The optical density spectrum indicated at 803 corresponds to a blue-green absorbing dye referred to as SD510R in the present disclosure, and is commercially available under the brand name Keyplast™ Orange LFP. The optical density spectrum indicated at 804 corresponds to a yellow-green absorbing dye referred to as SD565P in the present disclosure. The optical density spectrum indicated at 805 corresponds to that of a yellow-absorbing dye referred to as SD600V in the present disclosure. The optical density spectrum indicated at 806 corresponds to that of a red-absorbing dye referred to as SD675B in the present disclosure. Dyes absorbing a particular color (e.g. yellow), when added to an optical system cause the white-point to shift toward an opposing chromatic color (e.g. toward blue). The normalized optical density of the aforementioned dyes are tabulated in FIG. 26 using 5 nanometer intervals between 400 nanometers and 700 nanometers. The wavelengths appear in the row under the heading "nm", and the dye optical density spectra under the headings enumerated above (e.g. SD415Y, etc.).

Examples of filters based on combinations of standard dyes that increase the red-green separation factor ($\Psi_{RG}$) are described below along with FIG. 9 and FIG. 10. These examples were also selected to demonstrate the attainable limits on $\Psi_{RG}$ in combination with target luminosity ($\tau_v$) of greater than about 40%.

Figure 9:
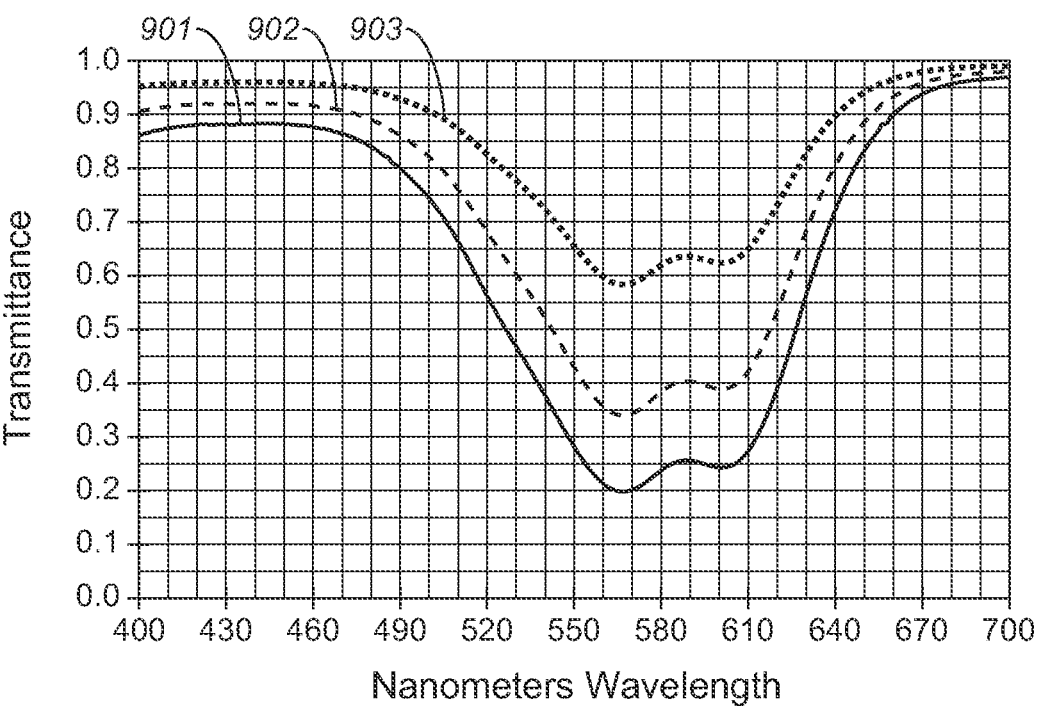
FIG. 9: Transmittance spectra of blue-colored filters comprising standard yellow-absorbing dyes.

The transmittance spectra for a series of filters (referred to collectively as the DCB series) are plotted in FIG. 9. The graph at 901 corresponds to a filter with a luminous transmittance of about 40% and is referred to as DCB40 in the present disclosure. Referring to the set of standard dyes previously described, and their optical densities provided in the table of FIG. 26, a dye formula for DCB40 can be expressed as the formula:

$$DCB40 = 0.252 \times SD565P + 0.599 \times SD600V$$

Wherein, in the above formula, the numbers 0.252 and 0.599 correspond to concentrations of the dyes, and SD565P and SD600V correspond to the normalized optical density spectra included in this formula (tabulated in FIG. 26), and the code DCB40 corresponds to the mixture comprising the component dyes in the given proportions, wherein the units of the vector DCB40 are optical density and the transmittance of an optical system comprising a filter composed of the given dye mixture is given by the formula:

$$\tau_{DCB40} = 10^{(-1.0 \times DCB40)}$$

Returning to FIG. 9, the graph at 902 corresponds to a filter with about 55% luminous transmittance and is referred to as DCB55 in the present disclosure, and has the dye formula:

$$DCB55 = 0.168 \times SD565P + 0.399 \times SD600V$$

The graph at 903 corresponds to a filter with about 70% luminous transmittance and is referred to as DCB70 in the present disclosure, and has the dye formula:

$$DCB70 = 0.0839 \times SD565P + 0.2 \times SD600V$$

The DCB series of filters have a blue color (i.e. impart a blue-tint to white light passing through the filter), and provide a red-green separation factor between 0.7 and 0.8. Filters such as these generally may be used to color ophthalmic lenses for aesthetic purposes, but the colorimetric performance with respect to enhancement of red and green colors is not significant. Transmittance spectra of the DCB series of filters are provided in 5-nanometer (nm) steps in the table of FIG. 27.

Figure 10:
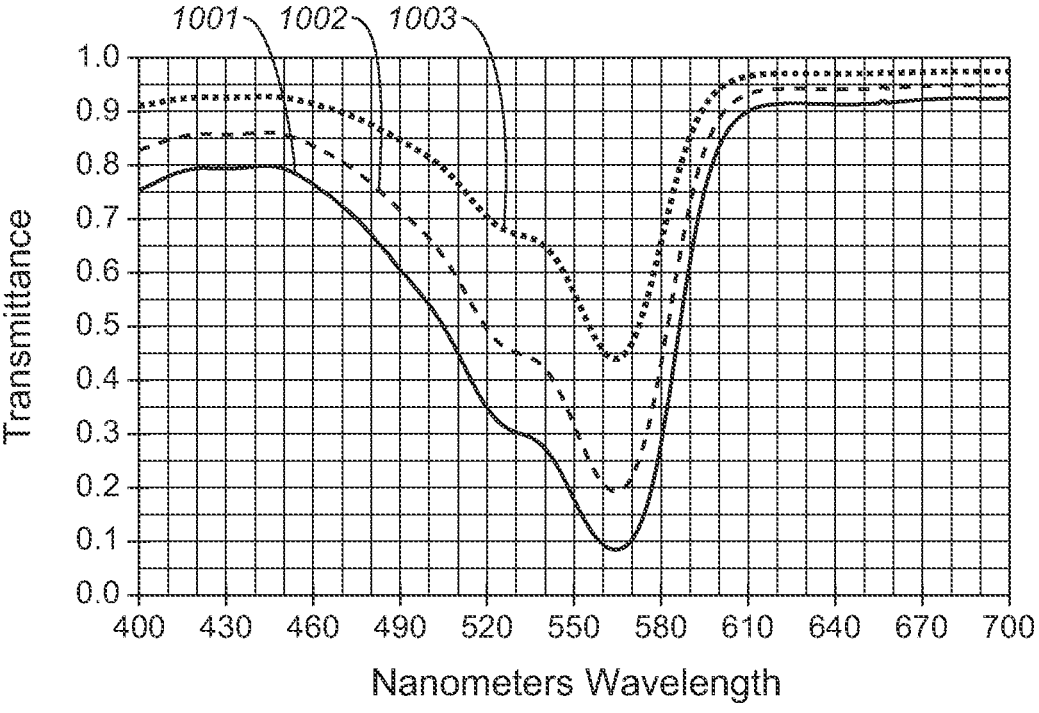
FIG. 10: Transmittance spectra of pink-colored filters comprising standard yellow-absorbing dyes.

The transmittance spectra for another series of filters, referred to collectively as the DCP series, are plotted in FIG. 10. These filters have a pink-ish white point (i.e. impart a pink, reddish or purple-ish color to white light passing through the filter). These filters provide red-green separation factors between 0.6 and 0.7. Filters with transmittance curves similar to those depicted here may be marketed as optical aids for color vision deficiency. The pink-ish color of such filters tends to disrupt the pseudo-isochromatic requirements in the design of vanishing-plate style color blindness screening tests (e.g. the Ishihara plate test, HRR plate test, etc.), however in practical use applications they are often found to be either too dark, and/or not effective enough.

Referring again to FIG. 10, the graph at 1001 corresponds to the transmittance spectrum of a filter with about 40% luminous transmittance and is referred to as DCP40 in the present disclosure, and has the dye formula:

$$DCP40 = 1.07 \times SD565P$$

The graph at 1002 corresponds to the transmittance spectrum of a filter with about 55% luminous transmittance and is referred to as DCP55 in the present disclosure, and has the dye formula:

$$DCP55=0.713 \times SD565P$$

The graph at 1003 corresponds to the transmittance spectrum of a filter with about 55% luminous transmittance and is referred to as DCP70 in the present disclosure, and has the dye formula:

$$DCP70=0.357 \times SD565P$$

Transmittance spectra of the DCP series of filters are tabulated in 5-nanometer (nm) steps in the table of FIG. 28.

The low performance of the DCB and DCP series filters provided above (which is quantifiable by noting their red-green separation factors less than 1.0) is a consequence of their component dyes, which are standard dyes having relatively broad spectral absorptance curves. Filters that are preferable for increasing red-green color separation, and thereby potentially assisting an individual with some form of red-green color blindness, should have a red-green separation factor that is greater than 1.0, or more preferably greater than 1.25, or more preferably greater than 1.5. The broadband absorptance of standard dyes result in filters with poor spectral selectivity. To provide filers with preferable red-green separation factors requires the use of non-standard optical materials.

Figure 11:
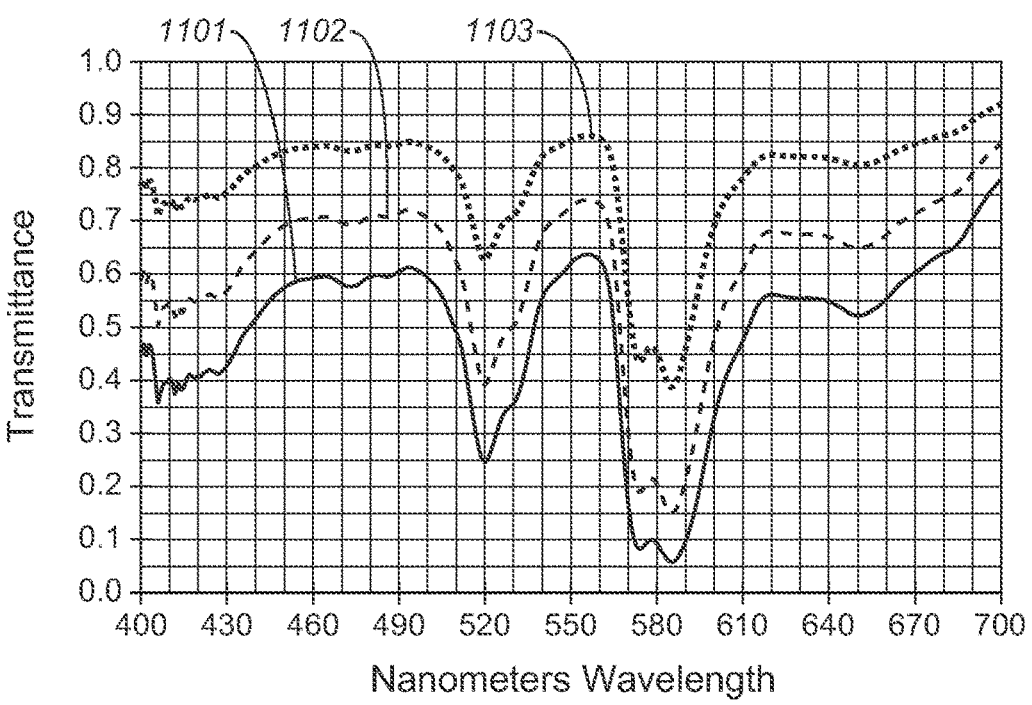
FIG. 11: Transmittance spectra of blue-colored filters comprising neodymium-oxide.

One example of a non-standard absorptive optical material are certain rare-earth oxides, in particular neodymium oxide, which has a characteristic absorption band between about 570 nanometers and about 590 nanometers. A commercially available glass containing neodymium oxide is referred to as ACE Blau and sold by Barberini SpA. Herein we analyze the performance of the ACE Blau material in a range of optical path lengths, to better understand its properties with respect to the red-green separation factor performance metric. Referring now to FIG. 11, the graph at 1101 corresponds to the ACE Blau glass at a thickness of 1.8 millimeters. The corresponding filter is referred to herein as ACE40. ACE40 provides a red-green separation coefficient of about 0.64 and a luminous transmittance of about 40%. The graph at 1102 corresponds to the ACE Blau glass at a thickness of 1.2 millimeters. The corresponding filter is referred to herein as ACE55, and has a luminous transmittance of about 55% and provides a red-green separation factor of 0.75. The graph at 1103 corresponds to the ACE Blau glass at a thickness of 0.6 millimeters. The corresponding filter is referred to herein as ACE70, and has a luminous transmittance of about 70% and provides a red-green separation factor of 0.84. The ACE series of filters have a blue-gray color, i.e. the white-point tends toward blue but is less strongly tinted than the DCB series of filters described above. While the coloration of these filters is preferable to that of the DCB and DCP series described previously (because of its lower saturation), the ACE series is not considered to have a strong enough effect on color vision to be marketed as an optical aid for color vision deficiency. An underlying issue with filters based on neodymium-oxide is the presence of an absorptive band at around 520 nanometers, which degrades the quality of green colors in particular.

Transmittance spectra of the ACE series of filters are provided in 5-nanometer (nm) steps in the table of FIG. 29.

Figure 12:
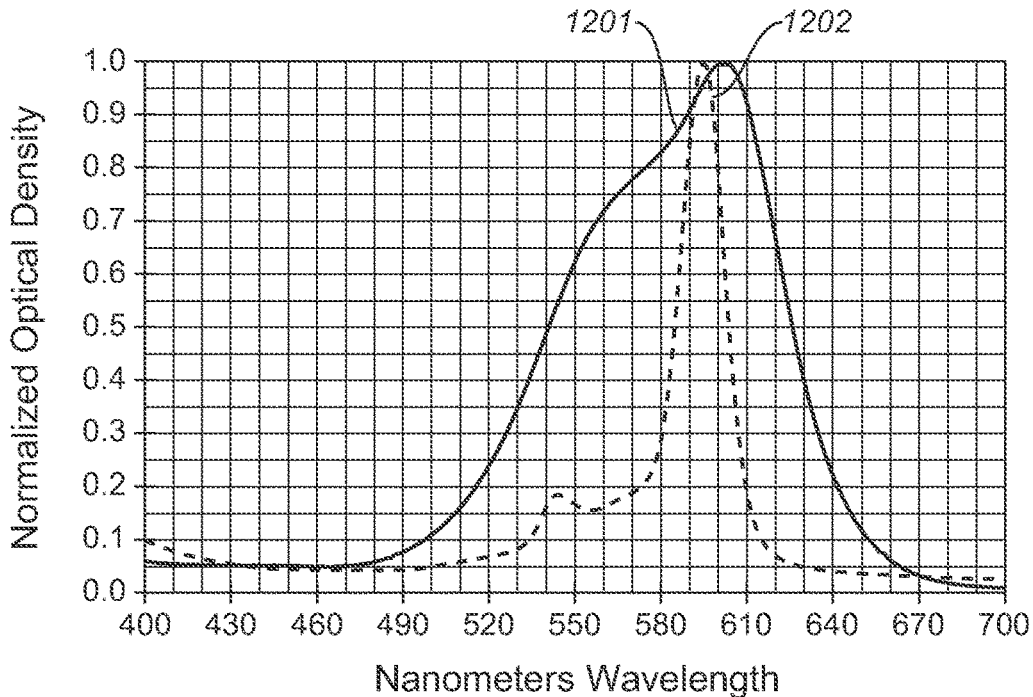
FIG. 12: Optical density spectra of a standard yellow-absorbing dye, and of a narrow-band yellow-absorbing dye.

Another example of a non-standard optical material are narrow-band dyes. We define narrow-band dyes herein to be dyes having an optical density spectra with a FWHM of less than or equal to 40 nanometers around the wavelength of maximum absorption. Narrow-band dyes are based on proprietary organic chemical formulations. Narrow-band dyes are commercially available from vendors including Exciton Inc of Dayton OH and Crysta-Lyn Chemical Company of Binghampton NY The plot shown in FIG. 12 shows the normalized optical density spectra of two dyes that both absorb yellow-light, one of which is a standard dye and the other a narrow-band dye. This plot illustrates the significant difference between standard dyes and narrow-band dyes. The graph at 1201 corresponds to the optical density of the dye SD600V, which is described previously. The dye SD600V has a FWHM of about 85 nanometers. The graph at 1202 corresponds to the optical density of a narrow-band dye, referred to as NBD595 in the present disclosure. The dye NBD595 has a FWHM of about 20 nanometers, which is significantly smaller than that of the standard dye.

Figure 13:
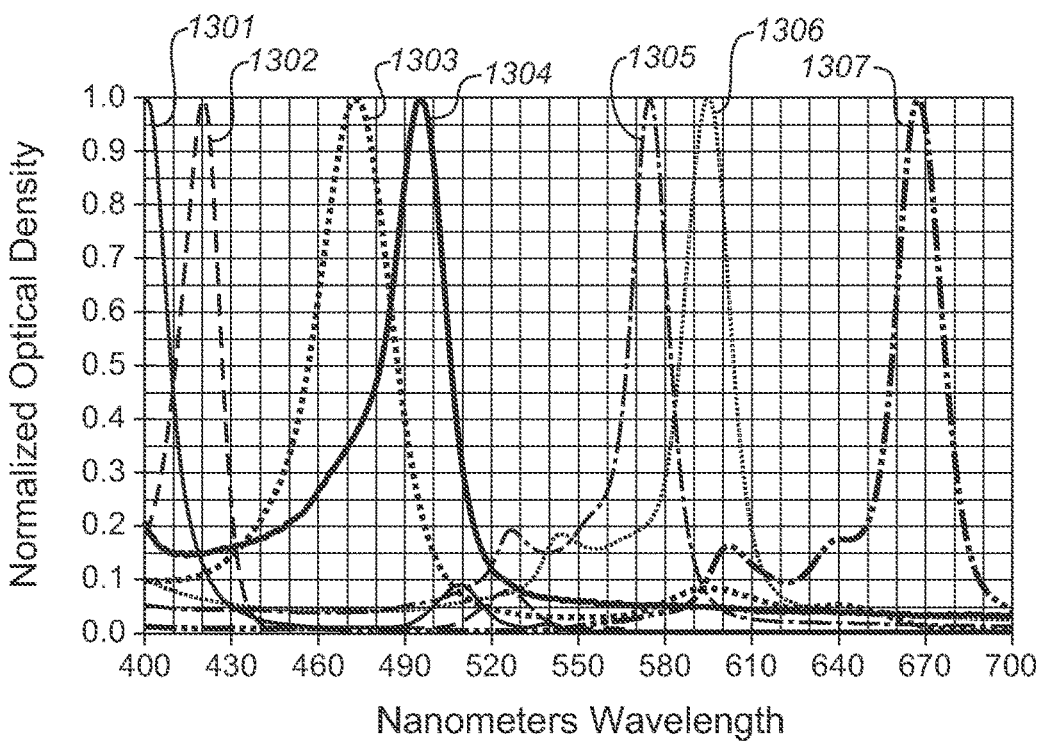
FIG. 13: Optical density spectra of selected narrow-band dyes.

The normalized optical density spectra for a collection of narrow-band dyes are plotted in FIG. 13. These selected dyes represent only a small fraction of commercial available dyes, however these were selected from those found to be most useful toward the formulation of filters for affecting color vision in a desired manner. Other candidate dyes (for example a dye with a peak absorption at about 565 nanometers) were tested by the authors, using the iterative methods described herein, and were not found to be useful, i.e. the optimal formulas always concluded with a zero concentration in the undesirable dye. The graph at 1301 corresponds to the optical density spectrum of a narrow band dye referred to herein as NBD405, and is commercially available under the brand name Exciton ABS510. The graph at 1302 corresponds to the optical density spectrum of a narrow band dye referred to herein as NBD425, and is commercially available under the name Exciton ABS527. The graph at 1303 corresponds to the optical density spectrum of a narrow band dye referred to herein as NBD475, and is commercially available under the name Exciton ABS473. The graph at 1304 corresponds to the optical density spectrum of a narrow band dye referred to herein as NBD490, and is commercially available under the name Exciton P491. The graph at 1305 corresponds to the optical density spectrum of a narrow band dye referred to herein as NBD575, and is commercially available under the name Exciton ABS575. The graph at 1306 corresponds to the optical density spectrum of a narrow band dye referred to herein as NBD595, and is commercially available under the name Exciton ABS595. The graph at 1307 corresponds to the optical density spectrum of a narrow band dye referred to herein as NBD670, and is commercially available under the name Exciton ABS668. Substitute dyes for the above commercial dyes can be found in the Crysta-Lyn product catalog, and such substitutions are comprehended by the present disclosure.

Normalized optical density spectra of the narrow-band dyes described above are provided in 5-nanometer (nm) steps in the table of FIG. 30.

Figure 14:
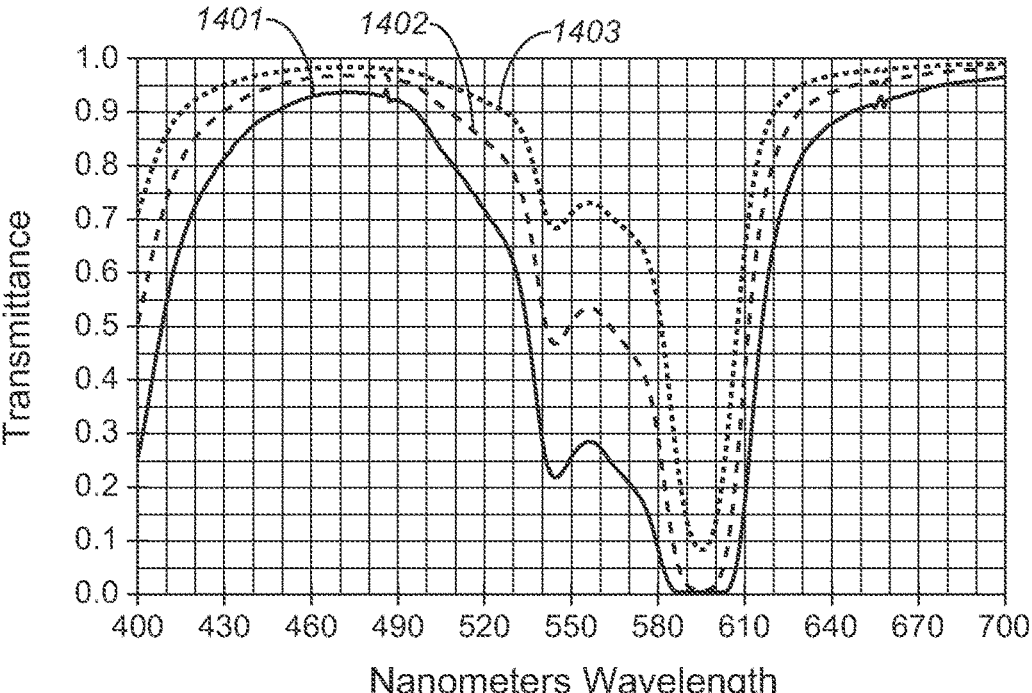
FIG. 14: Transmittance spectra of blue-colored filters comprising a single narrow-band dye.
Figure 15:
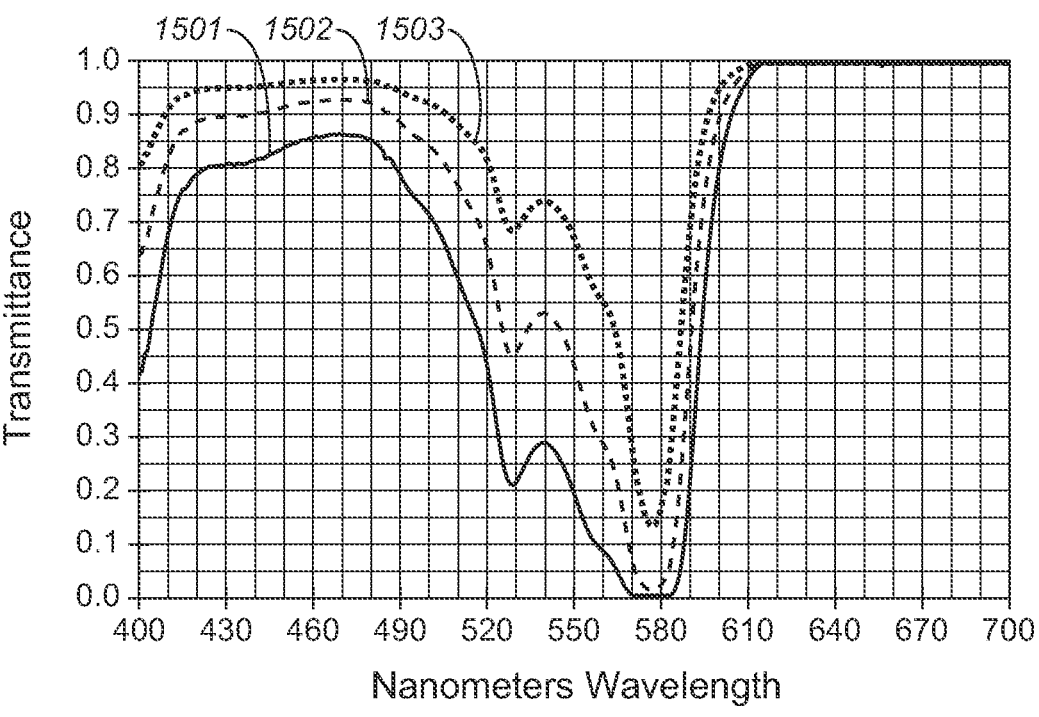
FIG. 15: Transmittance spectra of pink-colored filters comprising a single narrow-band dye.

Embodiments of filters that provide high red-green separation factors (i.e. greater than 1.0) in combination with high luminosity (i.e., luminous transmittance greater than 40%) are described hereafter along with FIG. 14 and FIG. 15. These examples are filters comprising only a single narrow-band dye component, which are readily designed by a trivial design process of simply modifying the single dye concentration until the desired luminous transmittance is achieved.

FIG. 14 depicts the transmittance spectra for a series of filters comprising only the dye component NBD595. The filters together are referred to herein as the DMB series. The graph at 1401 corresponds to a filter referred to as DMB40 having a luminous transmittance of 40% and a red-green separation factor of 2.5. The formula for DMB40 is:

$$DMB40=4.31 \times NBD595$$

The graph at 1402 corresponds to a filter referred to as DMB55 having a luminous transmittance of about 55% and a red-green separation factor of 1.97. The formula for DMB55 is:

$$DMB55 = 2.15 \times NBD595$$

The graph at 1403 corresponds to a filter referred to as DMB70 having a luminous transmittance of about 70% and a red-green separation factor of 1.82. The formula for DMB70 is:

$$DMB55 = 1.08 \times NBD595$$

Transmittance spectra of the DMB series of filters are provided in 5-nanometer (nm) steps in the table of FIG. 31.

The DMB series filters produce high amounts of red-green separation ranging between 1.8 to 2.5. The darker embodiments (DMB40 and DMB55) may be too dark for general indoor use as ophthalmic lenses. The low spectral transmittance of such filters may also pose a hazard for general use in eyewear: when the transmittance drops below the lesser of about 5%, or $\frac{1}{10}^{th}$ of the luminous transmittance ($\tau_v$), at any point in the spectrum, the resulting filter may cause the appearance of certain artificial light sources to become too dark to ensure general safety. For example, yellow LED lights are often used as warning indicator lights (for example in traffic signals). Failure to see such a light due to filtering action in an ophthalmic lens is a safety concern. The lightest embodiment of this series (DMB70), causes only a small reduction in overall luminosity (70% luminous transmittance) and has a preferable transmittance spectrum that complies with the minimum spectral transmittance needs as described. This particular embodiment was tested in eyewear by the authors and found to be adequate for a broad range of typical indoor, low-light and night time applications, while also providing a significant improvement to red-green color perception. An additional preferable property of the DMB series is that they have minimal to no effect on scotopic transmittance, in other words, night vision (as mediated by the rod cells) would be unaffected by wearing a lens comprising such a filter. A less preferable property of the DMB series is their color, which is considered blue when viewed directly through the filter, however changes to a blue-violet hue when the path length is doubled due to a reflective object placed behind the lens. In particular, when incorporated into eyewear and worn on the face, the apparent color of the skin takes on a violet or lavender color that looks disturbing and unnatural. Preferable filters for use in eyewear should have a color appearance, that when worn on the face, are blue, pink, red, yellow, brown or gray. Therefore, a filter embodiment such as DMB70 could be a preferable choice when considering a filter for incorporated into an ophthalmic system where the coloration is not visible to the outside observer: such as a contact lens or a spotting scope assembly.

The transmittance spectra for another series of filters, where the filters consist of only a single narrow-band dye component, are shown in FIG. 15. The graph at 1501 corresponds to a filter referred to as DMP40 having a luminous transmittance of 40% and a red-green separation factor of 2.28. The formula for DMP40 is:

$$DMP40 = 3.58 \times NBD575$$

The graph at 1502 corresponds to a filter referred to as DMP55 having a luminous transmittance of about 55% and a red-green separation factor of 2.15. The formula for DMP55 is:

$$DMP55 = 1.83 \times NBD575$$

The graph at 1503 corresponds to a filter referred to as DMB70 having a luminous transmittance of about 70% and a red-green separation factor of 1.98. The formula for DMP70 is:

$$DMP70 = 0.875 \times NBD575$$

Transmittance spectra of the DMP series of filters are provided in 5-nanometer (nm) steps in the table of FIG. 32.

The DMP series have a color appearance usually described as pink: when worn on the face in eyewear, in particular for the darker DMP40 and DMP55, the color appearance is unusually strong and is found to be not aesthetically pleasing.

The DMP70 filter and DMB70 filter are preferable for use in contact lenses, whereas use of a contact lens requires a high luminous transmittance (e.g. at least 70%), and the aesthetic issues with coloration as described are irrelevant. In addition, with respect to the application of a contact lens for assistance with protanomalous or deuteranomalous color vision deficiency, the transmittance spectra of the DMB70 filter is preferable for use with deuteranomalous color vision deficiency and the transmittance spectra of the DMP70 filter is preferable for use with protanomalous color vision deficiency. This preference follows from the observation that 1) protanomalous individuals experience a reduced sensitivity to long-wavelength visible light (i.e. red light) and 2) protanomalous individuals experience a lower wavelength of unique yellow whereas deuteranomalous individuals experience a longer wavelength of unique yellow and a higher sensitivity to longer wavelengths of light. A method for prescribing a contact lens to an individual with color vision deficiency may comprise first conducting a color blindness test to determine their type and extent of deficiency, and then recommending an appropriate lens selected from the two contact lens alternatives having transmittance spectra substantially as described above. In another variation on the method just described, a spectacle lens can be recommended by a similar procedure, and whereas spectacle lenses may have a lower luminous transmittance (e.g. between 40% and 60%), filters incorporated into such lenses may contain a mixture of both NBD575 and NBD595 (or equivalent) narrow-band dyes. In these variations the method comprises recommending to the deuteranomalous individual a lens containing an optical filter substantially similar to one of the CXB series filters (described below), and/or to the protanomalous individual a lens containing an optical filter substantially similar to one of the CXV series filters (also described below). A property shared by the CXB series filters is that the transmittance of the filter at 575 nanometers is at least about 2 times greater than the transmittance of the filter at 595 nanometers. A property shared by the CXV series filters is that the transmittance of the filter at 595 nanometers is at least about 2 times greater than the transmittance of the filter at 575 nanometers.

Embodiments of filters comprising combinations of 2 or more dyes including at least one narrow-band absorbing dye are described in detail below along with FIG. 16, FIG. 17, FIG. 18, FIG. 19 and FIG. 20. The design complexity of such filters increases with each additional dye under consideration (i.e., the number of possible metameric filters satisfying the input chromaticity constraints is non-trivial), and so the dye formulas of such filters are preferably optimized using the iterative methods described above along with FIGS. 1-4. The preferred configuration and variations of the design method are described along with these corresponding filter examples.

Figure 16:
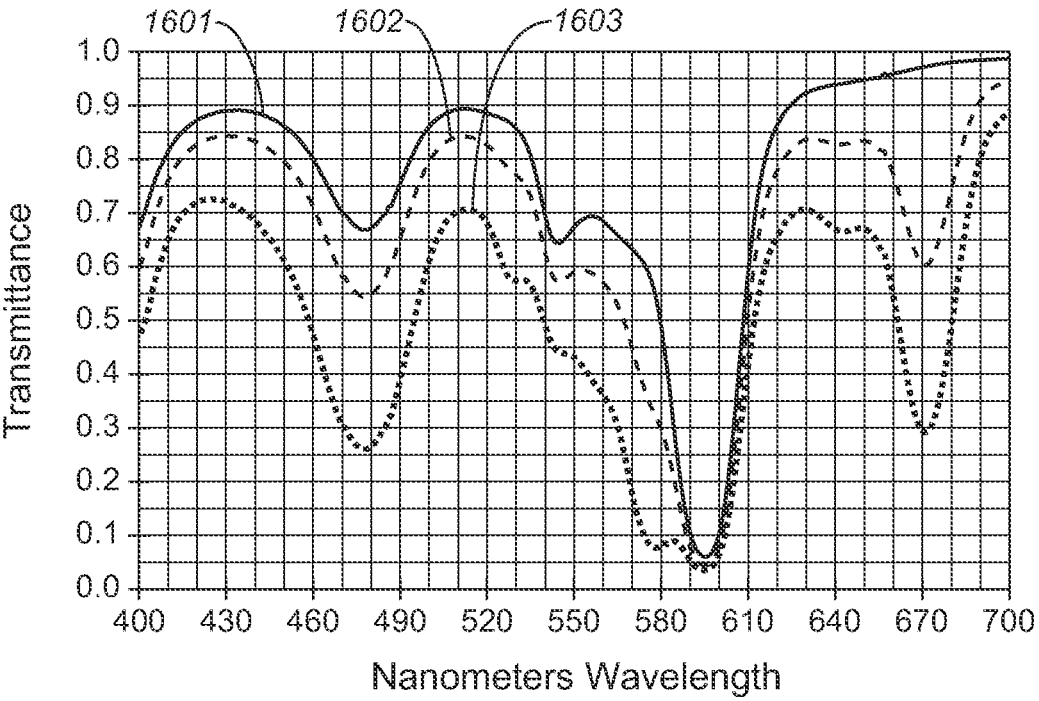
FIG. 16: Transmittance spectra of blue-colored filters comprising a plurality of narrow-band dyes.

The transmittance spectra of a series of filters is shown in FIG. 16. These filters are referred to herein as the CXB series. The filters comprise a combination of between 2 and 4 narrow-band dye components. The filters have a blue-green color (i.e. the white-point tends toward blue and also toward green). However, the provided colors are not strong, appearing to also be substantially similar to gray. The series of filters includes embodiments having luminous transmittance between about 40% and about 65%. The graph at 1603 corresponds to a filter referred to herein as CXB40 having a luminous transmittance of 40% and a red-green separation factor of 1.72. The formula for CXB40 is:

$$CXB40=0.511 \times NBD670+0.557 \times NBD475+0.795 \times NBD575+1.29 \times NBD595$$

The graph at 1602 corresponds to a filter referred to herein as CXB55 having a luminous transmittance of 55% and a red-green separation factor of 1.57. The formula for CXB55 is:

$$CXB55=0.251 \times NBD475+0.199 \times NBD575+1.29 \times NBD595$$

The graph at 1601 corresponds to a filter referred to herein as CXB65 having a luminous transmittance of 65% and a red-green separation factor of 1.55. The formula for CXB65 is:

$$CXB65=0.167 \times NBD475 \ 1.21 \times NBD595$$

Transmittance spectra of the CXB series of filters are provided in 5-nanometer (nm) steps in the table of FIG. 33.

Optimized formulas for the CXB series (e.g. as disclosed above), where the corresponding optimized filters provide preferable red-green separation factors (greater than 1.0) and high luminous transmittance (greater than about 40%) may be produced by evaluating the described iterative design method using the red-green separation factor as the colorimetric performance measure and a blue-green chromaticity coordinate as the target white-point. Preferably the blue-green chromaticity coordinate corresponds to hue between 10B and 5B and chroma of between 4 and 6 according to the Munsell color system.

Figure 17:
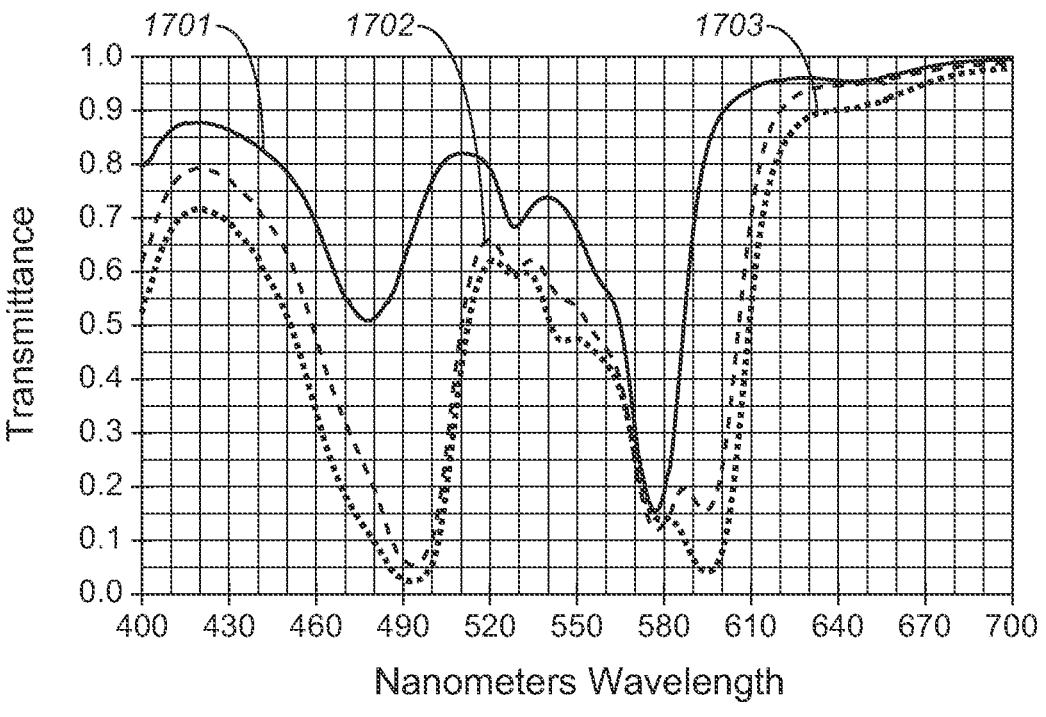
FIG. 17: Transmittance spectra of vermillion-colored filters comprising a plurality of narrow-band dyes.

The transmittance spectra of another series of filters is shown in FIG. 17. These filters are referred to herein as the CXV series. The filters comprise a combination of between 2 and 4 narrow-band dye components. The filters provide a white-point color considered a vermillion, which is a gray color with a mild pink or purple tint. The series of filters includes embodiments having luminous transmittance between about 40% and about 65%. The graph at 1703 corresponds to a filter referred to herein as CXV40 having a luminous transmittance of 40% and a red-green separation factor of 1.3. The formula for CXV40 is:

$$CXV40=0.39 \times NBD475+0.557 \times NBD575+1.29 \times NBD595+1.39 \times NBD490$$

The graph at 1702 corresponds to a filter referred to herein as CXV55 having a luminous transmittance of 55% and a red-green separation factor of 1.46. The formula for CXV55 is:

$$CXV55=0.195 \times NBD475+0.755 \times NBD575+0.724 \times NBD595+1.14 \times NBD490$$

The graph at 1701 corresponds to a filter referred to herein as CXV65 having a luminous transmittance of 65% and a red-green separation factor of 1.48. The formula for CXV65 is:

$$CXV65=0.279 \times NBD475+0.795 \times NBD575$$

Transmittance spectra of the CXV series of filters are provided in 5-nanometer (nm) steps in the table of FIG. 34.

Optimized formulas for the CXV series (e.g. as disclosed above), where the corresponding optimized filters provide preferable red-green separation factors (greater than 1.0) and high luminous transmittance (greater than about 40%) may be produced by evaluating the described iterative design method using the red-green separation factor as the colorimetric performance measure and a purple or pink chromaticity coordinate as the target white-point. Preferably the target white-point corresponds to hue of about 5P and chroma between 2 and 4 according to the Munsell color system.

Figure 18:
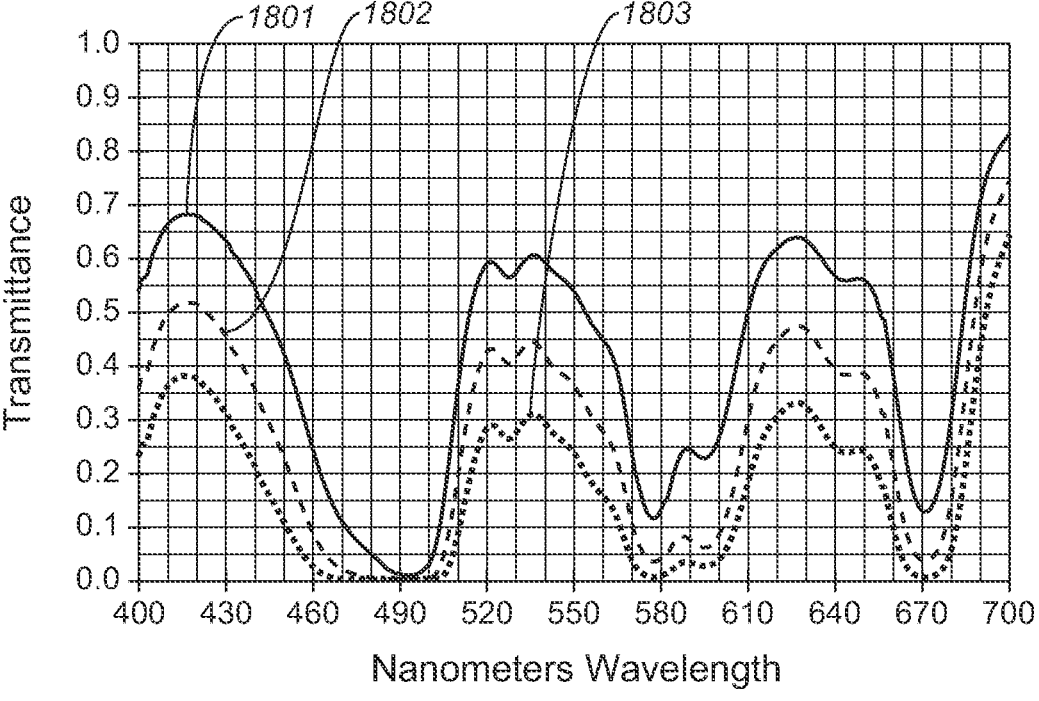
FIG. 18: Transmittance spectra of gray-colored filters comprising a plurality of narrow-band dyes.

The transmittance spectra of another series of filters is shown in FIG. 18. These filters are referred to herein as the CXN series. The filters comprise a combination of 5 narrow-band dye components. The filters provide a white-point color considered to be neutral, or substantially gray with little to no apparent coloration. The series of filters includes embodiments having luminous transmittance between about 14% and about 40%. The graph at 1801 corresponds to a filter referred to herein as CXN40 having a luminous transmittance of 40% and a red-green separation factor of 0.69. The formula for CXN40 is:

The graph at 1802 corresponds to a filter referred to herein as CXN25 having a luminous transmittance of 25% and a red-green separation factor of 0.594. The formula for CXN25 is:

$$CXN25=0.862 \times NBD595+1.06 \times NBD475+1.11 \times NBD575+1.38 \times NBD670+2.53 \times NBD490$$

The graph at 1801 corresponds to a filter referred to herein as CXN15 having a luminous transmittance of 15% and a red-green separation factor of 0.497. The formula for CXN15 is:

$$CXN15=1.03 \times NBD595+1.59 \times NBD475+1.67 \times NBD575+2.07 \times NBD670+3.79 \times NBD490$$

Transmittance spectra of the CXN series of filters are provided in 5-nanometer (nm) steps in the table of FIG. 35.

Optimized formulas for the CXN series (e.g. as disclosed above), where the corresponding optimized filters provide strong color-enhancement effects and a low luminous transmittance appropriate for incorporation into sunglasses (less than 40%) may be produced by evaluating the described iterative design method using a gamut-area based performance metric. For example, the performance metric may be defined as the area enclosed by a set of chromaticity coordinates corresponding to a set of reference colors as seen through the filter, and the reference colors correspond to the Munsell color swatches used in the Farnsworth D-15 cap arrangement test. The gamut area performance measure is described in U.S. patent application Ser. No. 14/014,991. Preferably the target white-point corresponds to a chroma of less than 2 according to the Munsell color system.

Figure 19:
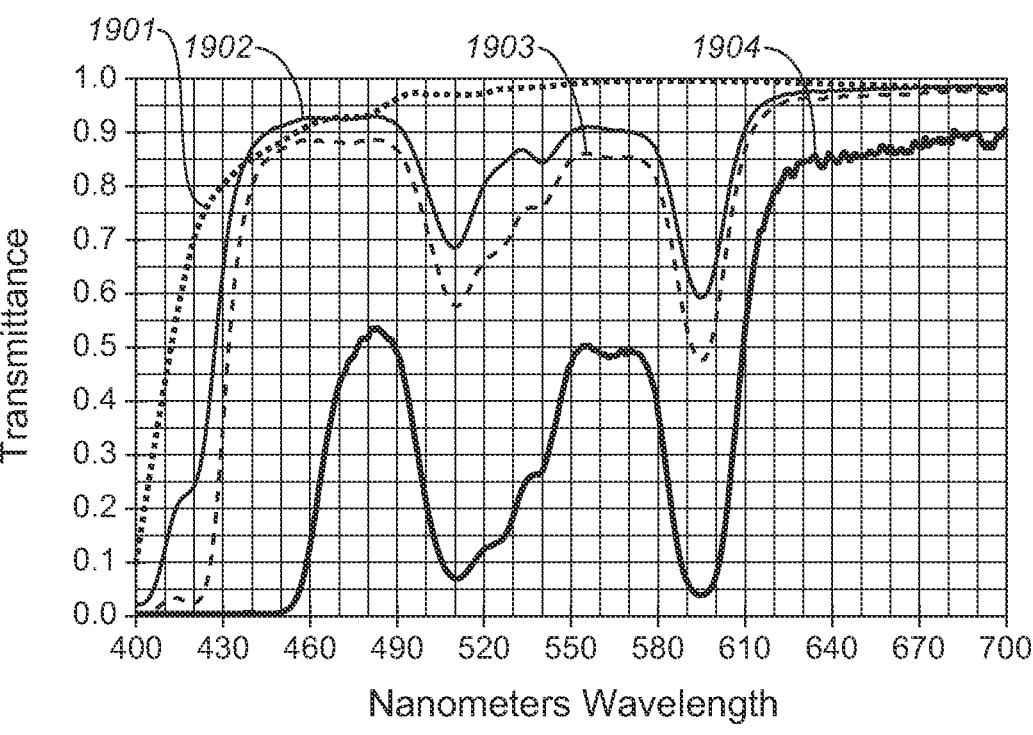
FIG. 19: Transmittance spectra of HEV (high energy visible) radiation-absorbing filters comprising a plurality of narrow-band dyes and/or standard dyes.

The transmittance spectra of another series of filters is shown in FIG. 19. These filters are referred to herein as the UVH series. The filters comprise a combination of 3 narrow-band dye components and optionally 1 standard dye component. The series of filters includes embodiments having luminous transmittance between about 35% and about 85%. The UVH series of filters are designed to inhibit the transmission of high-energy visible light (also called HEV light), which is a sub-band of visible light where photons have the greatest energy, corresponding to wavelengths between about 390 nanometers and about 450 nanometers. The graph at 1901 corresponds to a commercially available HEV-blocking filter known by the trade name BluTech. This filter is characterized by a nearly monotonic change in transmittance across the spectrum. The UVH series of filters disclosed herein have complex spectral profiles that are non-monotonic in transmittance per wavelength. The graph at 1902 corresponds to a filter referred to herein as UVH415 having a luminous transmittance of 85%. The formula for UVH415 is:

$$UVH415=0.227 \times NBD595+0.397 \times NBD425+1.57 \times NBD405$$

The graph at 1903 corresponds to a filter referred to herein as UVH430 having a luminous transmittance of 75%. The formula for UVH430 is:

$$UVH430=0.322 \times NBD595+1.32 \times NBD425+2.09 \times NBD405$$

The graph at 1904 corresponds to a filter referred to herein as UVH450 having a luminous transmittance of 35%. The formula for UVH450 is:

$$UVH450=1.4 \times NBD595+7.15 \times NBD425+9.95 \times NBD405+2.08 \times SD435Y$$

Transmittance spectra of the UVH series of filters are provided in 5-nanometer (nm) steps in the table of FIG. 36.

The filter examples UVH415 and UVH430 provide filters with high luminous transmittance and are adequate for general purpose eyewear intended for indoor use and night-time use. These filters have colors that are substantially neutral, which are preferable for aesthetic reasons. In addition, the configuration of notches in the spectral transmittance (e.g. at 510 nanometers and at 590 nanometers) provide a small but noticeable increase to the quality of color vision.

The filter example UVH450 has a color that is considered yellow or brown, and has a correlated color temperature of about 2700 Kelvin. The filter is preferable for incorporation into a sunglass lens, where it may also be combined with a polarizing filter, and/or a photochromic dye. The spectral transmittance of the UVH450 example is less than 1% for all wavelengths from 400 nanometers to 450 nanometers, enabling the use of the claim "UV450" for commercial advertising, which is related to the term "UV400" which is defined by the industry to indicate a lens that blocks at least 99% of light with wavelength of 400 nanometer or less. In another variation, the concentration of standard dye component SD435Y may be reduced in the formula provided above, to yield a filter with a lower protection rating, e.g. "UV425", with the tradeoff that the resulting filter color may be preferable insofar as its saturation (chroma) is reduced. Preferably the filter color has a chroma of between 2 and 4 according to the Munsell color system.

Optimized formulas for the UVH series (e.g. as disclosed above), where the corresponding optimized filters provide HEV light protection in combination with preferable filter color may be produced by evaluating the described iterative design method using the HEV attenuation factor, a colorimetric performance measure calculated by the formula $$\Psi_{HEV}=((\tau_v \times ((\tau_H/\tau_L)-1))/(1-\tau_v)+1)$$

Wherein, in the above formula, $\tau_H$ is the mean transmittance of the filter between about 390 nanometers and about 450 nanometers, $\tau_L$ is the mean transmittance of the filter between about 450 nanometers and about 650 nanometers, and $\tau_v$ is the luminous transmittance of the filter. For such filters having a high luminous transmittance (e.g. greater than 75%) the white-point preferably corresponds to a chroma of less than 2 according to the Munsell color system.

For such filters having a low luminous transmittance (e.g. less than 40%) the white-point is preferably within about 0.025 units of the black-body locus in the CIE xy chromaticity space. The HEV attenuation factor of filter example UVH415 is about 6.1 and the red-green separation factor is about 0.47. The HEV attenuation factor of filter example UVH430 is about 6.2 and the red-green separation factor is about 0.35. The HEV attenuation factor of filter example UVH450 is about 44.2 and the red-green separation factor is about 0.25. The filter examples UVH415 and UVH430 provide a white-point with low saturation, wherein the distance to the standard appearance of D65 at the (x, y) coordinates (0.31, 0.33) is at most about 0.025 units. The filter example UVH450 provides a white-point that is substantially considered yellow and essentially transforms Standard Illuminant D65 (having a correlated color temperature of 6500 Kelvin) to the color of Standard Illuminant A (having a correlated color temperature of 2700 Kelvin).

Figure 20:
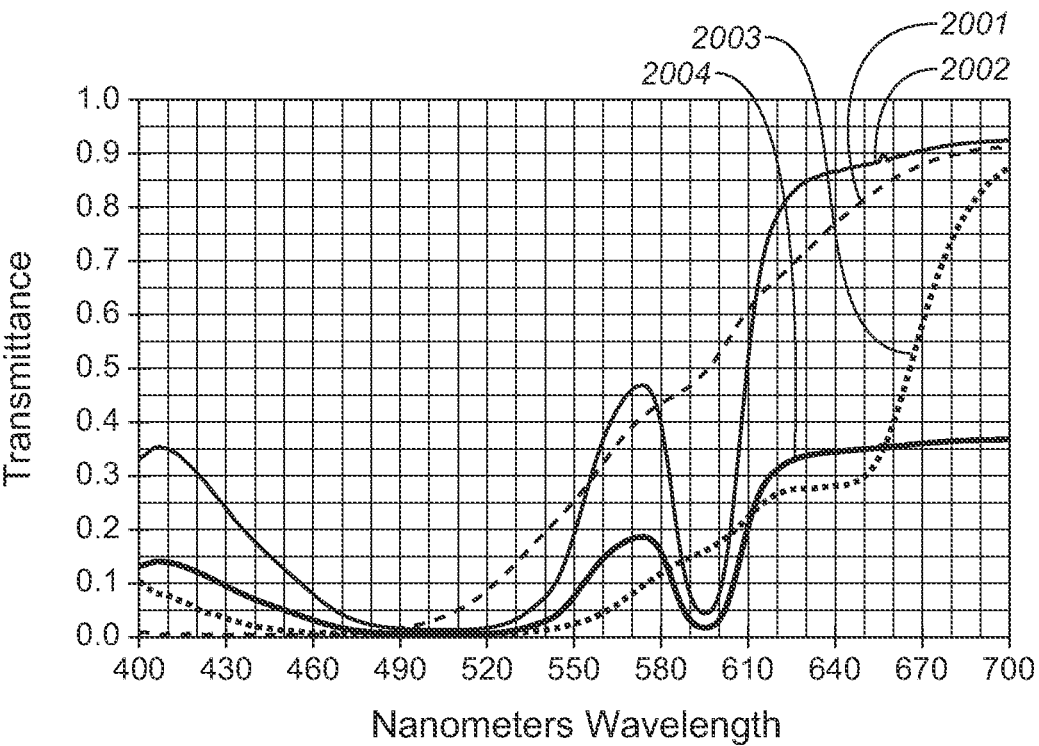
FIG. 20: Transmittance spectra of achromatopsia-assistive filters comprising a plurality of narrow-band dyes and/or standard dyes.

The transmittance spectra of another series of filters is shown in FIG. 20. These filters are referred to herein as the ACR series. The filters comprise a combination of 2 narrow-band dye components and 1 standard dye component and optionally a neutral density absorber (such as a gray dye mixture, a gray photochromic dye, or a gray polarizer). The ACR series of filters are designed to inhibit the transmission of scotopic light (light received by the rod cell photopigment), which are photons having a wavelength between about 450 nanometers and about 550 nanometers. Filters that significantly limit the transmission of scotopic light are often prescribed for individuals who suffer from achromatopsia, a low-vision condition characterized by partial or complete lack of functioning cone cells. The limited scotopic transmission enables the wearer to use scotopic vision (i.e. night vision) to see during typical indoor lighting and outdoor daylight conditions. One approach to meeting such needs would be to provide a neutral gray filter of the appropriate darkness, however this is less preferable compared to an orange or red filter that enables partial color vision. Cases of achromatopsia can be classified as either complete achromatopsia (i.e. total loss of cone function) or incomplete achromatopsia (i.e. partial loss of cone function). For the latter case, a lens providing selective transmission is preferred. The graph at 2001 corresponds to a conventional filter which may be prescribed by an ophthalmologist for use indoors with achromatopsia. This filter has an orange color and a luminous transmittance of about 30%. The graph at 2003 corresponds to a conventional filter which may be prescribed by an ophthalmologist for use outdoors with achromatopsia. This filter has a red color and a luminous transmittance of about 8%. Such filters can be purchased commercially, for example the orange-colored Filter #570 from NoIR Medical Technologies Inc of South Lyon, MI, and the red-colored Filter #95 and Filter #99 also from NoIR Medical Technologies Inc of South Lyon, MI The ACR series of filters shown here improve upon these conventional designs by incorporating color-enhancing dyes (e.g. NBD595) which may provide better color vision to individuals with incomplete achromatopsia. The graph at 2002 corresponds to a filter referred to herein as ACR25 having a luminous transmittance of 25%. The formula for ACR25 is:

$$ACR25=0.167 \times NBD475+1.29 \times NBD595+1.81 \times SD510R$$

The graph at 2004 corresponds to a filter referred to herein as ACR10 having a luminous transmittance of 10%. ACR10 employs the same underlying formula as ACR25 with the addition of a neutral-density absorber transmitting 40% of the light. For example, the absorber may be a neutral-density dye (e.g. typically a mixture of standard dyes to form gray and having a transmittance that is approximately constant per wavelength), preferably is a linear polarizer element, or is preferably a photochromic dye, or is more preferably a polarizing photochromic dye.

Transmittance spectra of the ACR series of filters are provided in 5-nanometer (nm) steps in the table of FIG. 37.

The design of filters such as those in the ACR series are enabled by a variation on the iterative design method wherein the target white-point constraint is replaced by a scotopic transmittance constraint (i.e. apparent brightness according to the receptivity of the rod cell photopigment). The substitution is appropriate since the extreme needs of the desired effect on color vision override any preference on the filter color. The target scotopic transmittance is preferably less than about 10%, or is preferably less than about ⅓$^{rd}$ of the luminous transmittance of the filter. In combination with the modified constraint, a measure of general color enhancement may be applied as the colorimetric performance measure, for example a gamut-area based metric as described previously whereas gamut-area metrics are preferable in the design of dark (low luminous transmittance) filters, or the red-green separation factor may be used as a colorimetric performance measure to drive the optimal solution toward a filter that improves color vision.

Figure 21:
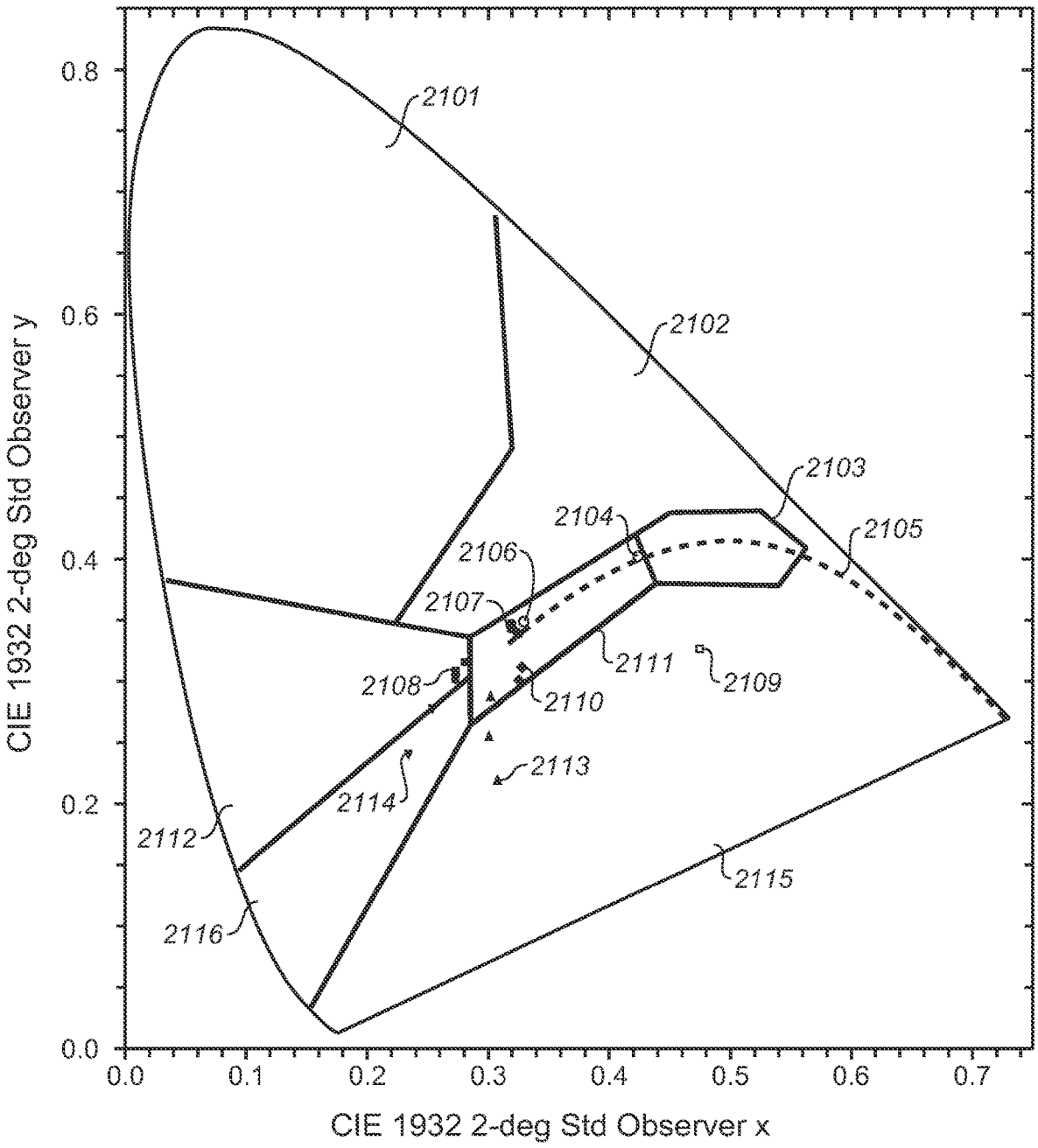
FIG. 21: Chromaticity plot showing white-point locations of selected filters, and chromaticity regions for categorization of filter colors.

FIG. 21 depicts a chromaticity diagram according to the CIE Yxy color space with respect to the CIE 1931 2-degree standard observer. The dotted line at 2105 corresponds to the Planckian locus (or black-body locus) which is the curve in chromaticity space of an ideal black-body radiator having a temperature between 10000 Kelvin and 0 Kelvin. Filters that are preferable for integration into ophthalmic systems are those having 1) not strongly colored tints, and 2) preferably colors which are near the black-body locus. A region that satisfies these preferable properties is indicated at 2111. The region spans the black-body locus temperatures from about 8000K to about 2700K. White-point colors falling into this region are substantially considered to be neutral in appearance, or mostly neutral but taking on a slight coloration. The white-points of filter series CXN are indicated by the solid circle markers at 2107 which correspond to essentially gray or neutral colors with a correlated color temperature of 6500K. The white-points of filter series UVH are indicated by the open circle markers at 2106 and 2104, with 2106 corresponding to example UVH430 and the marker at 2104 corresponding to example UVH450. The filter UVH430 has a substantially neutral appearance with a slight tint toward yellow. The filter UVH450 takes on a stronger yellow (or brown) appearance and has a correlated color temperature of about 2700K. A less preferable region of color is indicated at 2103 spanning correlated color temperatures of 2700K to about 2000K, where filters in this region may be appear orange. Another region that is less preferable for the color of filters is indicated approximately at 2115 corresponding to pink, purple and red colors with strong coloration. The filter series ACR (ACR25 and ACR10) have a white-point corresponding to the open square marker at 2109, which is a red color. The less preferable color is a necessary consequence of the scoptopic transmittance constraints. In another example, the filter series DMP has corresponding white-points indicated by the upright triangles at 2113, with the most saturated marker corresponding to the filter DMP40. These filters have a strong pink or purple color that is considered undesirable for aesthetic reasons. The CXV series of filters also have a white-point that tends toward pink, but are fully contained within the preferable region at

2111, wherein the diamond markers at 2110 correspond to the white-points of these filters. Pink-ish or purple-ish filters that are nearly gray are also called "vermillion", especially in the eyewear industry. Another region in chromaticity space that is also less preferable (in particular for eyewear) is indicated at 2116: this region corresponds to substantially blue-violet filters, which have an unusual appearance that is not preferred by most consumers. The filter series DMB has corresponding white-points in this region indicated by the inverted triangles at 2114. Whereas blue-ish filters are preferred for achieving high red-green separation factors simultaneously with high luminous transmittance, the chromaticity region indicated at 2112 demarcates an area corresponding to blue-green colors, within which the white-points of the filter series CXB are contained and indicated by the solid square markers at 2108. The region 2101 corresponds to strong green colors and the region 2102 to yellow-green colors which are again less preferable than embodiments contained within the regions 2111 or 2112.

A scatter plot demonstrating the red-green separation factor ($\Psi_{RG}$) versus luminous transmittance ($T_v$) for the filter examples described above is shown in FIG. 22, corresponding data tabulated in FIG. 38 and FIG. 39. Neutral filters (equal transmittance at all wavelengths) provide a red-green separation factor of zero (for example shown by the inverted triangles at 2204 corresponding to neutral filters of 40% (ND40), 55% (ND55) and 70% (ND70) luminous transmittance. Analysis of this plot is useful to better understand how red-green separation factor as a colorimetric performance measure defines preferable properties of filters intended for use as optical aids for red-green color blindness, in particular for such filters rated as Category 1 lenses (which are nominally lenses having a luminous transmittance between about 40% and about 80%). Category 1 lenses are not considered suitable as sunglass lenses. Category 1 lenses have a high enough luminosity that they may be usable under typical indoor lighting conditions, as well as low-light situations such as evening and night-time use. Filters such as the CXN25 and CXN15 are found to have strong color enhancement effects, however are too dark for indoor use. The filter CXN40 has a luminous transmittance corresponding to the lower limit for a Category 1 lens, however in subjective user testing was found to have only a mild effect on color perception, where CXV40 and CXB40 were found to have a strong effect. We conclude that the red-green separation factor as colorimetric performance measure is a reasonable choice for use with our iterative design method when the target luminosity is greater than about 40%. The region indicated at 2201 shows the preferable range of red-green separation factor versus luminous transmittance for Category 1 lenses, wherein the luminous transmittance is between about 40% and about 80% and the red-green separation factor is greater than 1.0. Preferably such filters provide a red-green separation factor greater than about 1.25, or greater than about 1.5, or greater than about 2.0. Preferably such filters provide luminous transmittance greater than about 50%, or greater than about 60%. The region indicated at 2202 encloses filter designs having a luminous transmittance in the Category 1 range, but also having red-green separation factor of less than 1.0, as described previously (e.g. the ACE series, DCB, and DCP series). The region indicated at 2203 encloses filter designs having a luminous transmittance in the Category 2 range (comprising luminous transmittance from about 18% to about 40%) or having a luminous transmittance in the Category 3 range (comprising luminous transmittance from about 8% to about 18%). Category 2 lenses are considered medium sunglass lenses, and Category 3 lenses are considered dark sunglass lenses.

The integration of dye-based filters into ophthalmic systems is accomplished in a variety of methods that are known in the ophthalmic lens industry. An example of a possible ophthalmic system containing a dye-based filter is shown in FIG. 23A, wherein the layers of an ophthalmic system are depicted in a stacked arrangement. In this example the top layer (side of the lens furthest from the eye) is a hydrophobic coating 23A01, the next layer is an anti-reflection coating 23A02 (which itself comprises several layers), the next layer is the functional coating layer where the dye-based filter is contained, for example by dispersing of the dyes throughout an acrylate-based coating. The functional coating is bonded to a lens substrate 23A04 using any suitable method of attachment (spin-on, mold transfer, etc.). The backside of the lens substrate is then additionally coated with a back-side anti-reflection coating 23A05 and back-side hydrophobic coating 23A06. The system described above is preferable for the formation of a prescription lens (a lens containing focusing power). Prescription lenses use variation in thickness across the surface of the lens to create optical power, however to maintain uniform spectral filtering, the functional coating should maintain an approximately constant thickness. Thus, integration of the dye components into the lens substrate is less preferable if the lens also function to create optical power. In another variation, the lens may have zero power, or have a reasonably low power (e.g. between +/−2 diopters), and in such a variation the filter dyes may be dispersed directly into the lens substrate 23A04, and the functional coating layer omitted 23A03. In additional variations, the functional coating may be applied on the back surface of the lens substrate, or the component dyes may be distributed between both the lens substrate and a functional coating. In additional variations, the anti-reflection coatings and/or hydrophobic coatings may be omitted. In further variations, the dyes may be dispersed into a hard-coat (anti-scratch coating) that is applied to both the front and back surfaces of the lens substrate. Another type of ophthalmic lens is a contact lens, wherein the dye solution may be integrated into the lens substrate, or into a region within the substrate, such that the dye components are chemically bonded to the polymer forming the contact lens.

The integration of a dye-based filter into a lamp assembly is depicted in FIG. 23B. Herein the lamp assembly comprises an illuminant 23B05 (e.g. an LED, incandescent filament or gas-discharge tube), a beam-forming lens 23B04, which may cast a narrow beam, wide beam or other spatial distribution of light, and a window that the beam of light passes through 23B02. Herein the filter component dyes are dispersed within the substrate forming the window. For improved efficiency the window may include anti-reflection coatings on the front 23B01 and back 23B03 surfaces. In another variation, the component dyes may be applied using a functional coating (as described previously) directly on the surface of the beam forming lens, instead of using a window. In another variation, the component dyes may be dispersed directly into the beam forming lens. In another variation the beam-forming lens may comprise a mirror (e.g. a parabolic or ellipsoidal mirror), and the component dyes applied as a functional coating on the surface of the mirror, and the concentration of the dyes are reduced by about 50% to account for the doubling of the effective path length. In some variations, only a portion of the light beam is filtered.

Figure 24A:
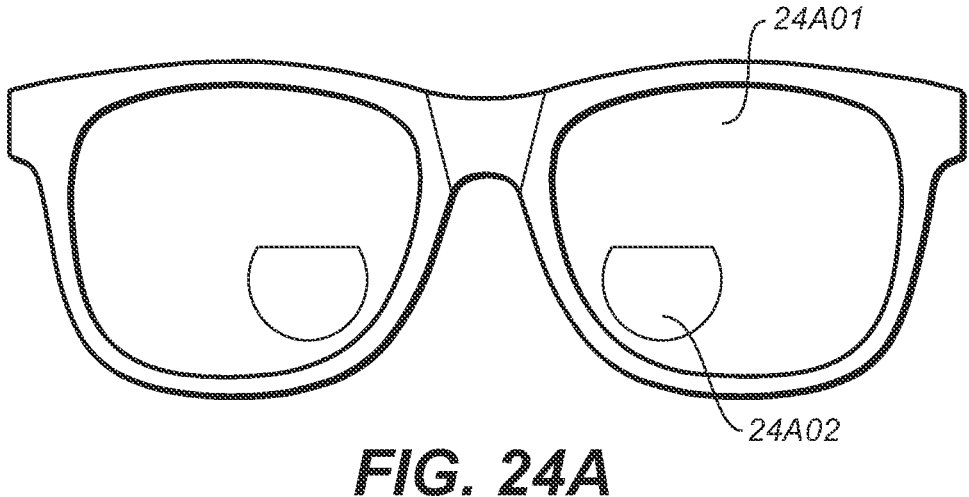
FIG. 24A: Diagram showing region on a lens where a filter can be applied to provide a desired effect on color vision for near-field viewing conditions.
Figure 24B:
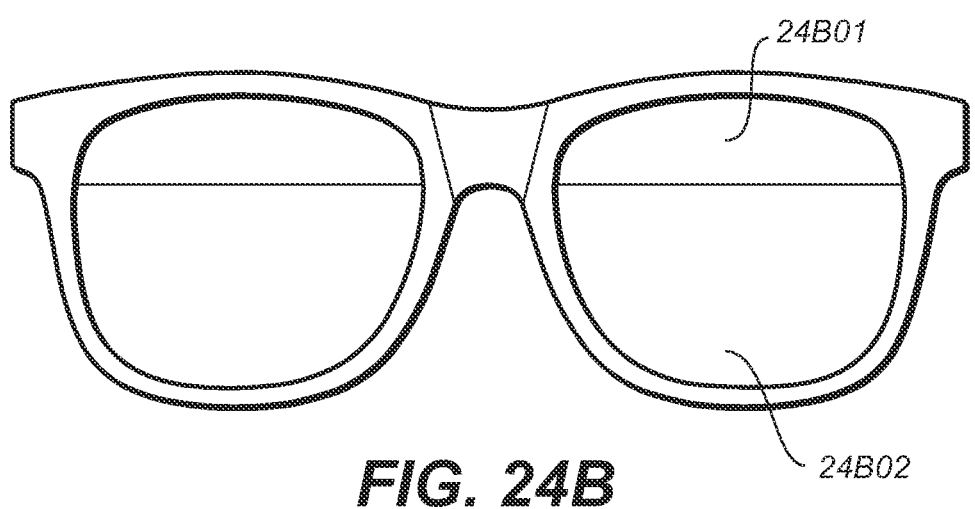
FIG. 24B: Diagram showing region on a lens where a filter can be applied to provide a desired effect on color vision for far-field viewing conditions.

With respect to the integration of Category 1 filters (having luminous transmittance between about 40% and about 80%) into eyewear, the reduced luminosity of the filter may present issues with visual obstruction to the wearer in certain lighting conditions, especially in low-light or night-time conditions. The issues can be alleviated by restriction of the application of the optical filter to a region within a lens. FIG. 24A shows an example pair of eyewear where the lens 24A01 contains a near-field region at 24A02. In such an example the filter may be applied as to only affect vision in the near-field region 24A02. Such an arrangement may be useful for eyewear intended for use where enhanced color vision is required for close-up task work, without obstructing vision generally. In another example, FIG. 24B shows an example pair of eyewear where the lens is split into a near-field region at 24B02 and a far-field region at 24A01. In such an example the filter may be applied as to only affect vision in the far-field region 24B02. Such an arrangement may be preferred when the eyewear is intended for use assistance with interpretation of colored signal lights (for example in marine, automobile or aviation navigation) and where the signal lights are primarily seen above the horizon line. In another variation the split between near-field and far-field regions is a continuous gradient, rather than a having a distinct line.

Figure 25:
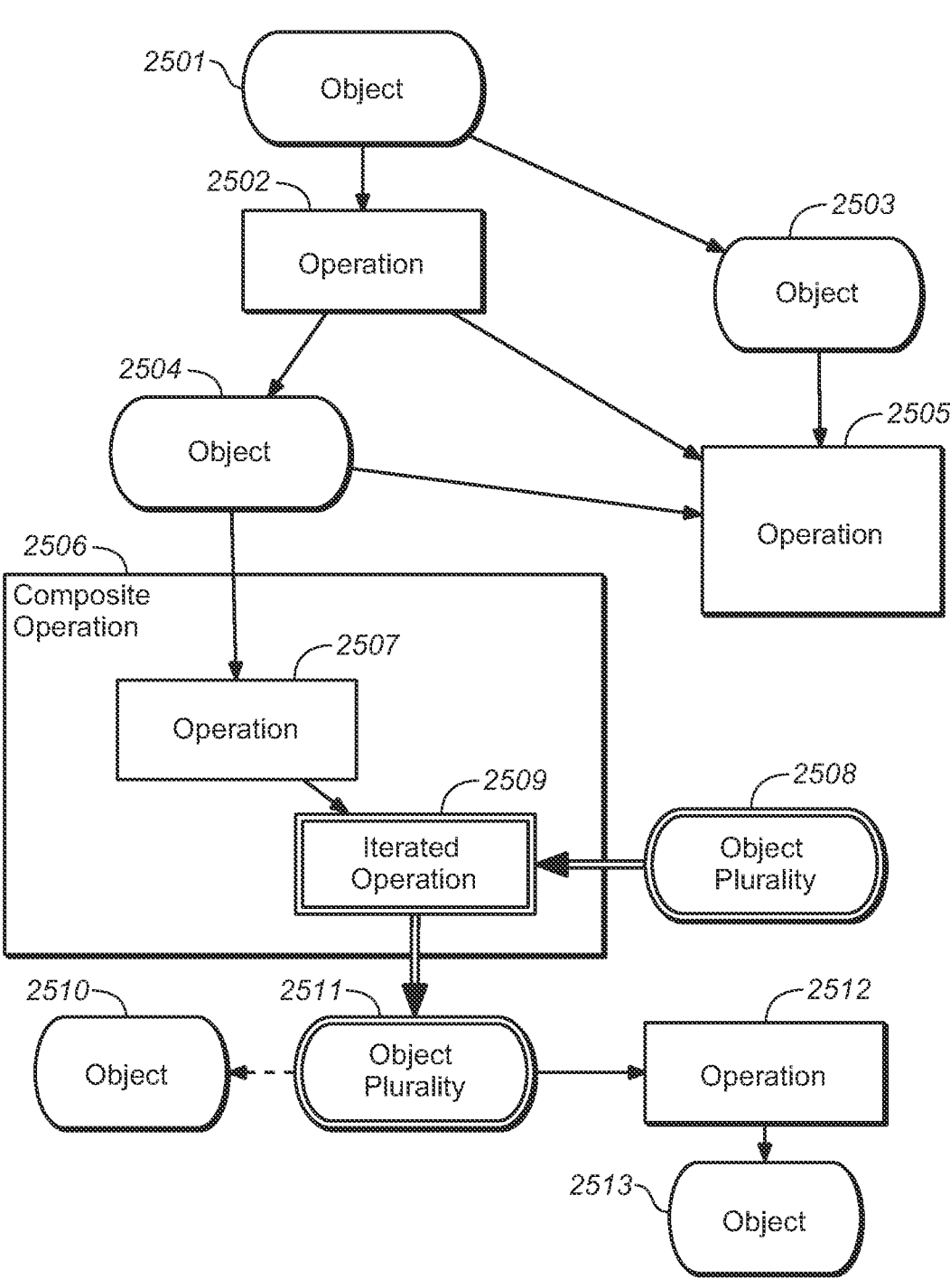
FIG. 25: Example process flow diagram for describing and demonstrating the syntax and structure of process flow diagrams as they appear in other figures.

Figures included in this disclosure may be process flow diagrams that visually depict the flow of generalized objects and operations that process and generate those objects. FIG. 25 depicts an example of a process flow diagram to aid in understanding the visual language. In this diagram, rounded boxes (e.g. at 2501 and 2503) depict objects, which may be understood as physical entities, virtual entities such as numerical data, or composite objects containing a heterogeneous aggregation of component objects. A composite object containing a homogeneous aggregation of objects is depicted by a rounded box with a double-lined boundary, e.g. as shown at 2508 and 2511. A component object extracted from a composite object is depicted with a dotted arrow, e.g. as shown connecting entities 2501 and 2503. The flow of objects in the process is shown by a solid arrow, e.g. as shown connecting entities 2501 and 2502. A squared box (e.g., at 2502 and 2505) represents an operation. Operations may generate objects, transform objects or analyze objects. The outputs of an operation are shown by arrows pointing away from its box. The output of an operation is dependent on its inputs, which may be traced by following all arrows leading into its box. Operations may be formed as a composite operation by encapsulating another process diagram, e.g. as shown at 2506. This construction enables process flow diagrams to be extended over multiple pages whereby a composite operation defined in one diagram may be invoked by reference in another diagram. Operations may be connected together in series or in parallel, the details of the order in which specific operations are performed is not necessarily defined by the process flow diagram syntax and must be inferred by accompanying description. A double-lined arrow, e.g. as shown connecting 2508 and 2509, represents iteration of the flow of a plurality of homogeneous objects, and the process flow may be identified in accompanying description using the phrase "for each . . . ". Operations that are iterated are shown with a doubled-lined squared boundary, e.g. at 2509. An iterated operation varies its input with respect to each iterated object, but may hold constant inputs with respect to non-iterated objects, e.g. as shown along the flow arrow connecting 2507 and 2509. The process flow diagrams used in this disclosure are provided to aid understanding when interpreted along with the accompanying detailed description. The process flow diagrams used in this disclosure do not constitute a formal specification for an algorithm but rather are illustrative devices provided to aid in understanding the accompanying descriptions.

The methods disclosed herein may be implemented, for example, on a computer having a 2.3 GHz Intel Core i7 processor and 8 GB of RAM using the commercially available computational software program Mathematica® (including its linear program solvers) available from Wolfram Research, Inc. It should be understood by those of ordinary skill in the art, however, that the methods disclosed herein are not limited to the above implementation and are independent of the computer/system architecture. Accordingly, the methods may equally be implemented on other computing platforms, use other computational software (whether commercially available or coded specifically for the filter design methods), and also may be hard-wired into a circuit or other computational component.

This disclosure is illustrative and not limiting. Further modifications will be apparent to one skilled in the art in light of this disclosure. For example, where methods and steps described above indicate certain events occurring in certain order, those of ordinary skill in the art will recognize that the ordering of certain steps may be modified and that such modifications are in accordance with the inventions disclosed herein. Additionally, certain of the steps may be performed concurrently in a parallel process when possible, as well as performed sequentially as described above. Acts referred to herein as operations in a method or process may also be understood as "steps" in the method or process. Therefore, to the extent there are variations of the inventions disclosed herein, which are within the spirit of this disclosure or equivalent to the inventions disclosed herein, it is the intent that this disclosure and the claims it supports will cover those variations as well. All publications and patent applications cited in this disclosure are incorporated herein by reference in their entirety as if each individual publication or patent application were specifically and individually put forth herein.

What is claimed is:

1. An ophthalmic lens comprising
   a first narrow-band dye having a peak absorption wavelength in a first spectral band between 570 nanometers and 600 nanometers, and
   a second narrow-band dye having a peak absorption wavelength in a second spectral band between 470 nanometers and 530 nanometers,
   a peak optical density of the lens in the first spectral band is at least 3 times greater than a peak optical density in the second spectral band.

2. The ophthalmic lens of claim 1, wherein the ophthalmic lens is an ophthalmic spectacle lens.

3. The ophthalmic lens of claim 1, wherein the ophthalmic lens is an ophthalmic contact lens.

4. The ophthalmic lens of claim 3, wherein the ophthalmic contact lens is blue.

5. The ophthalmic lens of claim 3, wherein the ophthalmic contact lens is purple.

6. The ophthalmic lens of claim 1, wherein the ophthalmic spectacle lens filters at least a 10 degree field of view.

7. The ophthalmic lens of claim 6, wherein the ophthalmic spectacle lens is blue.

8. The ophthalmic lens of claim 6, wherein the ophthalmic spectacle lens is purple.

9. The ophthalmic lens of claim 1, wherein the ophthalmic lens is blue.

10. The ophthalmic lens of claim 1, wherein the ophthalmic lens is purple.

11. An ophthalmic lens comprising
    a first narrow-band dye having a peak absorption wavelength in a first spectral band between 570 nanometers and 600 nanometers, and
    a second narrow-band dye different than the first narrow-band dye and having a peak absorption wavelength in a second spectral band between 400 nanometers and 430 nanometers,
    a minimum spectral transmittance of the lens in the first spectral band is less than 75%,
    a spectral transmittance of the lens at 420 nanometers is less than 10%, and
    a luminous transmittance of the lens is less than 90%, where luminous transmittance is defined according to the American National Standards Institute Z80. 3-2010 if the lens is a spectacle lens and is defined according to the American National Standards Institute Z80.20-2010 if the lens is a contact lens.

12. The ophthalmic lens of claim 11, wherein the luminous transmittance of the lens is less than 80%.

13. The ophthalmic lens of claim 12, wherein the ophthalmic lens is an ophthalmic spectacle lens.

14. The ophthalmic lens of claim 12, wherein the ophthalmic lens is an ophthalmic contact lens.

15. The ophthalmic lens of claim 11, wherein the luminous transmittance of the lens is greater than 70%.

16. The ophthalmic lens of claim 11, wherein the ophthalmic lens is an ophthalmic spectacle lens.

17. The ophthalmic lens of claim 11, wherein the ophthalmic lens is an ophthalmic contact lens.

* * * * *